(12) United States Patent
Dutta

(10) Patent No.: US 8,211,916 B2
(45) Date of Patent: Jul. 3, 2012

(54) N- AND O-SUBSTITUTED 4-[2-(DIPHENYLMETHOXY)-ETHYL]-1-[(PHENYL)METHYL]PIPERIDINE ANALOGS AND METHODS OF TREATING CNS DISORDERS THEREWITH

(75) Inventor: Aloke K. Dutta, Novi, MI (US)

(73) Assignee: Wayne State University, Detroit, MI (US)

( * ) Notice: Subject to any disclaimer, the term of this patent is extended or adjusted under 35 U.S.C. 154(b) by 1033 days.

(21) Appl. No.: 12/018,172

(22) Filed: Jan. 22, 2008

(65) Prior Publication Data

US 2008/0182991 A1  Jul. 31, 2008

Related U.S. Application Data

(63) Continuation-in-part of application No. 11/007,484, filed on Dec. 8, 2004, now Pat. No. 7,595,331, which is a continuation of application No. 10/311,796, filed on Mar. 28, 2003, now Pat. No. 6,995,268, which is a continuation of application No. PCT/US01/40964, filed on Jun. 14, 2001.

(60) Provisional application No. 60/212,921, filed on Jun. 20, 2000.

(51) Int. Cl.
*A61K 31/445* (2006.01)
*C07D 211/40* (2006.01)

(52) U.S. Cl. ........ 514/327; 514/317; 514/318; 514/328; 514/331; 546/193; 546/212; 546/214; 546/216; 546/223; 546/229; 546/232

(58) Field of Classification Search .................. 514/317, 514/318, 327, 328, 331; 546/193, 212, 214, 546/216, 223, 229, 232
See application file for complete search history.

(56) References Cited

U.S. PATENT DOCUMENTS

| | | | |
|---|---|---|---|
| 5,232,929 A | 8/1993 | DeSai et al. | |
| 5,300,499 A | 4/1994 | Chow | |
| 5,344,835 A | 9/1994 | Alker et al. | |
| 6,413,956 B1 | 7/2002 | Albaugh et al. | |
| 6,995,268 B2 | 2/2006 | Dutta | |
| 7,595,331 B2 * | 9/2009 | Dutta ........................... 514/327 |
| 2003/0225133 A1 | 12/2003 | Dutta | |
| 2005/0154021 A1 | 7/2005 | Dutta | |
| 2010/0016600 A1 | 1/2010 | Dutta | |

FOREIGN PATENT DOCUMENTS

| | | |
|---|---|---|
| EP | 0 417 698 A | 3/1991 |
| EP | 0 217 286 A | 12/2008 |
| WO | 98 50534 A | 11/1998 |
| WO | 2009 925686 A | 11/1998 |

OTHER PUBLICATIONS

M.J. Kuhar, "Neurotransmitter Uptake: A Tool in Identifying Neurotransmitter Specific Pathways," Life Sci., 13, 1623-34, 1973.

M.E.A. Reith et al., "Strucural Requirements for Cocaine Congeners to Interact with Dopamine and Serotonin Uptake Sites in Mouse Brain and to Induced Stereotyped Behavior," Biochem. Pharmacol., 1986, 35, 1123-1129.

M.C. Ritz et al., "Cocaine Inhibition of Ligand Binding at Dopamine, Norpinephrine and Serotonin Transporters: A Structure-Activity Study," Life. Sci., 1990, 46, 635-645.

M.C. Ritz et al., "Cocaine Receptors on Dopamine Transporters are Related to Self-Administration of Cocaine," Science, 1987, 237, 1219-1223.

B. Giros et al., "Hyperlocomotion and Indifference to Cocaine and Amphetamine in Mice Lacking the Dopamine Transporter," Nature, 1996, 379, 606-612.

J.M. Maloteaux et al., Eur. J. Pharm., 1988, 156, 331-340.

H.B. Niznik et al., Arch. Biochem. Biophys., 1990, 276, 424-432.

K.M. Johnson, "Phencyclidine: Behavioral and Biochemical Evidence Supporting a Role for Dopamine," Fed. Proc., 1983, 42, 2579-3583.

E.D. French et al., "Phencyclidine Binding Sites in the Nucleus Accumbens and Phencyclidine-Induced Hyperactivity are Decreased Following Legions of the Mesolimbic Dopamine System," Eur. J. Pharmacol., 1985, 116, 1-9.

H. Kinemuchi et al., "The Neurotoxicity of 1-methyl-4-phenyl-1,2,3,6-tetrahydropyridine (MPTP) and its Relevance to Parkinson's Disease," Neurochem. Int., 1987, 11, 359-373.

F.I. Carroll et al., "Cocaine Receptor: Biochemical Characterization and Structure-Activity Relationship of Cocaine Analogues at the Dopamine Transporter," J. Med. Chem., 1992, 35, 969-981.

R.A. Millius et al., "Synthesis and Receptor Binding of N-substituted Tropane Derivatives," "High Affinity Ligands for Cocaine Receptor," J. Med. Chem., 1991, 34, 1728-1731.

I. Chaudieu et al., "Role of the Aromatic Group in the Inhibition of Phencyclidine Binding and Dopamine Uptake by PCP Analogs," Pharmacol. Biochem. Behav., 1989, 32, 699-705.

J. Vignon et al., "[3H]N-[1(2-Benzo(b)thienyl)cyclohexyl]piperidine([3H]BTCP): A New Phencyclidine Analog Selective for the Dopamine Uptake Complex," Eur. J. Pharmacol., 1988, 148, 427-436.

P.H. Anderson, "Biochemical and Pharmacological Characterization of [3H]GBR 12935 Binding in Vitro to Rat Striatal Membranes: Labeling of the Dopamine Uptake Complex," J. Neurochem., 1987, 48, 1887-1896.

(Continued)

*Primary Examiner* — Celia Chang
(74) *Attorney, Agent, or Firm* — Brooks Kushman P.C.

(57) ABSTRACT

N- and O-substituted 4[2-diaromaticmethoxy and methylamino)alkyl] piperidines exhibit high CNS activity with respect to the dopamine transporter (DAT) and serotonin transporter (SERT). Preferred compounds exhibit highly differential behavior as between the DAT and SERT and between the DAT and the norepinephrine transporter (NET). The compounds have utility in treating CNS disorders, including but not limited to cocaine addiction, depression, and Parkinson's disease.

9 Claims, 18 Drawing Sheets

OTHER PUBLICATIONS

P.H. Anderson, "The Dopamine Uptake Inhibitor GBR 12909: Selectivity and Molecular Mechanism of Action," Eur. J. Pharmacol., 1989, 166, 493-504.

R.B. Kolhatkar et al., "Interaction of cis-(6-Benzhydrylpiperidin-3-yl)benzylamine Analogues with Monoamine Transporters: Structure-Activity Relationship Study of Structurally Constrained 3,6-Disubstituted Piperidine Analogues of (2,2-Diphenylethyl)-[1-(4-fluorobenzyl)piperidin-4-ylmethyl]amine," J. Med. Chem. 2003, 46, 2205-2215.

C. DeVries et al., "Heteroaromatic Analogs of 1-2[2-(diphenylmethoxy{ethyl]- and 1-[2[bis(4-fluorophenyl)methoxy]ethyl]-4-(3-phenylpropyl)piperazines (GBR 12935 and GBR 12909) as High-Affinity Dopamine Reuptake Inhibitors," J. Med. Chem., 1997, 40, 705-716.

D. Matecka et al., Development of Novel, Potent, and Selective Dopamine Reuptake Inhibitors Through Alteration of the Piperazine Ring of 1-[2-(diphenylmethoxy)ethyl]- and 1[2-[Bis(4-fluorophenyl)methoxy]ethyl]-4-(3-phenylpropyl) piperazines (GBR 12935 and GBR 12909), J. Med. Chem., 1996, 39, 4704-4716.

R.B. Rothman, "Tight Binding Dopamine Reuptake Inhibitors as Cocaine Antagonists," FEBS Lett., 1989, 257, 341-344.

J.R. Glowa et al., "The Effects of GBR 12909 on Responding of Rhesus Monkeys Maintained Under Schedules of Cocaine- and Food-Delivery," NIDA. Res. Monogr., 1994, 141, 12.

A.K. Dutta et al., "Structure-Activity Relationship Studies of Novel 4[2-[Bis(4-fluorophenyl)methoxy]ethy]-1-(3-phenylpropyl)piperidine Analogs: Synthesis and Biological Evaluation of the Dopamine and Serotonin Transporter Sites," J. Med. Chem., 1996, 39, 749-756.

A.K. Dutta et al., "Highly Selective, Novel Analogs of 4-[2-(diphenylmethoxy)ethyl]-1-benzylpiperidine for the Dopamine Transporter: Effect of Different Aromatic Substitutions on their Affinity and Selectivity," J. Med. Chem., 1997, 40, 35-43.

A.K. Dutta et al., "Potent and Selective Ligands for the Dopamine Transporter (DATE): Structure-Activity Relationship Studies of Novel 4-[2-(diphenylmethoxy)ethyl]-1-(3-phenylpropyl)piperidine Analogs," J. Med. Chem., 1998, 41, 699-756.

Derwent Abstract, Eur. J. Nucl. Med., (1999), 26(4), 342-347, "In Vivo Imaging of Serotonin Transporters with [99mTc] TRODAT-1 in Nonhuman Primates" [AN 1999:196775].

A.K. Dutta et al., "Tolerance in the Replacement of the Benzhydrylic O Atom in 4-[2-(Diphenylmethoxy)ethyl]-1-benzylpiperidine Derivatives by an N Atom: Development of New-Generation Potent and Selective N-Analogue Molecules for the Dopamine Transporter," J. Med. Chem., vol. 41, No. 17, pp. 3293-3297, (1996).

Database on STN CASDATA (Columbus, Ohio, USA) Abstract No. 132:119356, Hoepping et al., "Synthesis and biological evaluation of two novel DAT binding technetium complexes" Bioorg. Med. Chem. Lett. (1999) vol. 9, No. 22, pp. 3211-3216.

F. Ivy Carroll et al., "Cocaine and 3B-(4'-Substituted phenyl)tropane-2B-carboxylic Acid Ester and Amide Analogues. New High-Affinity and Selective Compounds for the Dopamine Transporter," J. Med. Chem. 1995, 38, 379-388.

J. Langston et al., "MPTP: Current Concepts and Controversies," Clin. Neuropharmac., 1986, 9, 485-507.

A.K. Dutta et al., "Positional Importance of the Nitrogen Atom in Novel Piperidine Analogs of GBR 12909: Affinity and Selectivity for the Dopamine Transporter," Med. Chem. Res., 1993, 3, 209-222?

Shoemaker, H., et al., Naunyn Schmiedebergs Arch. Pharmacol., 1985, 329, 227-235.

Baker Botts, "In Prints—Reach-Through Claims," http://www.bakerbotts.com/news/printpage.asp?pubid=19221417 (pgs), (2002).

Tatsuki, et al. "Preparation of cyclic amine . . . " CA 131:18925 (1999) (as referenced by Examiner in U.S. Appl. No. 11/007,484).

Rubini et al., "Synthesis of Isosteric Methylene-oxy . . . ," Tetrahedron v. 42(21), 6039-45 (1986).

U. Sogaard et al., "A Tolerance Study of Single and Multiple Dosing of the Selective Dopamine Uptake Inhibitor GBR 12909 in Healthy Subjects," Int. Clin. Psychopharm., 1990, 5, 237-251.

M. Khalid et al., "N,N'-disubstituted L-isoglutamines as Novel Cancer Chemotherapeutic Agent," Drugs Exp. Clin. Res. (1987), 13 (Suppl. 1), 57-60; ISSN: 0378-6501, 1987.

Database WPI Section Ch., Week 9804, Derwent Publications Ltd., London, GB; Class B03, AN 98-035793 XP002094912 & JP 09 249566 A (Takeda Chem. Ind. Ltd.) Sep. 22, 1997 (see Abstract).

Burger, "Medicinal Chemistry," p. 25 (1970).

Ghorai, S.K. et al., "High Affinity hydroxypiperidine analogues of 4-(2-benhydryloxyethyl)-1-(4-fluorobenzyl) piperidine for the dopamine transporter: stereospecific interactions in vitro and in vivo," J. Med. Chemistry, v. 46, n. 7, Mar. 27, 2003, pp. 1220-1228.

Ghorai, S.K. et al., "Supporting Information: High Affinity hydroxypiperidine analogues of 4-(2-benhydryloxyethyl)-1-(4-fluorobenzyl)piperidine for the dopamine transporter: stereospecific interactions in vitro and in vivo," J. Med. Chemistry, Mar. 27, 2003, pp. 1-20.

European Search Report dated Jul. 11, 2011 from corresponding European Appn. No. 09703852.5, filed Aug. 4, 2010, 4 pgs.

Dorwald, F.Z., "Side Reactions in Organic Synthesis," WILEY-VCH, 2005, pp. IX.

Chen, Z. et al., "Triple Uptake Inhibitors: Therapeutic Potential in Depression and Beyond," Exp. Opin. Investig. Drugs 16(9) pp. 1365-1377 (2007).

Jordan, V.C., "Tamoxifen: A Most Unlikely Pioneering Medicine," Nature Reviews, v. 2, pp. 205-213 (2003).

\* cited by examiner

Conditions - a : NaOMe, 130-140 °C; b : BzBr, AcCN, reflux; c : NaBH$_4$, MeOH;
d : ClCOOMe, reflux; e : Claisen's alkali, reflux Reaction conditions: (a) 1S-(-)Camphanic chloride, Et₃N, CH₂Cl₂; (b). HCl/MeOH, reflux, 72 h; (c) R- or S-epoxide, EtOH, 65°C, overnight.

Reaction conditions: (a) epoxide, EtOH, 65°C, overnight.

Reaction conditions: (a) 3-chloro-4'-fluoro propiophenone, $K_2CO_3$, KI, MeCN, reflux, 3h; (b) $NaBH_4$, THF, $H_2O$, 3h, RT; (c) (1S)-(−)-camphanic chloride, $Et_3N$, DMAP, $CH_2Cl_2$, 3 h; (d) $K_2CO_3$, MeOH, 12 h, RT.

Table 6. Affinity of Hydroxypiperidine Derivatives at the DAT, SERT, and NET in Rat Brain

| Compound | DAT binding, Ki, nM, [$^3$H]WIN 35, 428[a] | DAT uptake, Ki, nM, [$^3$H]DA[a] | SERT uptake, Ki, nM, [$^3$H]5-HT[a] | NET uptake, Ki, nM [$^3$H]NE[a] |
|---|---|---|---|---|
| GBR 12909[b] | 8.56 ± 1.5 | 10.6 ± 2.2 | 91.1 ± 12.8 | 102 ± 32 |
| D-225 | 6.76 ± 1.75 | 6.23 ± 2.38 | 456 ± 102 | 4.09 ± 0.11 (2) |
| D-226 | 40.1 ± 19.2 | 18.4 ± 9.5 | 420 (5) ± 62 | 27.5 ± 13.5 |
| D-230 | | 2.44 (4) ± 0.37 | 402 (4) ± 67 | 21.9 ± 3.4(2) |
| D-231 | | 4.04 (4) ± 1.22 | 1,055 (4) ± 130 | 16.5 (2) ± 3.4 |
| D-232 | | 1.55 (4) ± 0.27 | 259 (4) ± 36 | 13.1 (2) ± 0.02 |
| D-233 | | 2.97 (4) ± 0.72 | 1,790 (4) ± 312 | 16.7 |
| D-275 | 0.486 ± 0.065 | 1.06 ± 0.42 | 231 ± 49 | 115 ± 14 |
| D-276 | 2.29 ± 0.85 | 4.69 ± 2.06 | 155 ± 26 | 78.4 ± 18.1 |

[a] For binding, the DAT was labeled with [$^3$H]WIN 35, 428. For uptake by the DAT, SERT, and NET, the [$^3$H]DA, [$^3$H]5-HT, and [$^3$H]NE accumulation were measured. Results are average (SEM of three to eight independent experiments assayed in triplicate.
[b] See ref Figure 14

Fig. 13

Table 7. Affinity of Drugs at DAT, SERT, and NET in Rat Brain

| Compounds | DAT binding, Ki, nM, [$^3$H]WIN 35, 428[a] | DAT uptake, Ki, nM, [$^3$H]DA [a] | SERT uptake, Ki, nM, [$^3$H]5-HT [a] | NET uptake, Ki, nM [$^3$H]NE [a] |
|---|---|---|---|---|
| GBR 12909[b] | 10.6 ± 1.9 | 10.6 ± 2.2 | 91.1 ± 12.8 | 102 ± 32 |
| III[b] | 11.3 ± 0.9 | 9.10 ± 1.86 | | |
| IV[b] | 22.5 ± 2.1 | 18.4 ± 0.9 | | |
| D-228, 4a (S,S,R) | | 236 ± 41 | 2,895 ± 755 | 1435 ± 495 |
| D-227, 4b (S,S,S) | | 152 ± 46 | 3,117 ± 757 | 306 ± 89 |
| D-254, 4c (S,S,R) | 31.8 ± 6.0 | 25.1 ± 2.5 | 1,391 ± 298 | 170 ± 32 |
| D-272, 4d (S,S,S) | 28.9 ± 2.3 | 25.3 ± 6.9 | 2596 ± 718 | 231 ± 50 |
| D-169, 6a (S,S,R) | 148 ± 48 | 82.9 ± 7.2 | 11,216 ± 231 | 730 ± 79 |
| D-170, 6b (S,S,S) | 47.0 ± 5.6 | 16.8 ± 1.3 | 10,336 ± 539 | 259 ± 20 |
| D-250, 7a (S,S,R) | 228 ± 45 | 204 ± 34 | 12,904 ± 1440 | 954 ± 138 |
| D-251, 7b (S,S,S) | 1,039 ±179 | 266 ± 31 | 9,508 ±1,748 | 1,730 ± 387 |
| D-252, 7c (S,S,R) | 142 ± 22 | 66.5 ± 5.7 | 7,414 ± 978 | 319 ± 58 |
| D-253, 7d (S,S,S) | 649 ± 100 | 160 ± 12 | 7344 ± 1,437 | 728 ± 142 |
| D-273 (11a) | 19.9 ± 0.9 | 41.8 ± 6.9 | 11,884 ± 4136 | 388 ± 76 |
| D-274 (11b) | 13.5 ± 2.9 | 8.63 ± 1.36 | 1484 ± 366 | 418 ± 27 | a. For binding, the DAT was labeled with [$^3$H]WIN 35, 428. For uptake by DAT, SERT and NET, [3H]DA, [3H]5-HT and [3H]NE accumulation were measured. Results are average ± SEM of three to eight independent experiments assayed in triplicate. [b]See Figure 14

Fig. 15

Table 8: Selectivity ratio for uptake inhibition

| Compound | SERT uptake/ DAT uptake[a] | NET uptake/ DAT uptake[a] | DAT uptake/ DAT Binding[a] |
|---|---|---|---|
| GBR 12909 | 8.5 | 9.6 | 1.0 |
| 4a | 12.2 | 6.0 | |
| 4b | 20.5 | 2.0 | |
| 4c | 55.4 | 6.7 | 0.78 |
| 4d | 103 | 9.1 | 0.87 |
| 6a | 135 | 8.8 | 0.56 |
| 6b | 615 | 15.4 | 0.35 |
| 7a | 63.2 | 4.6 | 0.89 |
| 7b | 35.7 | 6.5 | 0.25 |
| 7c | 111 | 4.7 | 0.46 |
| 7d | 45.9 | 4.5 | 0.24 |
| 11a | 284.3 | 9.2 | 2.1 |
| 11b | 171.9 | 48.4 | 0.63 | a Ratio of Ki values

Fig. 16

Elemental Analysis Results of Final Products:

| Compounds | Calculated | | | Found | | |
| --- | --- | --- | --- | --- | --- | --- |
| | C | H | N | C | H | N |
| 4a 2(COOH)$_2$ 0.5H$_2$O | 60.70 | 5.77 | 4.72 | 60.78 | 5.72 | 4.69 |
| 4b 2(COOH)$_2$ 0.9H$_2$O | 59.97 | 5.84 | 4.66 | 59.98 | 5.71 | 4.57 |
| 4c 2(COOH)$_2$ 0.5H$_2$O | 63.15 | 6.32 | 4.75 | 63.15 | 6.31 | 4.74 |
| 4d 2(COOH)$_2$ 0.3H$_2$O | 63.53 | 6.30 | 4.78 | 63.45 | 6.42 | 4.79 |
| 6a 2(COOH)$_2$ | 65.33 | 6.31 | 4.62 | 65.17 | 6.32 | 4.58 |
| 6b 2(COOH)$_2$ 0.2H2O | 64.94 | 6.34 | 4.59 | 64.73 | 6.23 | 4.54 |
| 7a 2(COOH)$_2$ | 64.85 | 6.12 | 4.73 | 64.75 | 6.20 | 4.71 |
| 7b 2(COOH)$_2$ 0.3H$_2$O | 64.27 | 6.17 | 4.68 | 64.24 | 6.21 | 4.73 |
| 7c 2(COOH)$_2$ 0.2H$_2$O | 62.57 | 5.81 | 4.56 | 62.48 | 5.87 | 4.60 |
| 7d 2(COOH)$_2$ 0.3H$_2$O | 62.39 | 5.82 | 4.55 | 62.29 | 5.85 | 4.59 |
| 11a 2(COOH)$_2$ 1.5H$_2$O | 60.82 | 6.19 | 4.30 | 60.43 | 5.95 | 4.23 |
| 11b 2(COOH)$_2$ 0.5H$_2$O | 62.55 | 6.04 | 4.42 | 62.54 | 5.94 | 4.33 |

Fig. 17

N- AND O-SUBSTITUTED 4-[2-(DIPHENYLMETHOXY)-ETHYL]-1-[(PHENYL)METHYL]PIPERIDINE ANALOGS AND METHODS OF TREATING CNS DISORDERS THEREWITH

CROSS-REFERENCE TO RELATED APPLICATIONS

This application is a continuation-in-part of U.S. application Ser. No. 11/007,484 filed Dec. 8, 2004, now U.S. Pat. No. 7,595,331 issued Sep. 29, 2009, which is a continuation of U.S. application Ser. No. 10/311,796, filed Mar. 28, 2003, now U.S. Pat. No. 6,995,268 issued Feb. 7, 2006, which claims the benefit of PCT application PCT/US01/40964, filed Jun. 14, 2001, which claims the benefit of U.S. provisional application Ser. No. 60/212,921, filed Jun. 20, 2000 now expired. The entire disclosures of these applications are hereby incorporated by reference.

TECHNICAL FIELD

The present invention pertains to novel pharmacologically active compounds which exhibit activity for monoamine transporter systems, specifically for the dopamine transporter ("DAT"), serotonin transporter ("SERT"), and norepinephrine transporter ("NET"). The novel compounds exhibit a high differential in activity for the DAT relative to the SERT.

BACKGROUND OF THE INVENTION

The dopamine transporter is a presynaptically located macromolecule which plays an important role in pathophysiocological processes in the central nervous system (CNS). The DAT terminates dopaminergic neurotransmission by reaccumulation of released dopamine into presynaptic neurons, M. J. Kuhar, "Neurotransmitter Uptake: A Tool in Identifying Neurotransmitter Specific Pathways", LIFE SCI., 13, 1623-34, 1973. In cocaine addiction, binding of cocaine to the DAT and consequent blockage of dopamine uptake appears to be related to the reinforcing properties of the drug. M. E. A. Reith et al., "Structural Requirements for Cocaine Congeners to Interact With Dopamine and Serotonin Uptake Sites in Mouse Brain and to Induced Stereotyped Behavior", BIOCHEM. PHARMACOL., 1986, 35, 1123-1129; M. C. Ritz et al., "Cocaine Inhibition of Ligand Binding At Dopamine, Norpinephrine and Serotonin Transporters: A Structure-Activity Study", LIFE. SCI., 1990, 46, 635-645; M. C. Ritz et al., "Cocaine Receptors On Dopamine Transporters Are Related to Self-Administration of Cocaine", SCIENCE, 1987, 237, 1219-1223; B. Giros et al., "Hyperlocomotion and Indifference to Cocaine and Amphetamine in Mice Lacking the Dopamine Transporter", NATURE, 1996, 379, 606-612. Also associated with the transport function is concentration of neurotoxic chemicals in dopaminergic neurons which is implicated in Parkinson's disease. The transporter macromolecule may be a marker for Parkinson's, H. Shoemaker et al., NAUNYN SCHMIEDEBERGS ARCH. PHARMACOL., 1985, 329, 227-235 and J.-M. Maloteaux et al., EUR. J. PHARM., 1988, 156, 331-340, as evidenced by its absence in tissue sections of Parkinson's diseased putamen. H. B. Niznik et al., ARCH. BIOCHEM. BIOPHYS., 1990, 276, 424-432 and M. J. Kaufman et al., SYNAPSE, 1991, 9, 43-49. Consequently, potent yet selective ligands for the DAT have potential for in vivo monitoring of primary targets of cocaine in the brain, for characterization of cocaine binding sites, for pharmacotherapeutic agents for treatment of cocaine addition, and for monitoring of Parkinson's Disease.

Cocaine is known to bind to various neurotransporter systems in the brain, M. E. A. Reith et al., op. cit., but the reinforcing effect of cocaine which is a factor in cocaine addition, is believed to be initiated by binding to the DAT, causing inhibition of dopamine transport. Phencyclidine (PCP), a psychoactive drug of abuse, is also known to exhibit at least some of its behavioral effects through binding to the DAT. K. M. Johnson, "Phencyclidine: Behavioral and Biochemical Evidence Supporting a Role For Dopamine", FED. PROC., 1983, 42, 2579-2583; E. D. French et al., "Phencyclidine Binding Sites in the Nucleus Accumbens and Phencyclidine-Induced Hyperactivity are Decreased Following Lesions of the Mesolimbic Dopamine System", EUR. J. PHARMACOL., 1985, 116, 1-9. The DAT further plays a crucial role in the neurotoxic action of 1-methyl-4-phenyl-1,2,3,6-tetrahydropyridine (MPTP) which induces idiopathic Parkinson's syndrome in humans. J. Langston et al., MPTP: Current Concepts and Controversies", CLIN. NEUROPHARMAC., 1986, 9, 485-507; H. Kinemuchi et al., "The Neurotoxicity of 1-methyl-4-phenyl-1,2,3,6-tetrahydropyridine (MPTP) and its Relevance to Parkinson's Disease", NEUROCHEM. INT., 1987, 11, 359-373. The serotonin transporter (SERT) is also implicated in numerous neurological processes. For example, SERT is strongly implicated in depression and drug addiction.

Several classes of compounds have been developed to characterize cocaine and PCP binding sites at the DAT. M. E. A. Reith et al., op. cit., F. I. Carroll et al., "Cocaine Receptor: Biochemical Characterization and Structure-Activity Relationship of Cocaine Analogues at the Dopamine Transporter", J. MED. CHEM., 1992, 35, 969-981; R. A. Millius et al., "Synthesis and Receptor Binding of N-substituted Tropane Derivatives", "High Affinity Ligands For Cocaine Receptor", J. MED. CHEM., 1991, 34, 1728-1731; I. Chaudieu et al., "Role of the Aromatic Group in the Inhibition of Phencyclidine Binding and Dopamine Uptake by PCP Analogs", PHARMACOL. BIOCHEM. BEHAV., 1989, 32, 699-705. Extensive structure-activity relationship (SAR) studies of cocaine analogs resulted in the development of potent and selective tropane derivatives which bind to the DAT. Some well known compounds of this class include CFT (Win 35,428) and RTI-55. The similarity of the structures of these tropane derivatives and cocaine is readily apparent.

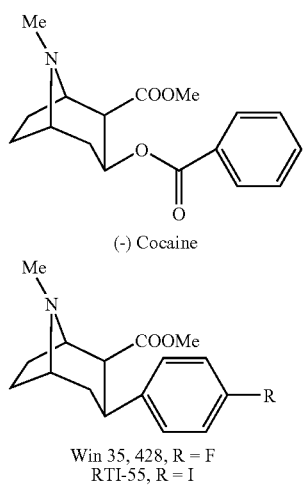

(-) Cocaine

Win 35, 428, R = F
RTI-55, R = I

More recent reports describe yet more potent and selective tropanes, P. C. Meltzer et al., "Substituted 3-phenyltropane Analogs of Cocaine: Synthesis, Inhibition of Binding At Cocaine Recognition Sites, and Positron Emission Tomography Imaging", J. MED. CHEM., 1993, 36, 855-862; F. I. Carroll et al., "Cocaine and 3β-(4'-substituted phenyl)tropane-2β-carboxylic acid ester and amide analogues. New High-affinity and Selective Compounds for the Dopamine Transporter", J. MED. CHEM., 1995, 38, 379-388. In similar fashion, modification of PCP led to development of more potent analogs, I. Chaudieu et al., "Role of the Aromatic Group in the Inhibition of Phencyclidine Binding and Dopamine Uptake By PCP Analogs", PHARMACOL. BIOCHEM. BEHAV., 1989, 32, 699-705; and J. Vignon et al., "[$^3$H]N-[1-(2-Benzo(b)thienyl)cyclohexyl]piperidine([$^3$H]BTCP): A New Phencyclidine Analog Selective for the Dopamine Uptake Complex", EUR. J. PHARMACOL., 1988, 148, 427-436.

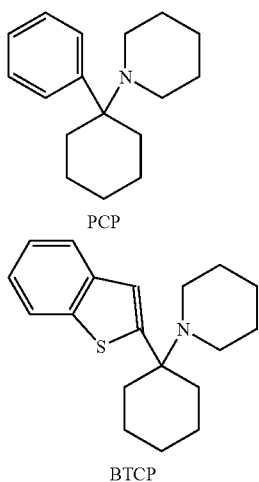

PCP

BTCP

The "GBR" class of compounds, P. Van der Zee et al., "Aryl 1,4-dialk(en)ylpiperazines as Selective and Very Potent Inhibitors of Dopamine Uptake", EUR. J. MED. CHEM, 1980, 15, 363-370, are known for their unusually high selectivity and potency for the DAT.

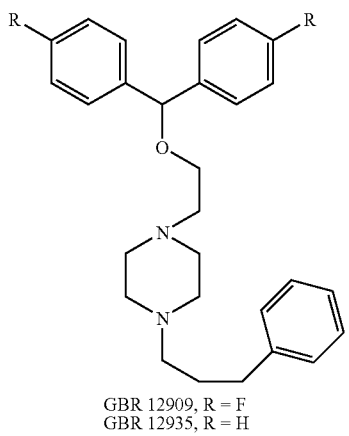

GBR 12909, R = F
GBR 12935, R = H

Two of these, with R=F and R=H, have affinities in the low nanomolar range. P. H. Anderson, "Biochemical and Pharmacological Characterization of [$^3$H]GBR 12935 Binding in Vitro to Rat Striatal Membranes: Labeling of the Dopamine Uptake Complex", J. NEUROCHEM., 1987, 48, 1887-1896; P. H. Anderson, "The Dopamine Uptake Inhibitor GBR 12909: Selectivity and Molecular Mechanism of Action", EUR. J. PHARMACOL., 1989, 166, 493-504. An extensive structure/activity relationship (SAR) study produced several very potent compounds for the DAT. C. DeVries et al., "Heteroaromatic Analogs of 1-[2-(diphenylmethoxy)ethyl]- and 1-[2-[bis(4-fluorophenyl)methoxy]ethyl]-4-(3-phenylpropyl)piperazines (GBR 12935 and GBR 12909) as High-Affinity Dopamine Reuptake Inhibitors", J. MED. CHEM., 1997, 40, 705-716; D. Matecka et al., "Development of Novel, Potent, and Selective Dopamine Reuptake Inhibitors Through Alteration of the piperazine Ring of 1-[2-(diphenylmethoxy) ethyl]- and 1-[2-[Bis(4-fluorophenyl)methoxy]ethyl]-4-(3-phenylpropyl)piperazines (GBR 12935 and GBR 12909)", J. MED. CHEM., 1996 39, 4704-4716. Radiolabeling of these compounds has facilitated elucidation of neuropharmacological activity. The GBR with R=F dissociates very slowly from the DAT, R. B. Rothman, "Tight Binding Dopamine Reuptake Inhibitors as Cocaine Antagonists", FEBS LETT., 1989, 257, 341-344 and attenuates increase in extracellular dopamine levels induced by cocaine as measured by microdialysis. R. B. Rothman, op. cit.; U. Sogaard et al., "A Tolerance Study of Single and Multiple Dosing of the Selective Dopamine Uptake Inhibitor GBR 12909 in Healthy Subjects", INT. CLIN. PSYCHOPHARM., 1990, 5, 237-251. This compound was non-stimulatory in human volunteers, J. R. Glowa et al., "The Effects of GBR 12909 on Responding of Rhesus Monkeys Maintained Under Schedules of Cocaine- and Food-Delivery", NIDA. RES. MONOGR., 1994, 141, 12, and has recently been shown to block cocaine self-administration behavior in the rhesus monkey. A. K. Dutta et al., "Positional Importance of the Nitrogen Atom in Novel Piperidine Analogs of GBR 12909: Affinity and Selectivity for the Dopamine Transporter", MED. CHEM. RES., 1993, 3, 209-222. Such studies raise the possibility that suitable compounds may serve as cocaine antagonists without being themselves addictive.

SUMMARY OF INVENTION

The present invention pertains to N- and O-versions of 4-[2-diarylamino or oxoalkyl]piperidine derivatives which exhibit neuropharmacological activity with respect to the DAT, the SERT, and/or the NET. Preferred compounds of this class exhibit low nanomolar activity with respect to the DAT, and high differential binding activity with respect to the DAT compared with that for the SERT and for the NET.

BRIEF DESCRIPTION OF THE DRAWINGS

FIG. 13 provides a representation of Table 6;

FIG. 15 provides a representation of Table 7;

FIG. 16 provides a representation of Table 8; and

FIG. 17 provides a representation of Table 9;

DESCRIPTION OF THE PREFERRED EMBODIMENTS

Figure 1:
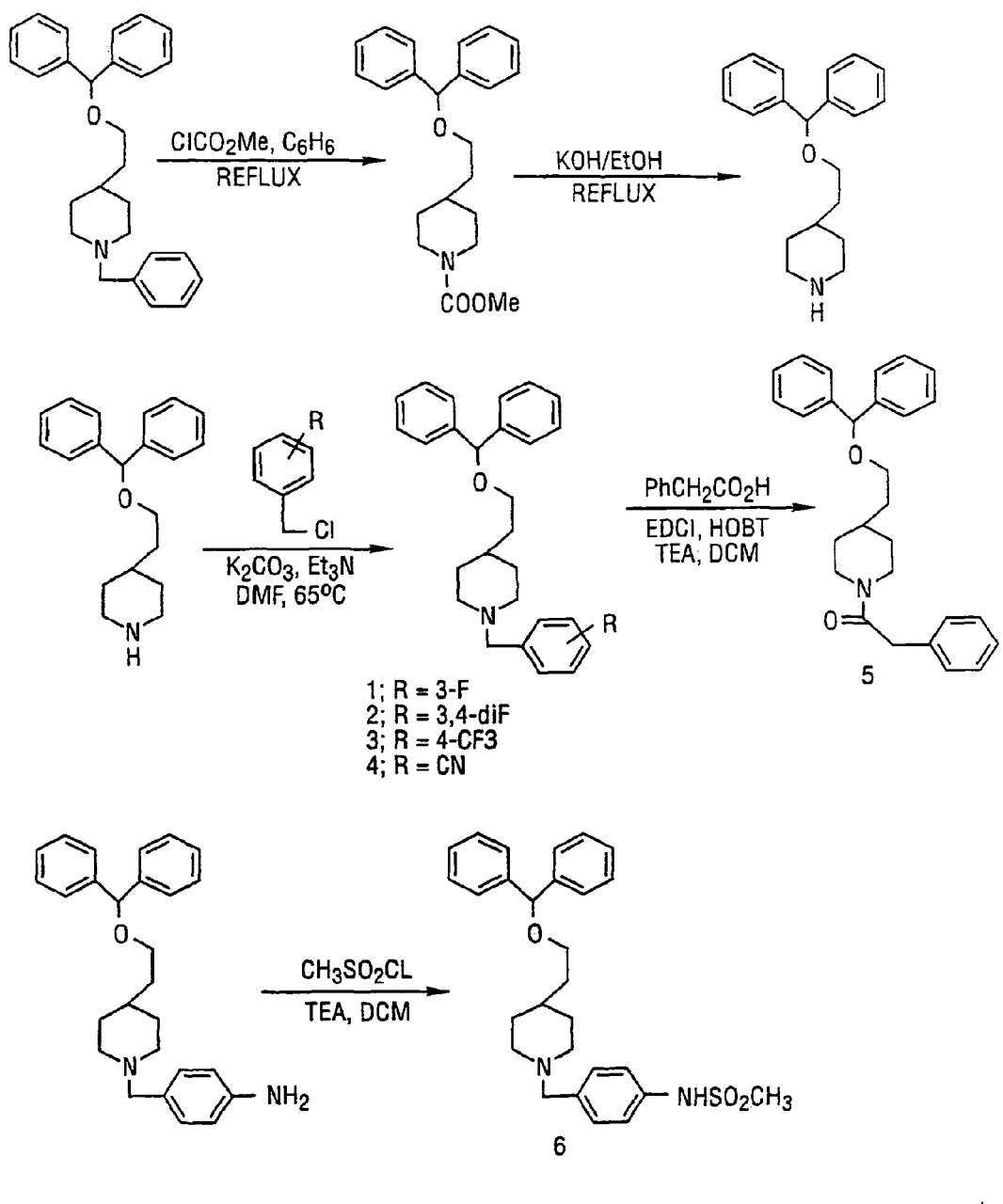
FIG. 1 illustrates one synthesis scheme and the structures of certain of the subject invention compounds.
Figure 2:
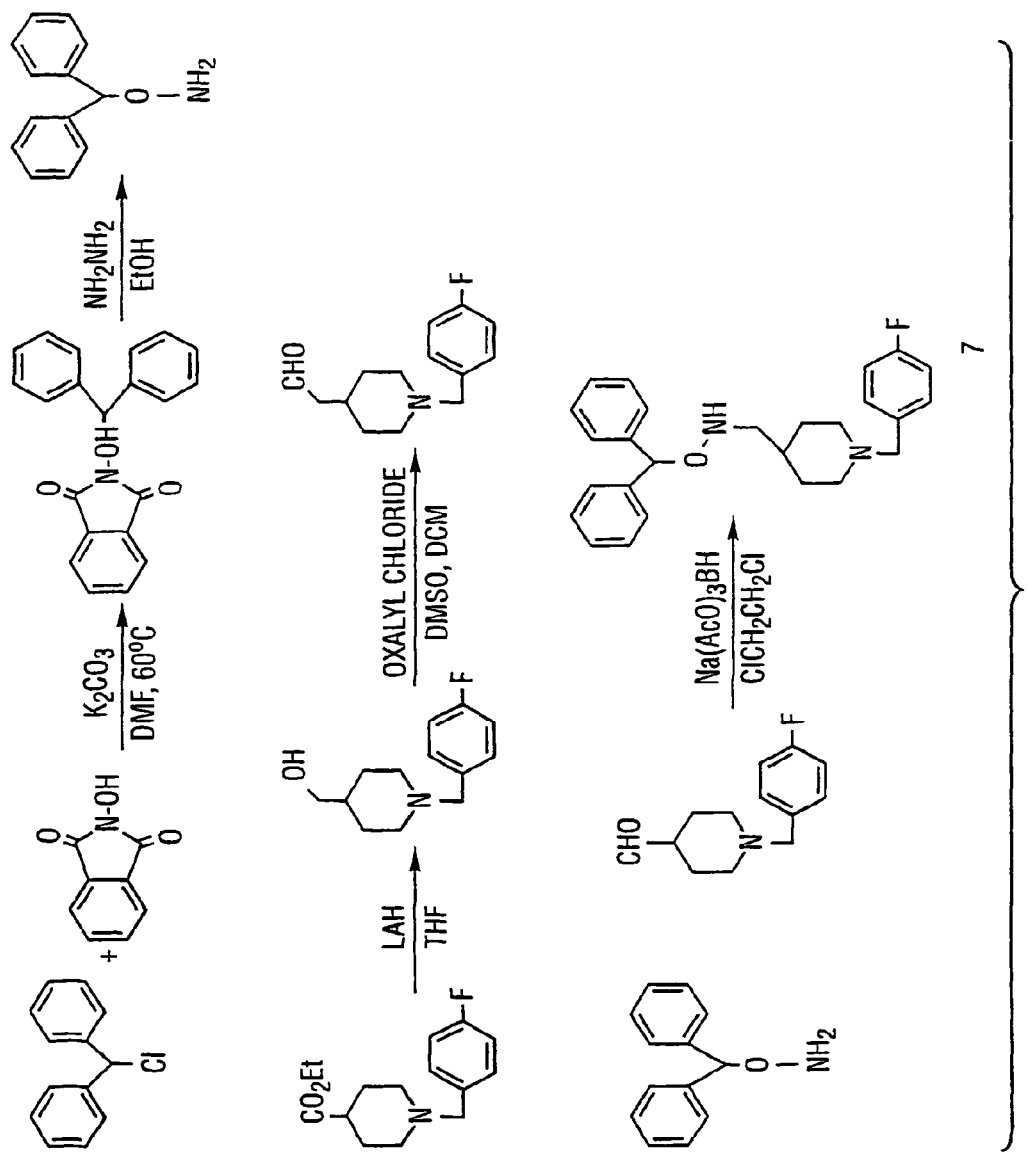
FIG. 2 illustrates a further synthesis scheme and the structures of certain of the subject invention compounds.
Figure 3:
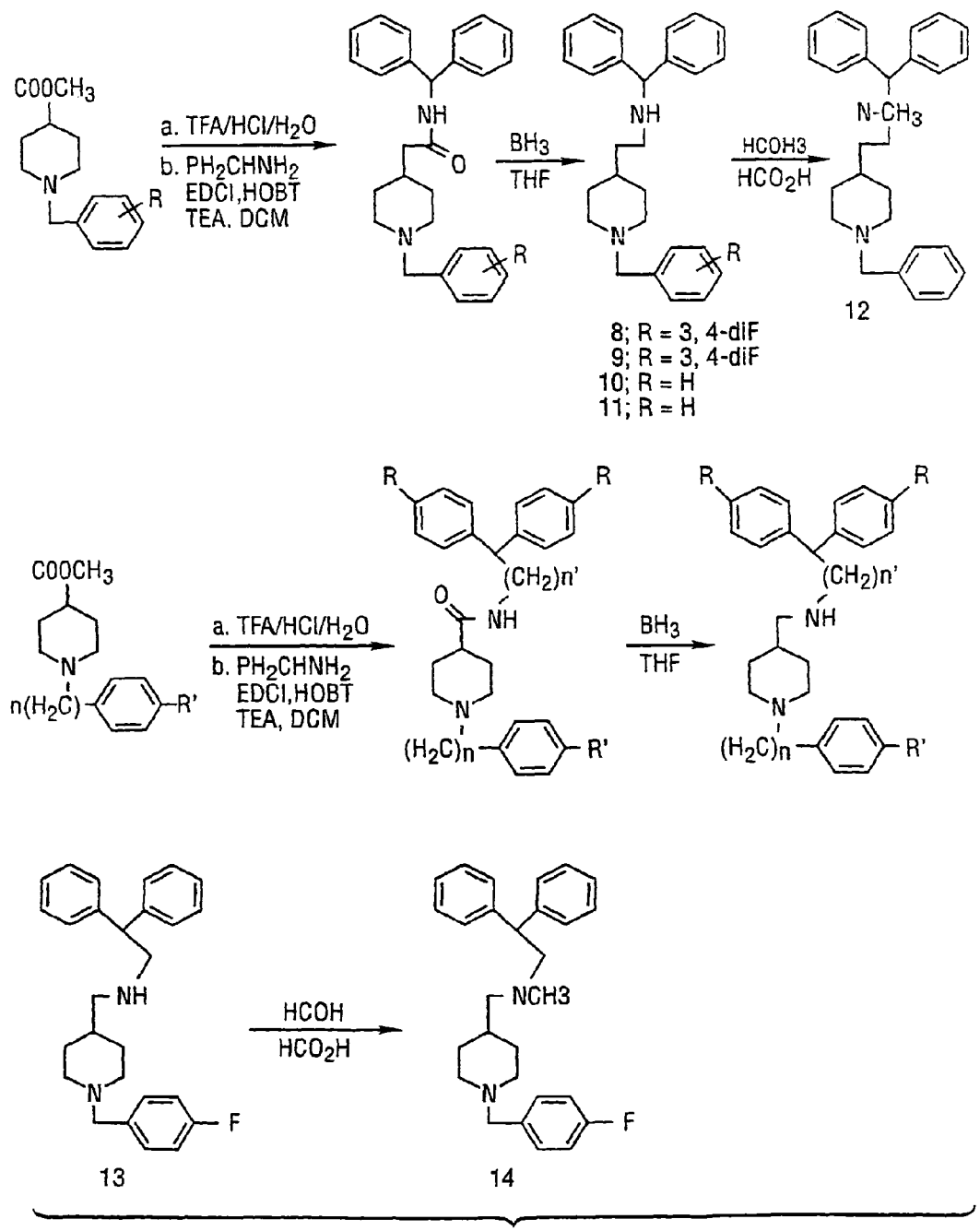
FIG. 3 illustrates a further synthesis scheme and the structures of certain of the subject invention compounds.
Figure 4:
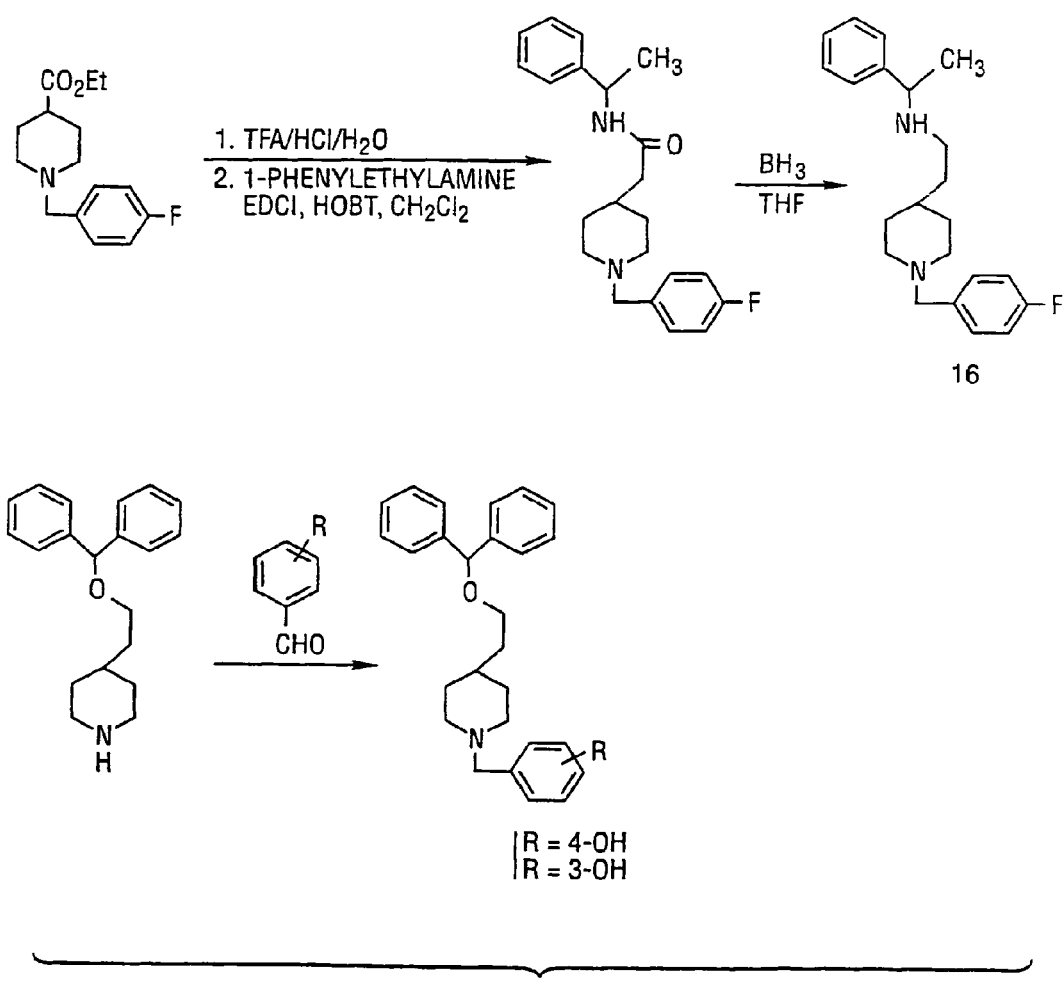
FIG. 4 illustrates a further synthesis scheme and the structures of certain of the subject invention compounds.
Figure 5A:
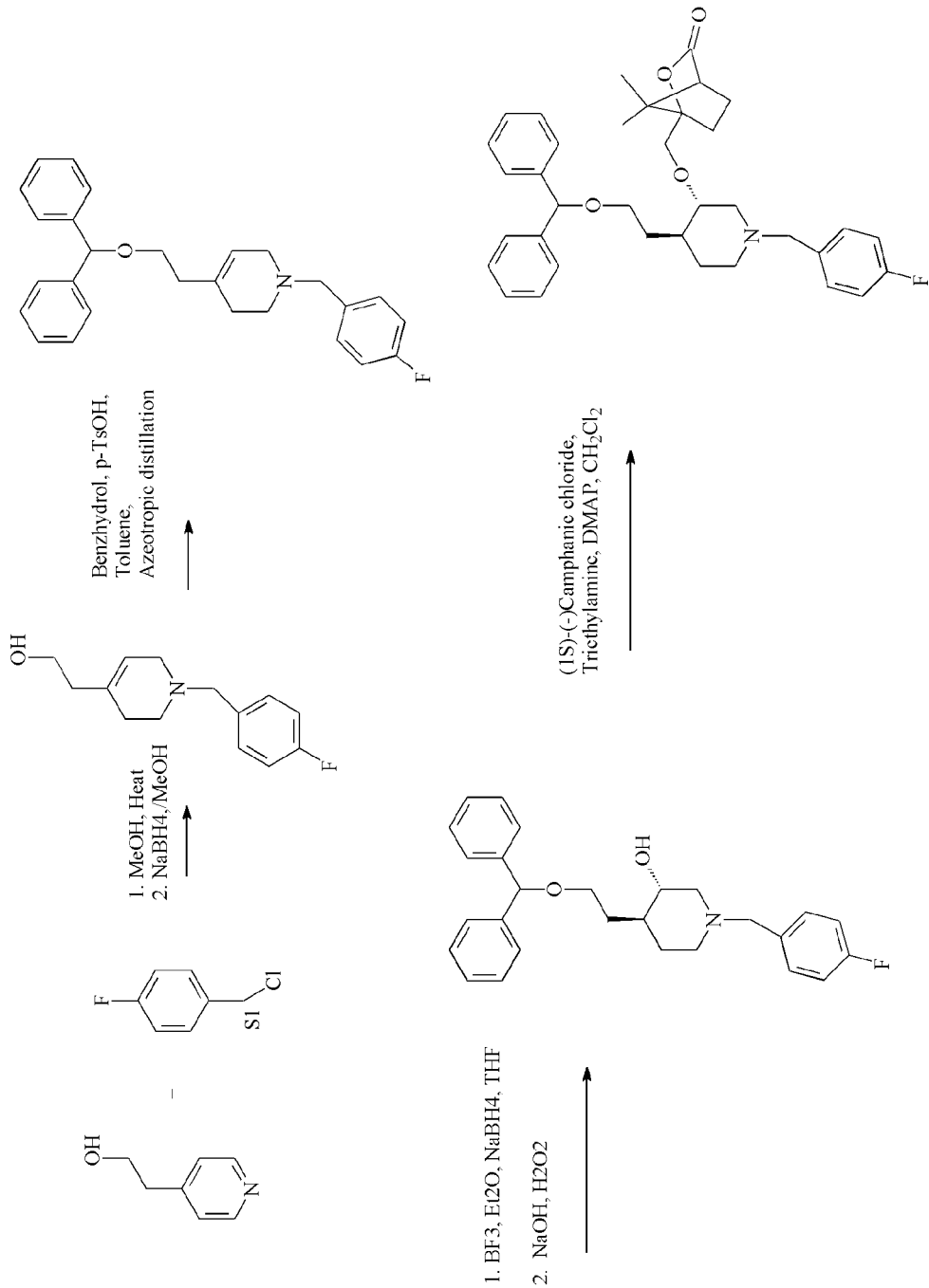
FIGS. 5A and 5B illustrate another synthesis scheme and the structures of certain of the subject invention compounds.
Figure 5B:
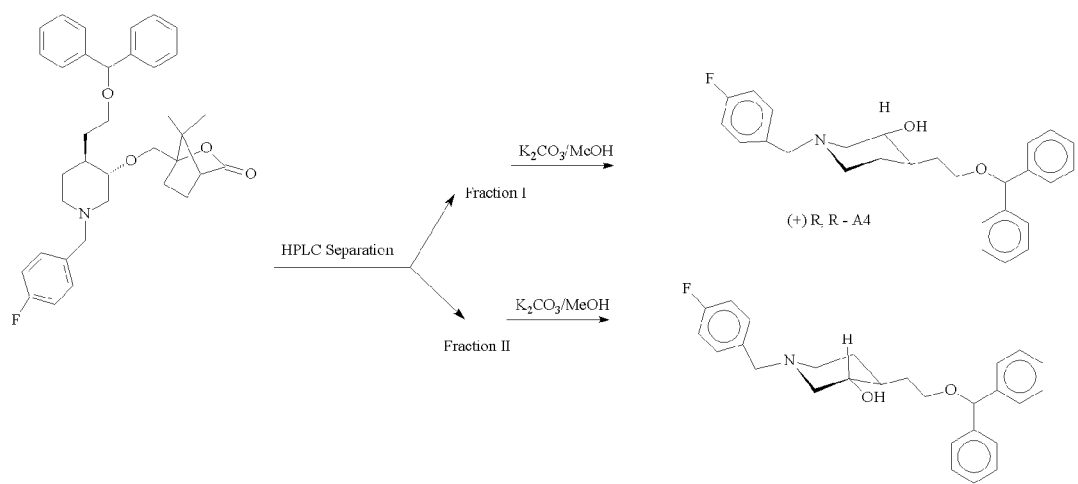
Figure 6:
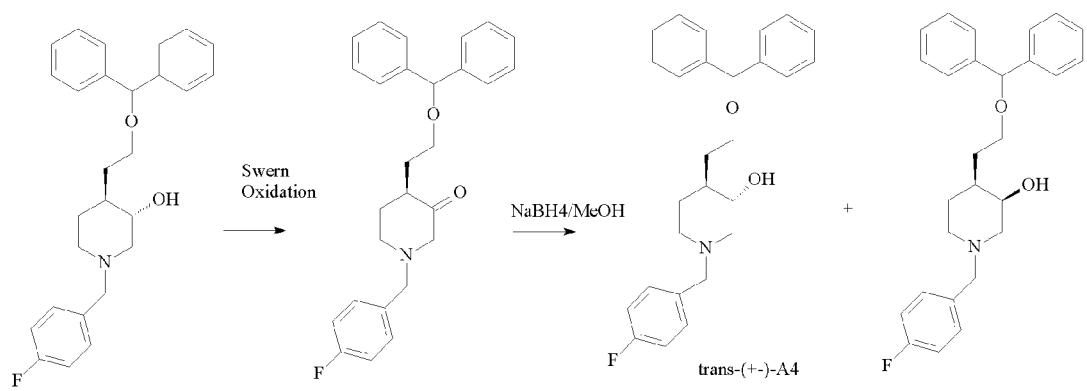
FIG. 6 illustrates another synthesis scheme and the structures of certain of the subject invention compounds.

The compounds of the present invention correspond to the formula:

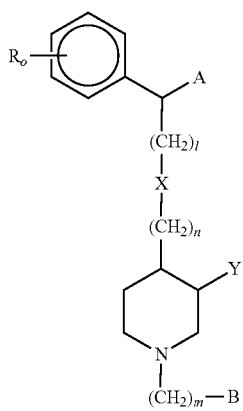

(A)

wherein A is

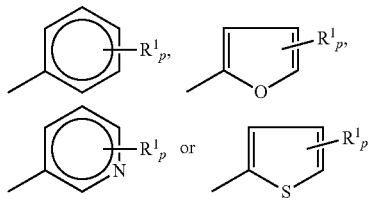

and B is

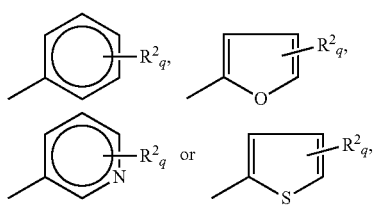

and where X is selected from the group consisting of —NH—, —NR$^4$—, —S— and —O—, R$^4$ is C$_{1-4}$ alkyl, NH$_2$, C$_{1-4}$ hydroxyalkyl, halogenated C$_{1-4}$ alkyl, C$_{2-4}$ alkenyl, C$_{2-4}$ hydroxyalkenyl, halogenated C$_{2-4}$ alkenyl, C$_{2-4}$ and alkynyl, and C$_{2-4}$ halogenated alkynyl, Y is —H, —NH$_2$, —OH, =O, or —O—C(O)—R$^5$;

l is 0, 1, or 2, preferably 0 or 1, more preferably 0;

n is 1 or 2, preferably 2;

m is 1, 2, 3, or 4, preferably 1;

o is 0, 1, 2, 3, or 4, preferably 0, 1, or 2, most preferably 0 or 1;

p is 0, 1, 2, 3, or 4, preferably 0, 1, or 2, most preferably 0 or 1;

q is 0, 1, 2, or 3, preferably 0 or 1;

R, R$^1$, and R$^2$ are selected from the group consisting of H, F, Cl, Br, I, CN, COOEt, OH, NO$_2$, NH$_2$, OR$^5$, wherein R$^5$ is C$_{1-8}$ alkyl, C$_{5-6}$ cycloalkyl, or C$_{2-8}$ alkenyl or R$^2$ is a 5 or 6 membered heterocycle; preferably a heterocycle selected from the group consisting of:

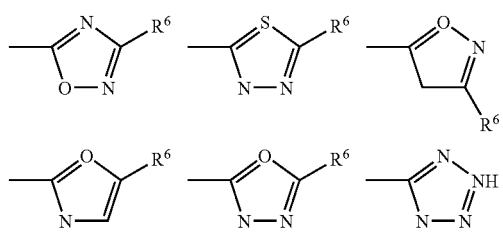

wherein R$^6$ may be C$_{1-4}$ alkyl, substituted or unsubstituted phenyl or naphthyl, it being understood that the hydroxyl group is not substituted onto an ethylenic carbon;

and where one or more CH$_2$ groups of —(CH$_2$)$_m$— are optionally substituted by CR$^7$, R$^{,7}$;

R$^7$ is H, —OR$^{11}$, or —NR$^{11}$;

R$^{,7}$ is H, —C$_{1-8}$ alkyl or R$^7$, R$^{,7}$ are combined together as =O;

R$^{11}$ is H, C$_{1-8}$ alkyl, C$_{2-8}$ alkylene, C$_{6-18}$ alkyl-aryl, or —COOR$^{12}$;

R$^{12}$ is C$_{1-8}$ alkyl, C$_{2-8}$ alkylene, or C$_{6-18}$ alkyl-aryl;

or a pharmaceutically acceptable salt or derivative thereof.

The compounds of the present invention also include those of the formula:

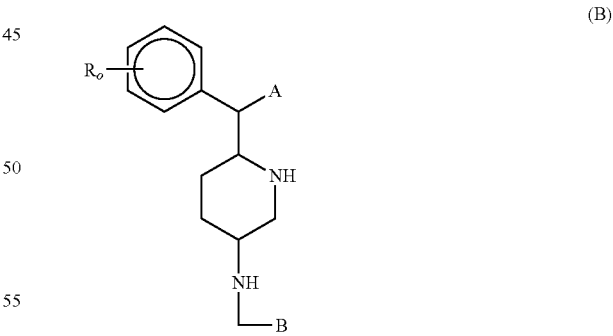

(B)

where A, B, R, and o are defined as above.

In the above formulae, A and B are preferably

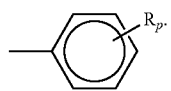

where p is 1 or 2. In the above formula, when m is 2 or 3, one of the methylene hydrogens may be substituted by OR$^7$ where R$^7$ is alkyl, preferably C$_{1-16}$ alkyl, more preferably C$_{1-4}$ lower alkyl, or C$_{2-18}$ alkylene, or

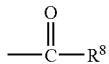

where R$^8$ is C$_{1-18}$ alkyl or C$_{2-18}$ alkylene.

Preferably, the compounds of the formula (A) correspond to

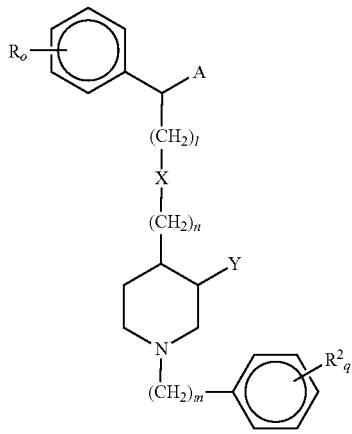

In a variation, the present invention does not include compounds falling within structural Formula I or its preferred subset, when the following conditions are met:

When A is phenyl, X is O, Y is H, l is 0, m=1, and n is 1,
R, R$^1$ and R$^2$ are not all H when B is phenyl; and
R and R$^1$ are not both F when B is phenyl;

When A is phenyl, X is O, Y is H, l is 0, m=1, and n=z,
when R$^2$ and R$^1$ are both H and B is phenyl, R$^2$ is not halo, methoxy, methyl, nitro, or amino when q is 1, and is not 3-chloro-4-fluoro when q is 2;
when R and R$^1$ are 4-fluoro, B is not an unsubstituted phenyl;
when R is 4-halo, B is phenyl, and q is 1, R$^2$ is not F;

When A is phenyl, X is O, Y is H, l is 0, n is 2, m is 2, and B is unsubstituted phenyl,
when o and p are both 1, R and R$^1$ are not both halo;
when A is phenyl, l is 0, n is 2, and m is 2, at least one of R, R$^1$, and R$^2$ is other than H;

When A is phenyl, B is phenyl, X is O, Y is H, l is 0, m is 2, l is 2, and q is 0, R
and R$^1$ are not both methyl;

When A is phenyl, X is O, Y is H, B is phenyl, l is 0, m is 2, and n is 1, not all of
R, R$^1$, and R$^2$ are H,
when r is 0 and o and p are 1, R and R$^1$ are not both 4-fluoro;

When A is phenyl, X is O, Y is H, l is 0, m is 3, and n is 2,
when B is phenyl, q is 1, and R$^2$ is H, o and p are not both zero, when B is phenyl, o and p are not both 1 when R and R$^1$ are both 4-halo or are both methoxy;

When X is O, Y is H, o is 0 and A is unsubstituted phenyl, 1 is 0, m is 3, and n is 2, B is not 4-fluorophenyl or a 6 membered heteroaryl ring bonded to the (CH$_2$)$_m$ group at the 3-ring position;

When X is O, Y is H, A is unsubstituted thiophenyl, 1 is 0, m is 3, n is 2, Y is H,
and B is unsubstituted phenyl, o is other than 0 but is not 1 when R is 4-fluoro;

When X is O, Y is H, A is unsubstituted thiophenyl, o is 0, l is 0, m is 1, and l is
2, B is not phenyl, 3-pyridyl, or 4-(fluorophenyl).

When X is O, Y is H, A is unsubstituted phenyl, l is 0, m is 1, and n is 2, B is not
unsubstituted thiophenyl or unsubstituted 2,3-benzothiophenyl.

When X is NH, Y is H, A is phenyl, l is 0, m is 1, and n is 2,
when q is 0, o is 1 and p is 1, R and R$^1$ are not both 4-fluoro,
when q is 1, o is 0 and p is 0, B is not 4-(fluorophenyl).

The compounds of the present invention also include those having the structure

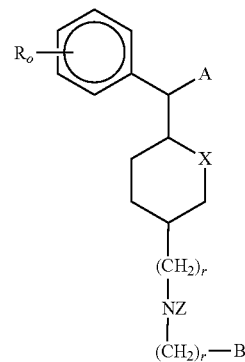

wherein A is defined as before and may also be COOCH$_3$, =O, CH$_3$, F, or OH; X is O, S, NH, NR$^9$ or N— where the remaining valence of N with Z forms a ring structure; r is 0-8, preferably 0-4, and more preferably 0, 1, or 2, Z is H or C$_{1-4}$ alkylene, preferably H or C$_{1-2}$ alkylene, the alkylene groups, when present, forming a ring structure with X when X is N—, and B is as defined previously, or is H, CH$_3$, —CH=CH$_2$, and R$^9$ is

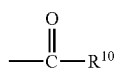

wherein R$^{10}$ is C$_{6-20}$ alkyl. Preferred compounds of this structure include those where A is substituted phenyl, X is NH, Z is H, and B is substituted phenyl, and those where X is N—, r is 0 and Z is —CH$_2$CH$_2$—, or —CH$_2$CH$_2$CH$_2$—, forming a six or seven membered ring including both nitrogens.

The compounds of the present invention also include those having the structure:

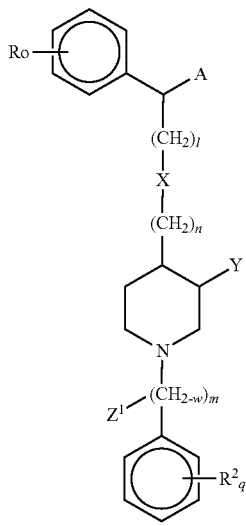

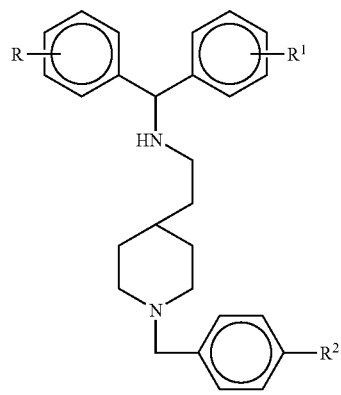

where all symbols are the same as those set forth above unless explicitly stated to be different. For example, R, $R^2$, X, Y, l, m, o, and q are defined above. w is a number representing that one or more hydrogen atoms of one or more methylene groups are replaced by $Z^1$.

$Z^1$ is —H, —$NH_2$, —OH, =O, —Oalkyl (e.g. $C_{1-8}$), —Oaryl (e.g. $C_{6-16}$), or —O—C(O)—$R^5$. It should be appreciated that in the formula above, a Z replaces at least one hydrogen of a $CH_2$ group. In this variation, the provisos set forth above are also applicable to this structure. A particularly useful variation is given by the following formula:

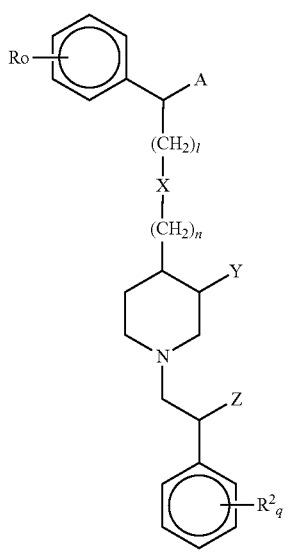

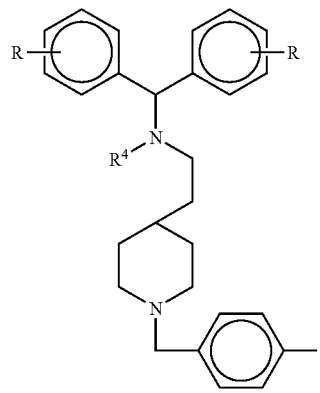

In a particularly useful variation, $Z^1$ is H or OH.

Examples of structural formulae encompassed by the above definition are the following where $R^2$ group shown represents one or more than one $R^2$, preferably one or two $R^2$ groups, which may occupy any ring position:

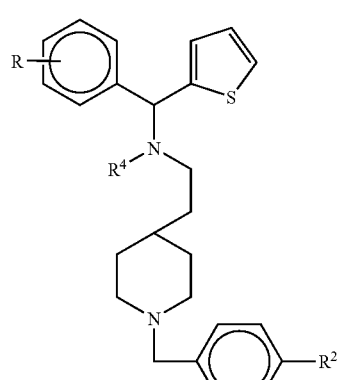

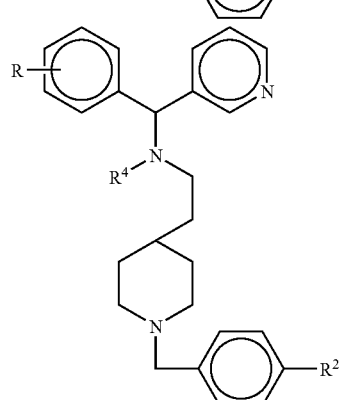

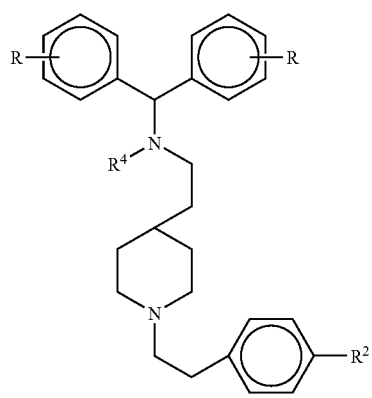
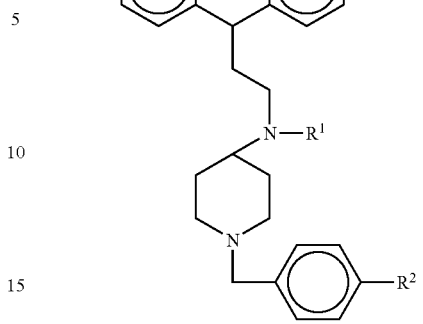
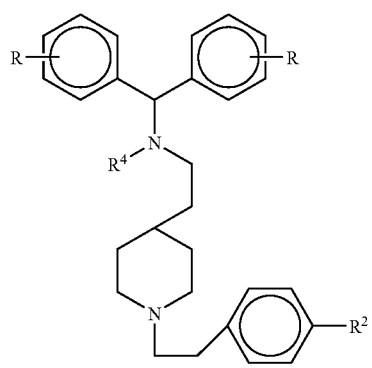
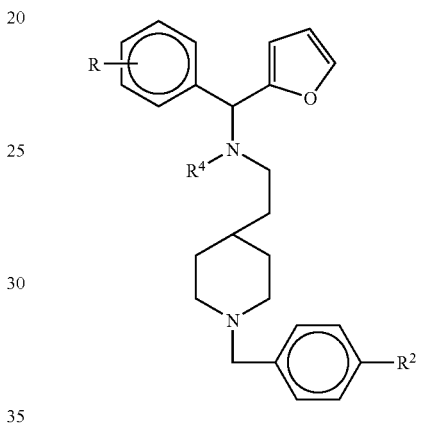
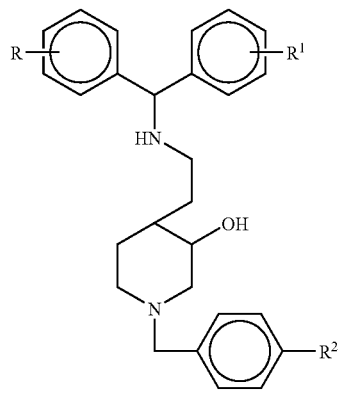
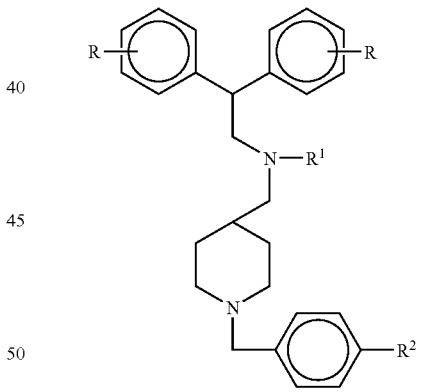
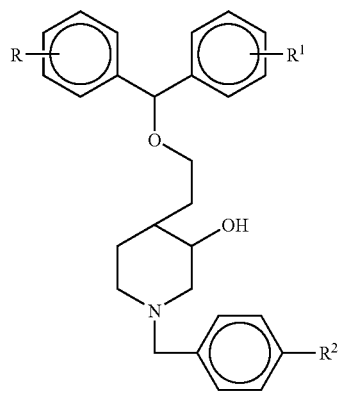
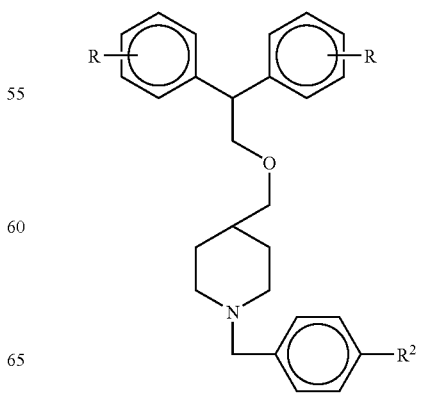

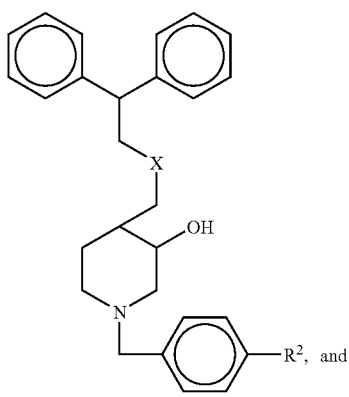

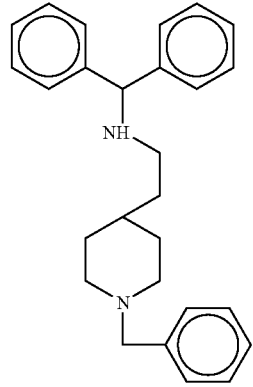

wherein in the latter two compounds, X is preferably NH or O.

Preferred compounds are those where substituents on the N-arylalkyl moiety are electronegative and electron withdrawing groups. In particular, compounds having the structural formulae

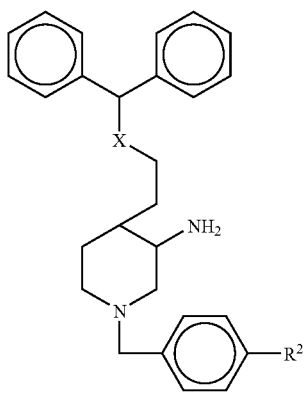

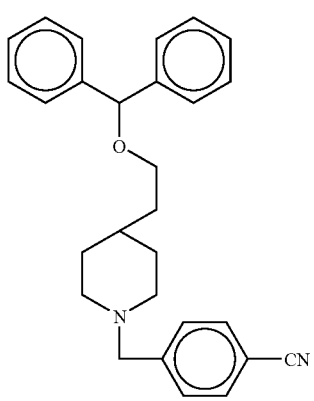

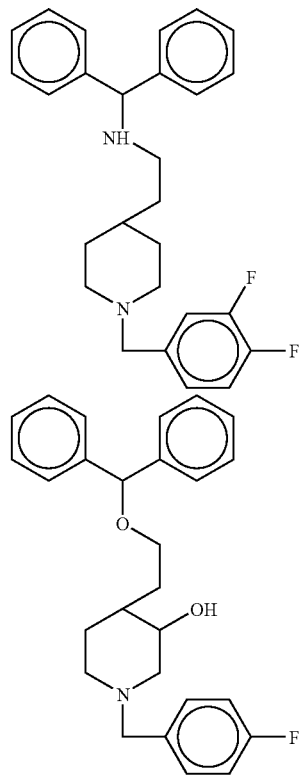

have been shown to provide unexpectedly low activity in the nanomolar range, as well as high selectivity as shown by the difference in binding affinities with respect to the DAT and SERT. In the foregoing formulae, each variant is considered as individually defined. The various replacement groups for X, and R through $R^5$ may be employed to the exclusion of any one or more than one of such replacements.

Further preferred classes of active compounds include those of structural Formula I where B is a phenyl group bearing a 4-cyano, 4-iodo, or 3,4-difluoro-group, and in particular, compounds falling within the scope of structural Formula I or its preferred subgeneric general formula, and corresponding to the following structures:

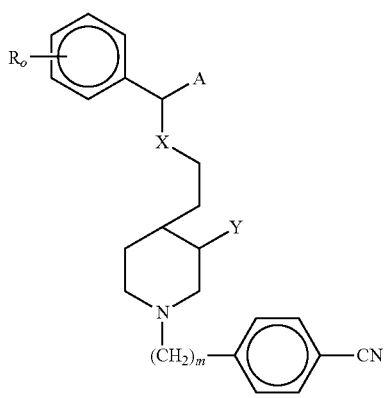
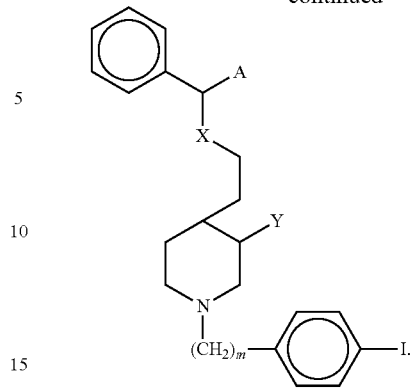
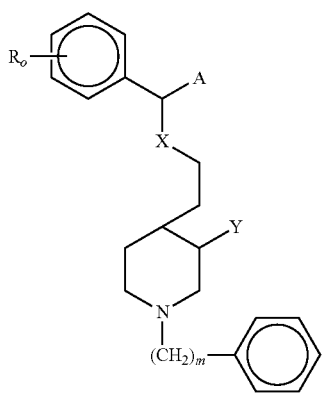
Most preferably, the active compounds of the invention correspond to compounds of the formula:
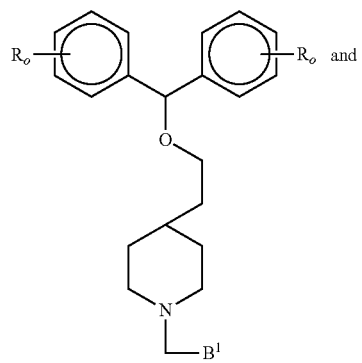
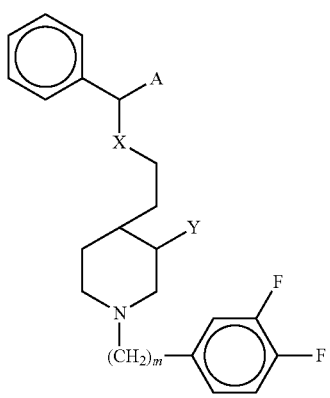
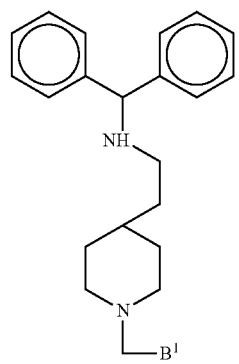
where $B^1$ is 4-cyanophenyl, 3,4-difluorophenyl, or 4-iodophenyl. In each of the more general structures above having a $-(CH_2)_m$ radical, when m is 2 or 3, any of the carbons of the $-(CH_2)_m$ moiety may be substituted by $-OR^7$ as defined above.

Further examples of preferred compounds include:
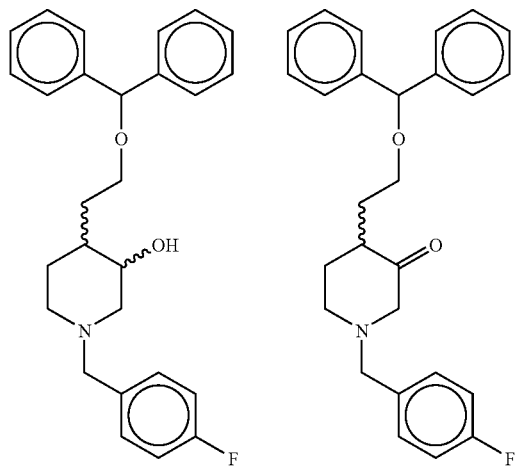
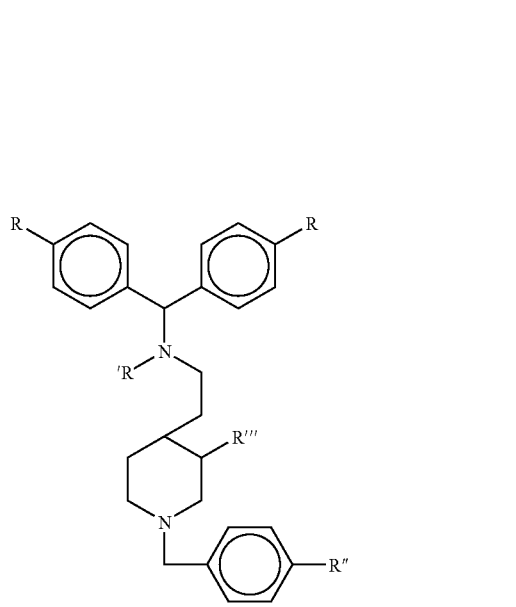
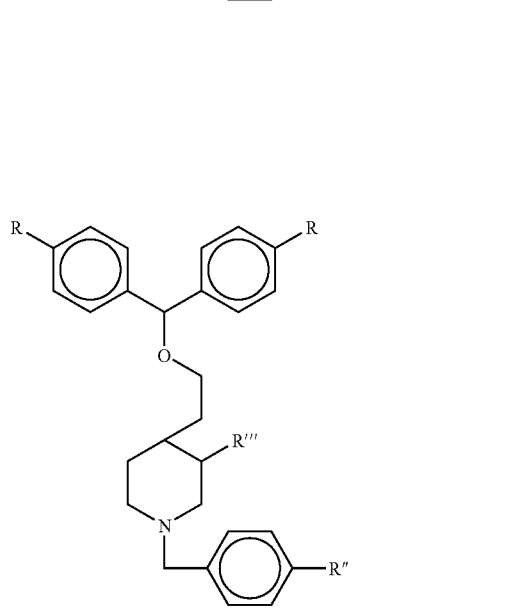
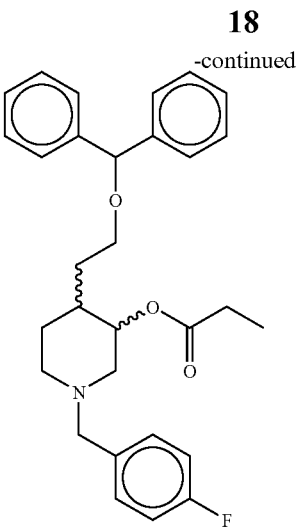
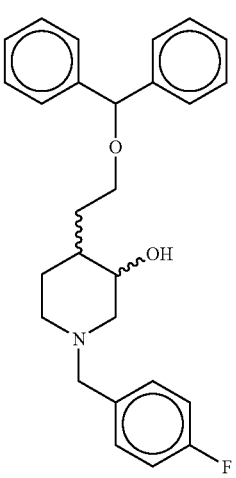 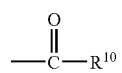
where R''' is H, OH, NH$_2$, OR$^9$, or NHR$^9$ where R$^9$ is
where R$^{10}$ is C$_{6-20}$ alkyl, and
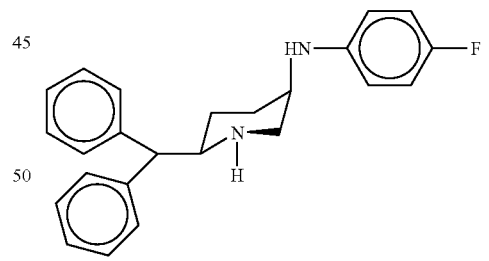
7a
cis-isomer
+
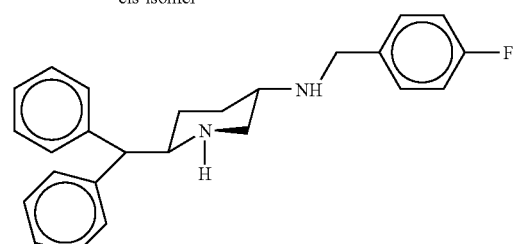
7b
trans-isomer Additional useful compounds are provided by the following formulae D-84. D-225, D-232, D-233, and D-276:

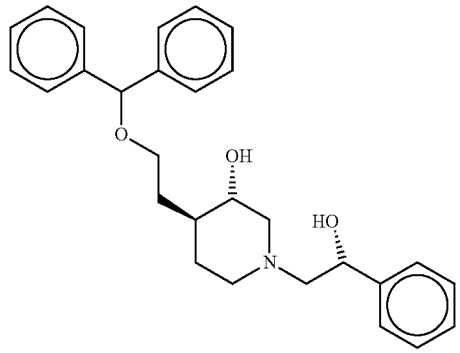
D-225

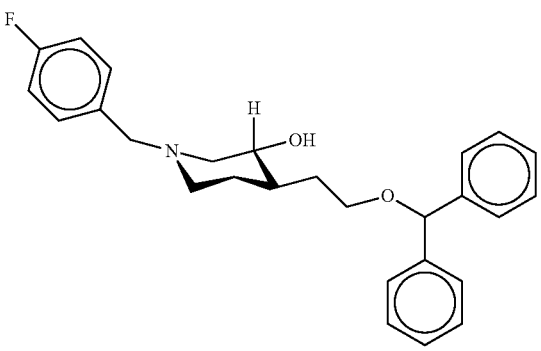
D-84

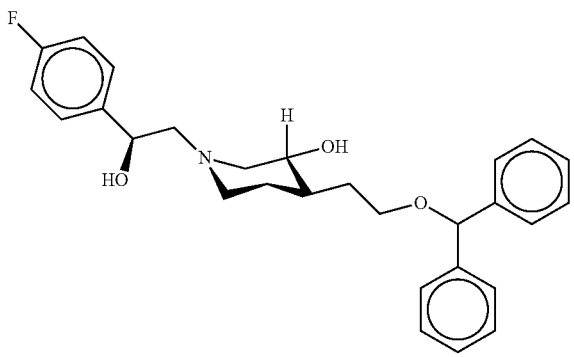
D-232

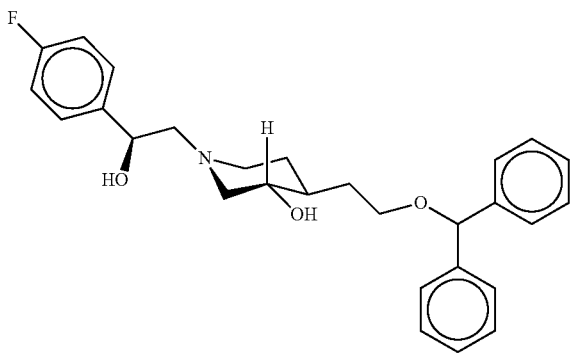
D-233

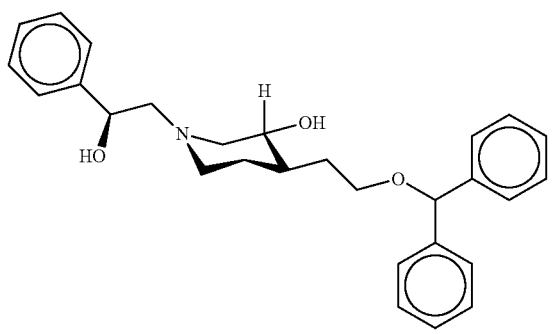
D-276

The compounds having formula D-84, D-225, D-232, D-233, and D-276 are made via the synthetic schema set forth in FIGS. 5A, 5B, 6, 7, 8, and 9.

In still another variation of the present invention, a compound having the following formula is provided:

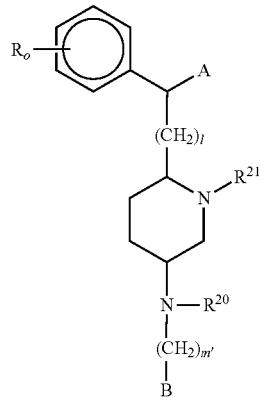

where all symbols are the same as those set forth above unless explicitly stated to be different. Specifically, A is

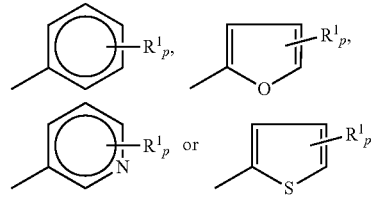

and B is

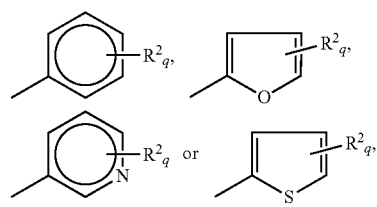

l is 0, 1, or 2, preferably 0 or 1, more preferably 0;
m is 1 or 2, preferably 1;

o is 0, 1, 2, 3, or 4, preferably 0, 1, or 2, most preferably 0 or 1;

p is 0, 1, 2, 3, or 4, preferably 0, 1, or 2, most preferably 0 or 1;

q is 0, 1, 2, or 3, preferably 0 or 1;

$Z^1$ is —H, —$NH_2$, —OH, =O, —Oalkyl (e.g. $C_{1-8}$), —Oaryl (e.g. $C_{6-16}$), or —O—C(O)—$R^5$;

R, $R^1$, and $R^2$ are selected from the group consisting of H, F, Cl, Br, I, CN, COOEt, OH, $NO_2$, $NH_2$, $OR^5$, wherein $R^5$ is $C_{1-8}$ alkyl, $C_{5-6}$ cycloalkyl, or $C_{2-8}$ alkenyl or $R^2$ is a 5 or 6 membered heterocycle: preferably a heterocycle selected from the group consisting of:

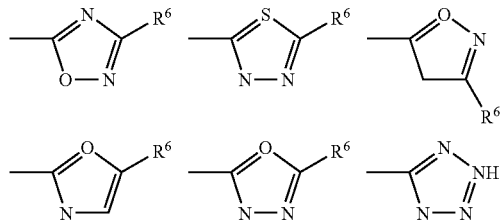

wherein $R^6$ may be $C_{1-4}$ alkyl, substituted or unsubstituted phenyl or naphthyl, it being understood that the hydroxyl group is not substituted onto an ethylenic carbon;

and where one or more $CH_2$ groups of —$(CH_2)_m$— are optionally substituted by $CR^7$, $R^{,7}$ (i.e., a methylene can be substituted with an $Z^1$ group as set forth above);

$R^7$ is H, —$O^{11}$, or —$NR^{11}$;

$R^{,7}$ is H, —$C_{1-8}$ alkyl or $R^7$, $R^{,7}$ are combined together as =O;

$R^{11}$ is H, $C_{1-8}$ alkyl $C_{2-8}$ alkylene, $C_{6-18}$ alkyl-aryl, or —$COOR^{12}$;

$R^{12}$ is $C_{1-8}$ alkyl, $C_{2-8}$ alkylene, or $C_{6-18}$ alkyl-aryl; and $R^{20}$ and $R^{21}$ are each independently hydrogen or a substituted or unsubstituted hydrocarbon group such as a $C_{1-10}$ alkyl. or a pharmaceutically acceptable salt or derivative thereof. In a variation, $R^{20}$ and $R^{21}$ are connected to form a ring as set forth for example in the following formula:

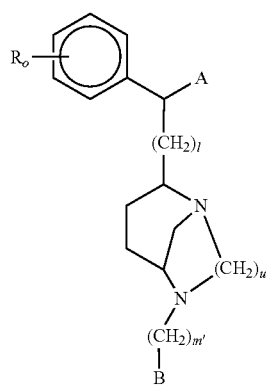

wherein u is 1, 2, or 3; preferably 2. More specific compounds of the present embodiment include the compounds represented by the following formulae

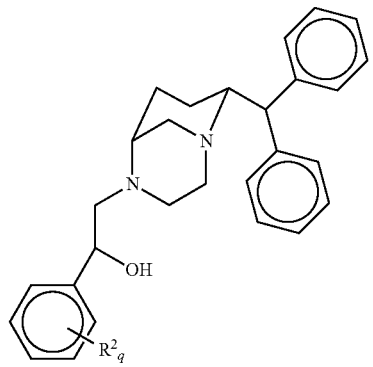

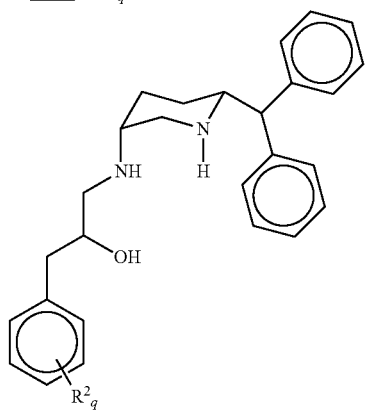

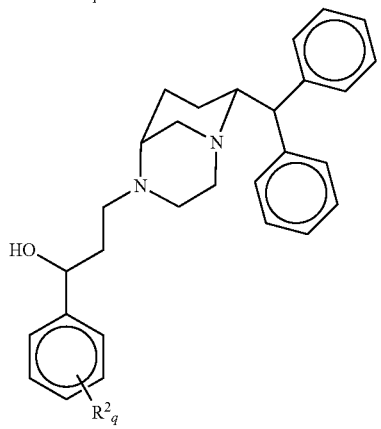

Figure 10:
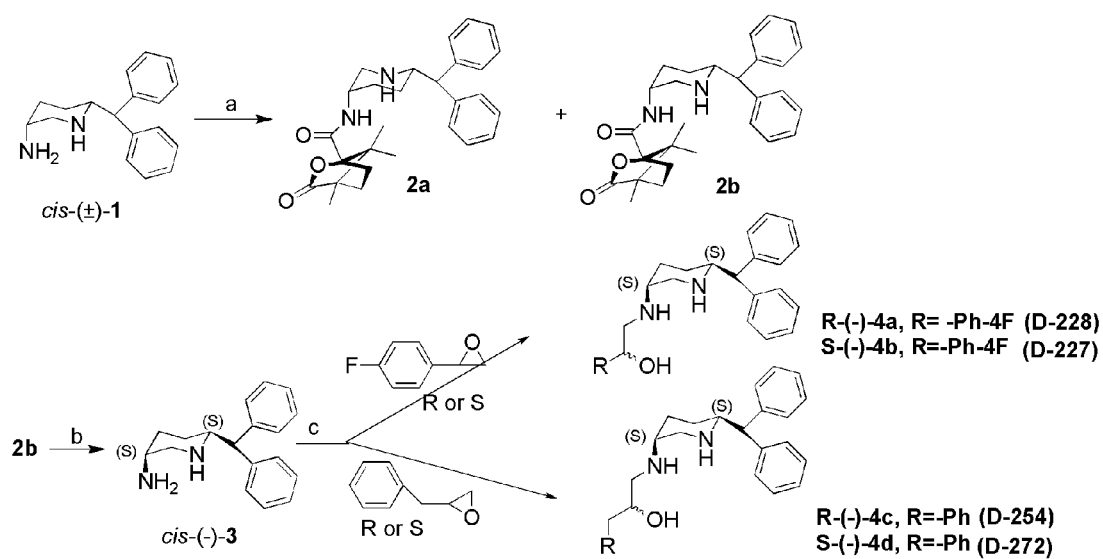
FIG. 10 illustrates another synthesis scheme and the structures of certain of the subject invention compounds.
Figure 11:
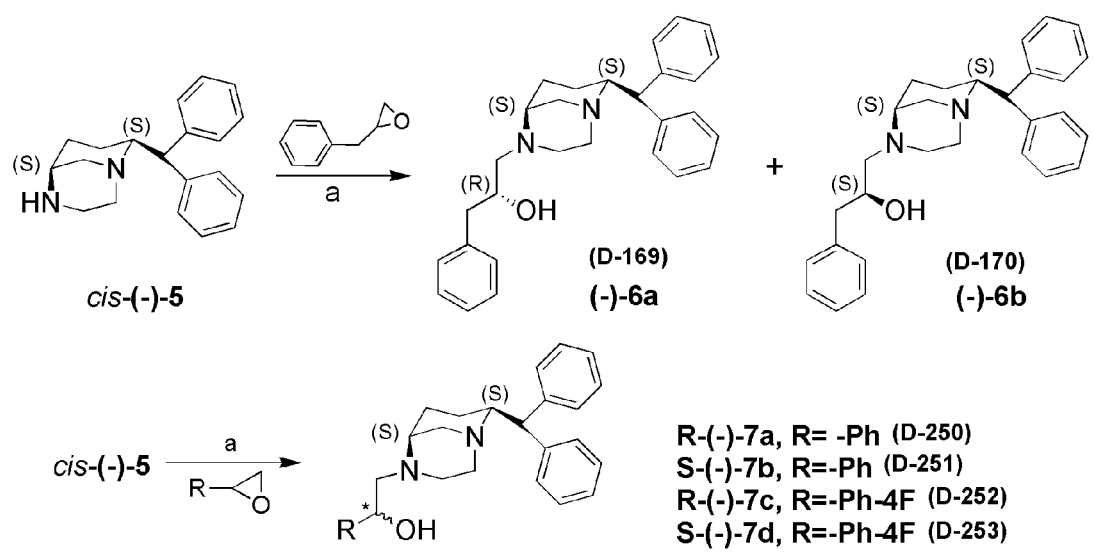
FIG. 11 illustrates another synthesis scheme and the structures of certain of the subject invention compounds.
Figure 12:
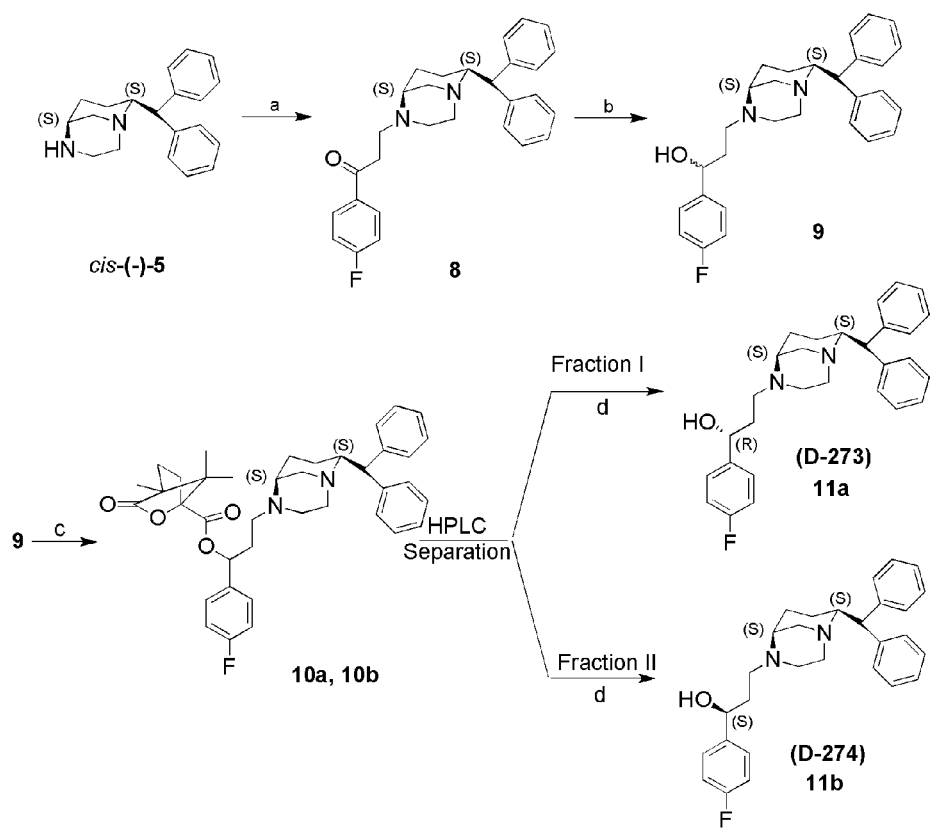
FIG. 12 illustrates another synthesis scheme and the structures of certain of the subject invention compounds.

Synthesis of target compounds of the present embodiment are shown in FIGS. 10, 11, and 12. FIG. 10 describes the synthesis of targets 4a to 4d. As described in an earlier publication, optically active cis-amine is synthesized from racemic 1 by converting the amine into diastereoisomeric intermediates followed by separation and hydrolysis of the desired isomers to the corresponding amine cis-(−)-3. (Kolhatkar, R. B.; Ghorai, S. K.; George, C.; Reith, M. E.; Dutta, A. K. Interaction of cis-(6-benzhydrylpiperidin-3-yl)benzylamine analogues with monoamine transporters: structure-activity relationship study of structurally constrained 3,6-disubstituted piperidine analogues of (2,2-diphenylethyl)-[1-(4-fluorobenzyl)piperidin-4-ylmethyl]amine. J Med Chem 2003, 46, 2205-15.) Treatment of (−)-3 with optically active epoxides furnished the final hydroxy targets 4a-4d in good yield. The optically active epoxides were synthesized by a published procedure. (Schaus, S. E.; Brandes, B. D.; Larrow, J. F.; Tokunaga, M.; Hansen, K. B.; Gould, A. E.; Furrow, M. E.; Jacobsen, E. N. Highly selective hydrolytic resolution of terminal epoxides catalyzed by chiral (salen)Co(III) complexes. Practical synthesis of enantioenriched terminal epoxides and 1,2-diols. J Am Chem Soc 2002, 124, 1307-15).

FIG. 11 describes the synthesis of targets 7a-7d. Optically active amine (−)-5 was synthesized by following our earlier procedure. (Kolhatkar, R.; Cook, C. D.; Ghorai, S. K.; Deschamps, J.; Beardsley, P. M.; Reith, M. E.; Dutta, A. K. Further structurally constrained analogues of cis-(6-benzhydrylpiperidin-3-yl)benzylamine with elucidation of bioactive conformation: discovery of 1,4-diazabicyclo[3.3.1]nonane derivatives and evaluation of their biological properties for the monoamine transporters. J Med Chem 2004, 47, 5101-13). This amine was treated with racemic 2,3-epoxypropyl benzene, which produced two diastereomers 6a and 6b, which were separated by column chromatography. Amine cis-(−)-5 was further treated with enantiomeric (R and S) 2-phenyloxirane and 2-(4-fluorophenyl)oxirane separately in ethanol to yield the target compounds 7a-7d in reasonably good yield.

FIG. 12 describes the synthesis of targets 11a and 11b. N-alkylation of amine cis-(−)-5 with 3-chloro-4'-fluoro propiophenone under basic condition produced 8 which was reduced by sodium borohydride to produce mixture of both R- and S-alcohols 9. Alcohol 9 was next converted into diastereomeric caphanic esters, which were separated by semi-preparative HPLC process. The final targets, 11a and 11b, were produced after hydrolyzing the esters.

All the various geometric and stereoisomers of the subject invention compounds are useful. However, some geometric and stereoisomers have unexpectedly high activity or differential activities. One example of the latter is represented by the cis- and trans-isomers of 2-diphenylmethyl-5-(4-fluorobenzylamino)piperidine, prepared in racemic form. The cis isomer showed a selectivity ratio of 93.7 SERT/DAT, while the trans isomer showed a 6.28 selectivity ratio. Individual enantiomers are expected to exhibit yet higher activity and selectivity.

Having generally described this invention, a further understanding can be obtained by reference to certain specific examples which are provided herein for purposes of illustration only and are not intended to be limiting unless otherwise specified.

Target compounds are prepared as free bases or salts, e.g. hydrochloride, hydrobromide, oxalate, tartrate, etc. Characterization of the compounds is carried out using standard high field NMR, mass spectra, optical rotation, etc. Purity of the compounds are measured by elemental analysis, TLC or HPLC. A purity of >98% is preferred for the biological analysis of these compounds.

The rat DAT was labeled with [$^3$H]Win 35,428 and the rat SERT with [$^3$H]citalopram. Both binding assays were carried out under the same conditions with striatal tissue from male, young adult Sprague-Dawley rats, as described in M. E. A. Reith et al., "Structural Requirements for Cocaine Congeners to Interact With Dopamine and Serotonin Uptake Sites in Mouse Brain and to Induced Stereotyped Behavior", BIOCHEM. PHARMACOL., 1986, 35, 1123-1129 and A. K. Dutta et al., "Structure-Activity Relationship Studies of Novel 4-[2-[Bis (4-fluorophenyl)methoxy]ethyl]-1-(3-phenylpropyl)piperidine Analogs: Synthesis and Biological Evaluation at the Dopamine and Serotonin Transporter Sites", J. MED. CHEM., 1996, 39, 749-756. Briefly, rat striatal membranes were incubated with radioligand and inhibitor for 2 h on ice in a sodium phosphate buffer at a final Na$^+$ concentration of 30 nM, pH 7.4, at room temperature. The assays were terminated by filtration through glass fiber filtermats (Wallac, Inc., Gaithersburg, Md.), presoaked in 0.05% (v/v) polyethyleneimine, with a MACH3-96 Tomtec harvester (Wallac, Inc.). Filters were assayed for radioactivity in a Microbeta Plus liquid scintillation counter (Wallac, Inc.).

Uptake of [$^3$H]dopamine into HEK-293-hDAT cells was measured in suspended, intact cells by general techniques previously described. M. C. Ritz et al., "Cocaine Inhibition of Ligand Binding at Dopamine, Norpinephrine and Serotonin Transporters: A Structure-Activity Study", LIFE. SCI., 1990, 46, 635-645; M. J. Kaufman et al., SYNAPSE, 1991, 9, 43-49. Briefly, cells were preincubated with inhibitor for 15 minutes at room temperature in the same tropolone-containing buffer as described above; [$^3$H]dopamine was added and the incubation continued for another 8 minutes. Termination of the assay consisted of addition of ice-cold buffer and rapid filtration through Whatman GF/C glass fiber filters, presoaked in 0.05% (w/v) poly-L-lysine, with a Brandel 24-pin harvester (Brandel, Inc. Gaithersburg, Md.). Radioactivity on filters was estimated by liquid scintillation counting (Beckman LS6000IC, Beckman Instruments, Inc., Fullerton, Calif.).

All compounds were dissolved in dimethylsulfoxide (DMSO) and diluted to 10% (v/v) DMSO. Additions from the latter stocks resulted in a final concentration of DMSO of 0.5%, which by itself did not interfere with radioligand binding or uptake. After initial range-finding experiments, at least five concentrations of the test compound were studied, spaced evenly around its $IC_{50}$ value. The latter was estimated by non-linear computer curve fitting procedures as described previously.

The DAT, SERT, and NET activities for these compounds make them useful in numerous ways. For example, radioligand version of these disclosed compounds will find applications as imaging agents for DAT in the CNS for SPECT and PET imaging studies. Such imaging may be used in diagnosing Parkinson's disease.

In addition, the compounds may serve as ligands for the DAT, SERT, and NET for use as comparative or base ligands when testing new candidate CNS drugs. Most importantly, however, the compounds of the subject invention, as shown by their binding affinities at low concentration, will have utility in treating CNS disorders such as drug addiction, particularly the effects of cocaine and PCP administration, and potentially the effects of administration of other psychoactive drugs, both legal and illicit. The compounds may be used to treat cocaine addiction, for example. The subject compounds also show utility, based on the in vitro studies described herein, for administration to patients suffering from Parkinson's disease and other related disorders. The compounds further have utility as antidepressants, and in treating other neurological disorders related to those above.

The studies performed to date and disclosed herein thus support the use of the presently claimed compounds in the treatment of CNS disorders in mammalian species, particularly in humans. The effective dosage will vary depending upon the particular disorder being treated. In general, the administration will be such that a concentration will be present in brain tissue and/or fluids which cause measurable binding to the DAT, SERT, or NET. This binding may be assessed by traditional techniques, including using radiolabeled compounds of the present invention or by using the compounds of the present invention to displace other radiolabeled ligands. Conventional techniques such as SPECT and PET may be used in assaying binding.

In general, the concentration of the compounds in the blood or plasma should range from about 1% of the $IC_{50}$ concentration for the respective transporter, as measured herein, to about 1000% of this concentration, more preferably from 5% to 400%, yet more preferably from 10% to 200%.

The administration may be in any pharmaceutically acceptable form, for example as a liquid containing the active compound dissolved in a suitable solvent or dispersed or emulsified in a liquid; intravenously; as a solid in tablet or capsule form; parenterally as an injected liquid, or transdermally from a transdermal patch. Each formulation may contain usual pharmaceutically acceptable additives, including but not limited to flavorants, odorants, tabletting aids, solubility enhancers, permeability enhancers, surfactants, fillers, etc. In addition, the compounds may be reacted with suitable salt formers of their pharmaceutically acceptable salts, including but not limited to acetates, formates, oxalates, tartrates, hydrochlorides, hydrobromides, hydrogen sulfates, etc.

The expected useful dosage when administered orally is from to 0.01 mg to 100 mg per kilogram of body weight, more preferably from 0.1 mg to 50 mg, yet more preferably 0.2 mg to 30 mg. Total dosage for the average adult may range from 5 mg to 500 mg, preferably 10 mg to 250 mg, and most preferably 10 mg to 150 mg. The actual dosage can be determined readily by conventional methodology.

Target compounds are prepared as free bases or salts, e.g. hydrochloride, hydrobromide or oxalate. Characterization of the compounds is carried out using standard high field NMR, mass spectra, optical rotation, etc. Purity of the compounds are measured by elemental analysis, TLC or HPLC. A purity of >98% is preferred for the biological analysis of these compounds. Several general synthetic pathways have been used herein. Other synthetic methods well known to the synthetic organic chemist may be used to prepare the compounds of the subject invention, or to derivatize these compounds.

I Synthesis of Intermediates 1-(Methoxycarbonyl)-4-[(2-Diphenylmethoxy)ethyl] piperidine The solution of 4-[2-(Diphenylmethoxy)ethyl]-1-(phenylmethyl)piperidine (4.62 g, 11.82 mmol) and methyl chloroformate (2.60 g, 23.53 mmol) in benzene (60 ml) was refluxed for 6 hours. After T. L. C. showed the completion of reaction, the solvent was removed under vacuo to give a viscous liquid 1-(methoxycarbonyl)-4-[(2-diphenylmethoxy)ethyl]piperidine, 4.17 g (99% yield).
$^1$H NMR (CD$_3$Cl) δ 7.34-7.18 (10H, m, Ar—H), 5.30 (1H, s, Ph$_2$CHO), 3.67 (3H, s, OCH$_3$), 3.50-3.46 (2H, t, J=6.0 Hz, OCH$_2$), 2.77-2.68 (2H, t, J=12.3 Hz, N(CH)$_2$), 2.62-2.54 (2H, t, J=12.0 Hz, N(CH)$_2$), 1.67-1.57 (5H, m), 1.26-1.07 (2H, m).

4-[(2-Diphenylmethoxy)ethyl]piperidine 1-(methoxycarbonyl)-4-[(2-diphenylmethoxy)ethyl]piperidine (4.17 g, 11.81 mmol) was dissolved in ethanol (100 ml), KOH (2.5 g) was added into the solution. The reaction solution was refluxed for 3 days. The solvent was evaporated and EtOAc was added. The EtOAc solution was washed by brine, dried over Na$_2$SO$_4$, and evaporated to give a crude product, which was purified by chromatography (EtOAc/MeOH/Et$_3$N=100/5/2) to give a white solid 4-[(2-diphenylmethoxy)ethyl]piperidine, 2.80 g (80% yield). $^1$H NMR (CD$_3$Cl) δ 7.35-7.19 (10H, m, Ar—H), 5.31 (1H, s, Ph$_2$CHO), 3.50-3.46 (2H, t, J=6.0 Hz, OCH$_2$), 3.08-3.04 (2H, bd, J=2.3 Hz, N(CH)$_2$), 2.77-2.68 (2H, t, J=12.6 Hz), 2.62-2.54 (2H, t, J=12.3 Hz, N(CH)$_2$), 1.82-1.57 (5H, m), 1.14-1.02 (2H, m). Anal. [C$_{20}$H$_{25}$NO.2.0H$_2$O] Calculated: C, 79.90; H, 8.58; N, 4.66; Found: C, 79.86; H, 8.59; N, 4.70.

N-Benzhydryloxyphthalimide

A solution of 1-chloro-1,1-diphenylmethane (3.42 g, 16.93 mmol), N-hydroxyphthalimide (2.30 g, 14.11 mmol) and Et$_3$N (3.0 ml) in DMF (50 ml) was stirred at 60° C. under N$_2$ for 8 hours. After the reaction mixture was cooled to room temperature, water (100 ml) was added. The mixture was extracted with Et$_2$O. The combined organic phase was dried over N$_2$SO$_4$. After evaporation of the solvent, the crude product was purified by chromatography (Hexane/Benzene/EtOAc=20/10/3) to give a white solid, 3.95 g (85% yield). $^1$H NMR (CD$_3$Cl) δ 7.72-7.63 (1H, m), 7.56-7.53 (1H, m), 7.40-7.24 (12H, m), 5.85 (1H, s, Ph$_2$CH).

O-Benzhydrylhydroxylamine

N-Benzhydryloxyphthalimide (1.03 g, 3.14 mmol) was dissolved in EtOH (20 ml). NH$_2$NH$_2$ (0.3 ml) was added into the EtOH solution. After the reaction mixture was stirred at room temperature for 0.5 h., EtOH was removed under vacuo and EtOAc (60 ml) was added. The mixture was filtered. The solution was collected and dried over Na$_2$SO$_4$. After the evaporation of solvent, the crude product was purified by chromatography (Hexane/EtOAc=5/1) to give a viscous oil 0.31 g (50% yield). $^1$H NMR (CD$_3$Cl) δ 7.34-7.26 (10H, m, AR-H), 5.65 (1H, s, Ph$_2$CH).

1-[(4-Fluorophenyl)methyl]-4-piperidinemethanol

Dry THF (50 ml) was added dropwise into lithium aluminum hydride (0.7 g) under N$_2$ in ice bath. 1-[(4-Fluorophenyl)methyl]-4-(ethoxycarbonyl)piperidine (1.21 g, 4.57 mmol) in dry THF (10 ml) was added dropwise into the LAH suspension solution. The reaction mixture was refluxed for 2 hours. Saturated NaOH/H$_2$O (3 ml) was added dropwise and the reaction cooled by an ice bath. The mixture was filtered. The solution was dried over Na$_2$SO$_4$ and evaporated to produce 11 0.98 g (98% yield). $^1$H NMR (CD$_3$Cl) δ 7.36-7.26 (2H, m, Ar—H), 7.07-6.96 (2H, m, Ar—H), 4.66 (1H, s, OH), 3.50-3.48 (2H, d, J=6.0 Hz, CH$_2$OH), 3.46 (2H, s, F-PhCH$_2$), 2.90-2.87 (2H, bd, J=11.1 Hz, N(CH)$_2$), 1.99-1.91 (2H, dt, J=1.8, 11.8 Hz, N(CH)$_2$), 1.73-1.68 (3H, m), 1.34-1.22 (2H, m).

1-[(4-Fluorophenyl)methyl]-4-piperidinecarboxaldehyde

A solution of oxylyl chloride (0.59 ml, 3.95 mmol) in CH$_2$Cl$_2$ (20 ml) was cooled to −78° C. DMSO (0.95 ml, 13.38 mmol) was added dropwise into the oxylyl chloride solution. The reaction mixture was stirred for 5 minutes, and 1-[(4-fluorophenyl)methyl]-4-piperidinemethanol (0.99 g, 4.46 mmol) in CH$_2$Cl$_2$ (20 ml) was added dropwise into the reaction solution. Stirring was continued for an additional 20 minutes. Et$_3$N, 8.0 ml was added and the reaction mixture was stirred for 10 minutes and then allowed to warm to room temperature. Water (50 ml) was added and the mixture was extracted with CH$_2$Cl$_2$. The combined CH$_2$Cl$_2$ solution was dried over N$_a$SO$_4$. The evaporation of solvent gave an oil, 0.77 g (79% yield).
$^1$H NMR (CD$_3$Cl) δ 9.65 (1H, s, CHO), 7.30-7.24 (2H, m, Ar—H), 7.00-6.97 (2H, m, Ar—H), 3.46 (2H, s, p-FPhCH$_2$), 2.81-2.76 (2H, m, N(CH)$_2$), 2.30-2.20 (1H, m, CHCHO), 2.14-2.06 (2H, dt, J=2.1, 11.3 Hz, N(CH)$_2$), 1.92-1.86 (2H, dd, J=3.5, 13.5 Hz), 1.74-1.62 (2H, m).

4-[(2-Diphenylethyl)aminocarbonyl]-1-[(4-fluorophenyl)methyl]piperidine

1-[(4-Fluorophenyl)methyl]-4-(ethoxycarbonyl)piperidine (0.68 g, 2.72 mmol) was converted into its carboxylic acid, which was then reacted with 2,2-diphenylethyl amine (0.67 g, 3.40 mmol), EDCI (0.76 g, 3.95 mmol), and HOBT (0.62 g, 4.59 mmol) to produce 4-[(2-diphenylethyl)aminocarbonyl]-1-[(4-fluorophenyl)methyl]piperidine, 0.84 g (75% yield)(procedure D). $^1$H NMR (CD$_3$Cl) δ 7.36-7.20 (12H, m, Ar—H), 7.01-6.95 (2H, m, Ar—H), 5.39 (1H, bs, NH), 4.21-4.15 (1H, t, J=7.8 Hz, Ph$_2$CH), 3.91-3.86 (2H, t, J=7.5 Hz, CH$_2$NH), 3.41 (2H, s, p-FPhCH$_2$), 2.84-2.80 (2H, d, J=11.4 Hz, N(CH$_2$)$_2$), 1.96-1.87 (3H, m, NHCOCH, NH(CH)$_2$), 1.65-1.58 (4H, m).

4-[(Bis(4-fluorophenyl)ethylamino)carbonyl-1-(phenylethyl)piperidine 1-(phenylethyl)-4-(ethoxycarbonyl)piperidine (0.25 g, 0.95 mmol) was converted into its carboxylic acid, which was then reacted with bis(4-fluorophenyl)methyl amine (0.25 g, 1.14 mmol), EDCI (0.25 g, 1.27 mmol), HOBT (0.20 g, 1.48 mmol) in Et$_3$N (1.5 ml) and CH$_2$Cl$_2$ (20 ml) to produce 4-[(bis(4-fluorophenyl)ethylamino)carbonyl-1-(phenylethyl)piperidine, 0.32 g (74% yield)(procedure E). $^1$H NMR (CD$_3$Cl) δ 7.29-7.03 (10H, m, Ar—H), 7.05-6.99 (3H, m, Ar—H), 6.22-6.20 (1H, d, J=7.8 Hz), p-FPh$_2$CH), 6.00-5.97 (1H, d, J=7.5 Hz, NH), 3.08-3.04 (2H, bd, J=11.4 Hz, N(CH$_2$)$_2$), 2.83-2.78 (2H, d), 2.62-2.57 (2H, m), 2.25-2.15 (1H, m, NCOCH), 2.10-2.03 (2H, t, J=11.4 Hz, N(CH$_2$)$_2$), 1.96-1.81 (4H, m).

4-[(1-Phenylethyl)aminocarbonyl]methyl-1-[(4-fluorophenyl)methyl]piperidine

1-[(4-fluorophenyl)methyl]-4-[(ethoxycarbonyl)methyl]piperidine (0.55 g, 1.97 mmol) was refluxed in CF$_3$CO$_2$H/HCl/H$_2$O (1:1:1) 10 ml to give the corresponding acid, which was then reacted with 1-phenylethylamine (0.29 g, 2.40 mmol), EDCI (0.56 g, 2.97 mmol) and HOBT (0.40 g, 2.96 mmol) in CH$_2$Cl$_2$ (10 ml) to produce a solid, 0.33 g (50% yield)(procedure D). $^1$H NMR (CD$_3$Cl) δ 7.35-7.23 (7H, m, Ar—H), 7.00-6.94 (2H, t, J=8.4 Hz, Ar—H), 5.83-5.80 (1H, bd, J=7.5 Hz, NH), 5.15-5.10 (m, 1H, PhCHMe), 3.42 (s, 2H, p-PhCH$_2$N), 2.83-2.78 (m, 2H, N(CH)$_2$), 2.07-2.05 (2H, d, J=7.2 Hz, CH$_2$CO), 1.99-1.89 (2H, m), 1.86-1.78 (1H, m), 1.71-1.61 (2H, t, J=15 Hz), 1.48-1.45 (3H, d, J=6.9 Hz, Me), 1.33-1.21 (2H, m).

Synthesis of 2-(Diphenylcyanomethyl)-5-nitropyridine

To a mixture of 1.0 g 2-chloro-5-nitropyridine (6.3 mmol), 1.33 g diphenylacetonitrile (6.9 mmol, 1.1 equiv) and 700 mg tetrabutylammonium fluoride (3.15 mmol, 0.5 equiv) in 3 mL toluene was added dropwise 1.5 mL 50% aqueous NaOH. After 30 min, no starting materials remained by TLC (hexane/EtOAc). The mixture was filtered through a short plug of silica to remove tars, evaporated and chromatographed (SiO$_2$; hexane/EtOAc). The crude product was a slightly yellow oil which was recrystallized from MeOH to furnish the title compound (1.7 g, 86%) as colorless plates. mp 94-9° C. $^1$H NMR (CDCl$_3$; 300 MHz) 7.20-7.29 (5H, m), 7.35-7.42 (5H, m), 7.54 (1H, d, J=8.7 Hz, H-3), 8.49 (1H, dd, J=3 and 9 Hz, H-4), 9.60 (1H, d, J=2.4 Hz, H-6). $^{13}$C NMR (CDCl$_3$; 300 MHz) 60.19, 121.65, 123.77, 128.87, 129.09, 129.33, 132.52, 138.46, 143.49, 145.31, 164.99. Elemental analysis calculated for C$_{19}$H$_{13}$N$_3$O$_2$: C, 72.38; H, 4.13; N, 13.33. Found: C, 72.35; H, 4.08; N, 13.25.

Synthesis of 2-(Diphenylacetamidomethyl)-5-nitropyridine

A mixture of 5.0 g 2-(diphenylcyanomethyl)-5-nitropyridine (15.8 mmol) was added to a magnetically-stirred, room temperature solution of 40 mL conc. H$_2$SO$_4$ diluted with 10 mL H$_2$O. The mixture was then heated to 90° C. until all starting material consumed by TLC (~2 hr). The dark solution was then poured onto crushed ice and water and stirred for 1 hr, the crude title compound precipitates. The mixture was extracted thrice with EtOAc and these were pooled, dried (MgSO$_4$, with filtration through short plug of Celite) and evaporated. Dry-column chromatography (silica; hexane/EtOAc/MeOH) furnished the title compound (4.74 g, 90%) as a amorphous tan solid. mp 160-4° C. $^1$H NMR (CDCl$_3$; 300 MHz) 5.9 (1H, bs, NH), 7.05-7.1 (4H, m, ArH), 7.26 (1H, d, J=2.4 and 6.3 Hz, H-4), 9.43 (1H, d, J=1.8 Hz, H-6. $^{13}$C NMR (CDCl$_3$; 400 MHz) 126.78, 128.02, 128.64, 130.25, 131.68, 142.09, 143.43, 169.44, 173.99. Elemental analysis calculated for C$_{19}$H$_{15}$N$_3$O$_3$; C, 68.47; H, 4.50; N, 12.61. Found: C, 68.49; H, 4.55; N, 12.60.

Synthesis of Diphenyl-(5-amino-2-pyridyl)acetamide

A mixture of 8.86 g of diphenyl-(5-nitro-2-pyridyl)acetamide (26.5 mmol) in 50% EtOH/glacial AcOH with 100 mg platinum (IV) oxide was shaken on a Parr hydrogenator (30 psi H$_2$) for 3 hr. The mixture was filtered through a bed of Celite, then the ethanol was evaporated under reduced pressure. The mixture was then basified with K$_2$CO$_3$ and extracted with EtOAc (4×), dried (MgSO$_4$), filtered through Celite again and evaporated. The remaining solid was recrystallized from hexane/EtOAc/MeOH to furnish the title compound (7.9 g, 98%) as a tan crystal. mp 215-20° C. $^1$H NMR (CDCl$_3$; 300 MHz) δ 3.85 (2H, bs, NH), 5.88 (1H, bs, CONH), 6.54 (1H, d, J=8.4 Hz), 6.84 (1H, dd, J=3 and 8.7 Hz), 7.01-7.06 (4H, m), 7.24-7.32 (6H, m), 8.11 (1H, d, J=2.4 Hz, H-6), 9.57 (1H, bs, CONH). Elemental analysis calculated for C$_{19}$H$_{17}$N$_3$O.0.25H$_2$O: C, 74.15; H, 5.69; N, 13.67. Found: C, 74.06; N, 5.69; H, 13.78.

Synthesis of 2-Diphenylmethyl-5-aminopyridine

A mixture of 5.28 g diphenylmethyl-(5-amino-2-pyridyl)acetamide (17.4 mmol) and 150 mL 37% HCl under a N$_2$ atmosphere was refluxed until all starting material was consumed by TLC (~18 hr). The mixture was then cooled and poured into 300 g ice and H$_2$O and basified with K$_2$CO$_3$. The mixture was extracted thrice with EtOAc (150 mL), dried (MgSO$_4$) and evaporated to a green oil that solidified. This was chromatographed (SiO$_2$; hexane/EtOAc) to furnish the title compound (4.09 g, 90%) as a tan crystalline solid. mp 130-4° C. $^1$H NMR (CDCl$_3$; 300 MHz) δ 3.52 (2H, bs, NH), 5.61 (1H, s, CH(C$_6$H$_5$)$_2$), 6.83-6.91 (2H, m, ArH), 7.15-7.32 (10H, m, ArH), 8.08 (1H, d, J=2.4 Hz, H-6). $^{13}$C NMR (CDCl$_3$; 300 MHz) 58.61, 122.38, 123.98, 126.55, 128.57, 129.56, 137.31, 140.77, 143.64, 153.39. Elemental analysis calculated for C$_{18}$H$_{16}$N$_2$; C, 83.08; H, 6.15; N, 10.77. Found: C, 82.82; H, 6.30; N, 10.81.

Synthesis of racemic cis- and trans-2-Diphenylmethyl-5-aminopiperidine

To a solution of 454 mg 2-diphenylmethyl-5-aminopyridine dihydrochloride salt (3.83 mmol) and 20 mL MeOH was added 50 mg platinum (IV) oxide and the mixture was shaken at room temperature under a $H_2$ atmosphere (60 psi) for 10 hr. The mixture was then filtered through Celite and the MeOH was evaporated. The remaining residue was diluted with saturated $K_2CO_3$ and extracted with $CH_2Cl_2$ (5×). The extracts were pooled, dried ($MgSO_4$) and evaporated to a colorless oil. The oil was chromatographed ($SiO_2$; $CH_2Cl_2$/MeOH/triethylamine) to furnish 300 mg (82%) of the title compounds as a colorless oil. The oil solidified upon addition of $EtO_2$. A sample of this mixture of diastereomers was separated by PTLC ($SiO_2$; hexanes/EtOAc/MeOH). Eluting first: racemic cis-2-diphenylmethyl-5-aminopiperidine, $^1$H NMR ($CDCl_3$; 400 MHz) δ 1.35-1.45 (2H, m, H-3), 1.55-1.65 (2H, m, H-4), 2.08 (3H, bs, NH), 2.77-2.82 (2H, s, H-6) 3.0 (1H, m, $\Sigma^3$J=13 Hz, H-5eq), 3.25 (1H, dt, $^3$J=4.0 and 8.8 Hz, H-2ax), 3.81 (1H, d, $^3$J=10.4 Hz, $CH(C_6H_5)_2$), 7.1-7.4 (10H, m, ArH). Eluting second: racemic trans-2-diphenylmethyl-5-amainopiperidine, $^1$H NMR ($CDCl_3$; 400 MHz) δ 1.1-1.25 (2H, m, H-3ax, H-4ax), 1.55-1.6 (1H, m, H-3eq), 1.9-1.96 (1H, m, H-4eq), 2.13 (3H, bs, NH), 2.35 (1H, t, $^2$J and $^3$J=10.8 Hz, H-6ax), 2.85 (1H, m, $\Sigma^3$J=38 Hz, H-5ax), 3.11 (1H, d, $^2$J=9.2 Hz, H-6eq), 3.19 (1H, t, $^3$J=10.8 Hz, H-2ax), 3.69 (1H, d, $^3$J=10 Hz, $CH(C_6H_5)_2$), 7.15-7.4 (10H, m, ArH). The $^1$H NMR ($CDCl_3$; 400 MHz) of the purified, unseparated mixture of the title compounds showed the ratio of 60 cis:40 trans based on integration ($CH(C_6H_5)_2$).

II. Examples of FIGS. 1 Through 4

Example 1

4-[2-(Diphenylmethoxy)ethyl]-1-[(3-fluorophenyl)methyl]piperidine

A mixture of 4-[(2-Diphenylmethoxy)ethyl]piperidine 4 (58 mg, 0.19 mmol), 3-fluorobenzyl chloride (51 mg, 0.35 mmol), $Et_3N$ (0.5 ml), and anhydrous $K_2CO_3$ (0.3 g) in DMF (10 ml) was stirred at 65° C. overnight. The reaction mixture was diluted with 30 ml water and extracted with $Et_2O$. The combined organic phase was dried over $Na_2SO_4$ and evaporated to give a crude product, which was purified by chromatography (EtOAc/Hexane=1/3) to give 4-[2-(diphenyl-methoxyethyl]-1-[(3-fluorophenyl)methyl]piperidine, a viscous liquid 62 mg (79% yield) ("Procedure A"). $^1$H NMR ($CD_3Cl$) δ 7.34-7.20 (10H, m, 2Ph), 7.11-7.03 (3H, m, m-FPh), 6.95 (1H, m, m-FPh), 5.31 (1H, s, $Ph_2CH$), 3.45-3.44 (2H, t, J=6.6 Hz, $OCH_2$), 3.44 (2H, s, m-FPh$CH_2$), 2.84-2.80 (2H, bd, J=1.1 Hz, $N(CH)_2$), 1.97-1.89 (2H, t, J=11.4 Hz, $N(CH)_2$), 1.63-1.51 (4H, m), 1.49-1.44 (1H, m), 1.29-1.21 (2H, m). The free base was converted into its oxalate salt, m.p.=150-151° C. Anal. [$C_{27}H_{30}NOF.(COOH)_2.0.3H_2O$] Calculated: C, 69.79; H, 6.58; N, 2.80. Found: C, 69.87; H, 6.80; N, 2.76.

Example 2

4-[2-(Diphenylmethoxy)ethyl]-1-[(3,4-difluorophenyl)methyl]piperidine

4-[(2-Diphenylmethoxy)ethyl]piperidine 4 (0.12 g, 0.42 mmol) was reacted with (3,4-difluoro)benzyl bromode (0.17 g, 0.82 mmol), $Et_3N$ (0.5 ml), and $K_2CO_3$ (0.6 g) in dry DMF (10 ml) to give 4-[2-(diphenylmethoxy)ethyl]-1-[(3,4-difluorophenyl)methyl]piperidine, 0.15 g (86% yield), as a viscous liquid (procedure A). $^1$H NMR ($CD_3Cl$) δ 7.34-6.99 (13H, m, Ar—H), 5.31 (1H, s, $Ph_2CH$), 3.49-3.45 (2H, t, J=6.3 Hz, $OCH_2$), 3.85 (s, 2H, $NCH_2Ph$), 2.80-2.77 (2H, d, J=11.4 Hz, $N(CH)_2$), 1.95-1.87 (2H, t, J=11.4 Hz, $N(CH)_2$), 1.63-1.55 (4H, m), 1.50-1.42 (1H, m), 1.28-1.15 (2H, m). The free base was converted into its oxalate salt, m.p.=158-159° C. Anal. [$C_{27}H_{29}NOF_2.(COOH)_2$] Calculated: C, 68.07; H, 6.11; N, 2.73; Found: C, 68.18; H, 6.13; N, 2.73.

Example 3

4-[2-(Diphenylmethoxy)ethyl]-1-[((4-trifluoromethyl)phenyl)methyl]piperidine 4-[(2-Diphenylmethoxy)ethyl]piperidine 4 (0.1 µg, 0.37 mmol) was reacted with (4-trifluoromethyl)benzyl chloride (0.14 g, 0.72 mmol), $Et_3N$ (0.5 ml) and $K_2CO_3$ (0.5 g) in DMF (10 ml) to give 4-[(diphenylmethoxy)ethyl]-1-[((4-trifluoromethyl)phenyl)methyl]piperidine, 0.15 g (92% yield), as a viscous liquid (procedure A). $^1$H NMR ($CD_3Cl$) δ 7.64-7.47 (4H, m, $CF_3Ph$), 7.34-7.23 (10H, m, 2Ph), 5.31 (s, $Ph_2CH$), 3.52 (2H, s, p-FPh$CH_2$), 3.49-3.45 (2H, t, J=6.3 Hz, $OCH_2$), 2.84-2.80 (2H, d, J=11.1 Hz, $N(CH)_2$), 2.00-1.92 (2H, t, J=11.1 Hz, $N(CH)_2$), 1.63-1.55 (4H, m), 1.49-1.42 (1H, m), 1.27-1.15 (2H, m). The free base was converted into its oxalate salt, m.p.=149-150° C. Anal. [$C_{27}H_{30}NOF_3.(COOH)_2. 0.70H_2O$] Calculated: C, 64.77; H, 6.05; N, 2.51; Found: C, 65.15; H, 6.46; N, 2.40.

Example 4

4-[2-(Diphenylmethoxy)ethyl]-1-[(4-cyanophenyl)methyl]piperidine

4-[(2-Diphenylmethoxy)ethyl]piperidine 4 (0.15 g, 0.52 mmol) was reacted with 4-cyanobenzyl bromide (0.18 g, 0.92 mmol), $Et_3N$ (0.5 ml) and $K_2CO_3$ (0.7 g) in DMF 10 ml to give 4-[2-(diphenylmethoxy)ethyl]-1-[(4-cyanophenyl)methyl]piperidine, 0.17 g (84% yield), as a white solid (procedure A). $^1$H NMR ($CD_3Cl$) δ 7.61=7.58 (2H, d, J=7.5 Hz, Ar—H), 7.45-7.42 (2H, d, J=7.5 Hz, Ar—H), 7.33-7.22 (10H, m, Ar—H), 5.31 (1H, s, $Ph_2CHO$), 351 (2H, s, p-CN-Ph$CH_2$), 3.50-3.46 (2H, t, J=6.0 Hz, $OCH_2CH_2$), 2.81-2.77 (2H, bd, J=10.8 Hz, $N(CH)_2$), 2.00-1.93 (2H, t, J=11.1 Hz, $N(CH)_2$), 1.65-1.56 (4H, m), 1.52-1.46 (1H, m, $OCH_2CH_2$), 1.30-1.18 (2H, m). The free base was converted into its oxalate salt, m.p.=120-121° C. Anal. [$C_{28}H_{30}N_2O$).($CO_2H)_2.0.26H_2O$]Calculated: C, 71.32; H, 6.48; N, 5.54; Found: C, 71.32; H, 6.69; N, 5.39.

Example 5

4-[2-(Diphenylmethoxy)ethyl]-1-[(phenylmethyl)carbonyl]piperidine

A solution of phenylacetic acid (0.11 g, 0.82 mmol), 1-[3-(dimethylamino)propyl]-3-ethylcarbodiimidehydrochloride (EDCI) (0.17 g, 0.88 mmol), and 1-hydroxybenzotriazole (HOBT) (0.11 g, 0.88 mmol) in $Et_3N$ (1 ml) and dry $CH_2Cl_2$ (10 ml) was stirred at room temperature for 1 hour. 4-[(2-diphenylmethoxy)ethyl]piperidine 4 (0.12 g, 0.41 mmol) in $CH_2Cl_2$ (5 ml) was added. The solution was stirred at room temperature overnight. The solvent was removed in vacuo, the residue was dissolved in EtOAc. The organic phase was washed with 5% citric acid aqueous solution, followed by saturated $NaHCO_3$ solution, and dried over $Na_2SO_4$. The organic extract was evaporated to give a crude product, which was purified by chromatography (EtOAc/Hexane=1/3) to collect a viscous liquid 4-[2-(diphenylmethoxy)ethyl]-1-[(phenylmethyl)carbonyl]piperidine(5e), 0.27 g (96% yield)

("Procedure B"). ¹H NMR (CD₃Cl) δ 7.32-7.25 (15H, m, Ar—H), 5.29 (1H, s, Ph₂CHO), 4.62-4.58 (1H, d, J=12.6 Hz, NCH), 3.84-3.79 (1H, d, J=13.2 Hz, NCH), 3.72 (2H, s, PhCH₂), 3.47-3.43 (2H, t, J=6.2 Hz, OCH₂), 2.96-2.88 (1H, t, J=12.6 Hz, NCH), 2.58-2.50 (1H, t, J=12.3 Hz, NCH), 1.68-1.52 (3H, m), 1.27-1.19 (2H, m), 1.10-1.03 (1H, m), 0.89-0.081 (1H, m). Anal. [C₂₈H₃₁O₂N.0.12H₂O] Calculated: C, 80.90; H, 7.51; N, 3.37; Found: C, 80.87; H, 7.50; N, 3.27.

Example 6

4-[2-(Diphenylmethoxy)ethyl]-1-[((4-methylsulfonylamino)phenyl)methyl]piperidine 4-[(2-Diphenylmethoxy)ethyl]-1-[((4-amino)phenyl)methyl]piperidine (0.11 g, 0.29 mmol) was dissolved in CH₂Cl₂ (5 ml). CH₃SO₂Cl (0.04 g) and Et₃N (0.1 ml) were added. The reaction mixture was stirred at room temperature overnight. The solvent was evaporated and EtOAc 60 ml was added. The organic phase was washed by saturated NaHCO₃/H₂O and brine, and dried over Na₂SO₄. After evaporation, the crude product was purified by chromatography (EtOAc/MeOH=100/1) to give the pure compound 4-[(2-diphenylmethoxy)ethyl]-1-[((4-methylsulfonylamino)phenyl)methyl]piperidine 26 mg (20% yield) ¹H NMR (CD₃Cl) δ 7.41-7.14 (14H, m, Ar—H), 5.31 (1H, s, Ph₂CHO), 3.49-3.34 (4H, m, OCH₂CH₂, NCH₂Ph), 3.40 (1H, s, NH), 2.98 (3H, s, CH₃SO₂), 2.85-2.81 (2H, bd, J=10.8 Hz, N(CH)₂), 1.97-1.90 (2H, t, J=10.8 Hz, N(CH)₂), 1.64-1.51 (4H, m), 1.50-1.45 (1H, m, O(CH₂)₂CH), 1.28-1.17 (2H, m). The free base was converted into its oxalate salt, m.p.=122-124° C. Anal. [C₂₈H₃₄N₂O₃S—(COOH)-1.15H₂O] Calculated: C, 61.14; H, 6.55; N, 4.75; Found: C, 61.14; H, 6.42; N, 4.71.

Example 7

4-[((2-Diphenylmethoxy)amino)methyl]-1-[(4-fluorophenyl)methyl]piperidine

To a solution of O-Benzyhydrylhydroxylamine 9 (0.25 g, 1.27 mmol) and aldehyde 1-[(4-fluorophenyl)methyl]-4-piperidinecarboxaldehyde (0.28 g, 1.27 mmol) in ClCH₂CH₂Cl (20 ml) was added Na(OAc)₃BH (0.54 g, 2.55 mmol). The reaction mixture was stirred at room temperature overnight. EtOAc 80 ml was added and the solution was washed by saturated NaHCO₃/H₂O and brine. The organic phase was dried over Na₂SO₄ and evaporated to give crude product, which was purified by chromatography (EtOAc/Hexane=1/2) to give a colorless oil, 0.43 g (84% yield). ¹H NMR (CD₃Cl) δ 7.36-7.23 (12H, m, Ar—H), 7.01-6.95 (2H, t, J=7.4 Hz, Ar—H), 3.41 (2H, s, p-F-PhCH₂), 2.82-2.78 (2H, bd, J=11.1 Hz, N(CH)₂), 2.25-2.21 (1H, m, NH), 2.00-1.93 (2H, t, J=10.8 Hz, N(CH)₂), 1.71-1.47 (7H, m). The free base was converted into its oxalate salt, m.p.=154-155° C. Anal. [C₂₆H₂₉FN₂O.(COOH).0.10H₂O] Cacl C, 67.88, H, 6.32; N, 5.65; Found: C, 67.62; H, 5.90; N, 5.51.

Example 8

4-[2-((Diphenylmethyl)amino)ethyl]-1-[(3,4-difluorophenyl)methyl]piperidine

To the solution of 4-[2-diphenylmethyl)aminocarbonyl]methyl-1-[(3,4-difluorophenyl)methyl]piperidine (0.12 g, 0.28 mmol) in dry THF 20 ml was added 1M BH₃/THF (1.0 ml). The reaction solution was refluxed for 6 hours. After the solution was cooled to room temperature, MeOH (5 ml) was added slowly. The solvent was removed under reduced pressure. 10% HCl/MeOH (10 ml) was added into the residue and the solution was refluxed for 1 hour. Solid NaHCO₃ was added after MeOH was evaporated. The mixture was extracted with EtOAc. The combined organic phase was dried over Na₂SO₄ and evaporated to give the crude product, which was purified by chromatography (Hexane/EtOAc/Et₃N=1/2/1%) to a white solid, 0.1 g (90% yield) ("Procedure E"). ¹H NMR (CD₃Cl) δ 7.39-6.99 (13H, m, Ar—H), 4.79 (1H, s, Ph₂CH), 3.39 (2H, s, F₂PhCH₂), 2.80-2.76 (2H, d, J=11.1 Hz, N(CH)₂), 2.60-2.55 (2H, t, J=7.0 Hz, NCH₂), 1.93-1.86 (2H, t, J=11.1 Hz, N(CH)₂), 1.62-1.58 (2H, d, J=12 Hz), 1.49-1.42 (2H, q, J=6.3 Hz, NCH₂CH₂), 1.35-1.31 (1H, m, NCH₂CH₂CH(CH₂)₂), 1.26-1.19 (2H, t, J=12.0 Hz). The free base was converted into its HCl salt, m.p.=280-281° C. Anal: (C₂₇H₃₀N₂F₂.2HCl.0.25H₂O) Calculated: C, 65.12; H, 6.85; N, 5.62; Found: C, 65.13; H, 6.80; N, 5.28.

Example 9

4-[2-((Diphenylmethyl)amino)ethyl]-1-(phenylmethyl)piperidine

Compound 4-[2-(diphenylmethyl)aminocarbonyl)methyl-1-(phenylmethyl)piperidine (0.54 g, 1.31 mmol) was reacted with 1 M BH₃/THF (5.0 ml) in THF (10 ml) to produce 4-[2-(diphenylmethyl)amino]ethyl-1-(phenylmethylpiperidine, 0.44 g (84% yield)(procedure E). ¹H NMR (CD₃Cl) δ 7.39-7.19 (15H, m, Ar—H), 4.79 (1H, s, PhCH), 3.47 (2H, s, PhCH₂), 2.86-2.82 (2H, d, J=1.1 Hz, N(CH)₂), 2.59-2.55 (2H, t, J=7.2 Hz, NCH₂), 1.94-1.87 (2H, t, J=11.1 Hz, N(CH)₂), 1.61-1.58 (2H, m), 1.48-1.42 (2H, m), 1.34-1.20 (3H, m). The free base was converted into its HCl salt, m.p. −172-174° C. Anal: (C₂₇H₃₂N₂.2HCl 106H₂O) Calculated: C, 68.05; H, 7.64; N, 5.88; Found: C, 68.06; H, 7.82; N, 5.90.

Example 10

4-[2-((Diphenylmethyl)-N-methylamino)ethyl]-1-(4-phenylmethyl)piperidine

A solution of 4-[(2-Diphenylethyl)aminomethyl]-1-[(4-fluorophenyl)methyl]piperidine (0.23 g, 0.59 mmol), formaldehyde (1.0 g, 37%/H₂O) and formic acid (2.0 g, 88%/H₂O) was refluxed for 3 hours. After the reaction solution was cooled to room temperature, the solvent was removed under vacuo. The crude product was purified by chromatography (EtOAc/Hexane=1/2) to give a white solid 0.17 g (71% yield). ¹H NMR (CD₃Cl) δ 7.40-7.16 (12H, m, Ar—H), 7.05-6.95 (2H, t, J=7.4 Hz, Ar—H), 4.31 (1H, s, Ph₂CHN), 3.41 (2H, s, p-FPhCH₂N), 2.80-2.76 (2H, d, J=11.8 Hz, N(CH)₂), 2.36-2.30 (2H, t, J=7.5 Hz, NCH₂), 2.11 (3H, s, NCH₃), 1.91-1.83 (2H, t, J=11.4 Hz, N(CH)₂), 1.54-1.50 (2H, d, J=11.4 Hz), 1.47-1.40 (3H, m, NCH₂CH₂CH), 1.32-1.10 (2H, m). The free base was converted into its HCl salt, m.p.=260-261° C. Anal. [C₂₈H₃₃N₂F-2HCl-0.50H₂O]] Calculated: C, 67.46; H, 7.29; N, 5.61; Found: C, 67.33; H, 7.19; N, 5.56.

Example 11

4-[[2-(Diphenyl)ethyl]aminomethyl]-1-[(4-fluorophenyl)methyl]piperidine

Compound 4-[(2-diphenylethyl)aminocarbonyl]-1-[(4-fluorophenyl)methyl]piperidine (0.32 g, 13 mmol) was reacted with 1M BH₃/THF (4.0 ml) in THF (20 ml) to produce 4-[(2-diphenylethyl)aminomethyl]-1-[(4-fluorophenyl)methyl]piperidine, 0.25 g (81% yield)(procedure E). $^1$H NMR (CD$_3$Cl) δ 7.32-7.19 (12H, m, Ar—H), 7.00-695 (2H, m, Ar—H), 4.21-4.17 (1H, t, J-7.7 Hz, (Ph$_2$CH), 3.67 (1H, s, NH), 3.41 (2H, s, p-FPhCH$_2$), 3.22-3.19 (2H, d, J=7.8 Hz, NH CH$_2$CH(Ph)$_2$), 2.83-2.79 (2H, bd, J=11.1 Hz, N(CH)$_2$), 2.52-2.50 (2H, d, J=6.6 Hz, NHCH$_2$CH), 1.91-1.84 (2H, t, J=1.1 Hz, 1.58-1.54 (2H, d, J-12 Hz), 1.45-1.39 (1H, m, NHCH$_2$ CH), 1.21-1.14 (2H, t, J=12 Hz). The free base was converted into its HCl salt, m.p.=126-127° C. Anal. [C$_{27}$H$_{31}$FN$_2$O.2HCl] Calculated: C, 62.96; H, 7.31; N, 5.43; Found: C, 62.93; H, 7.19; N, 5.41.

Example 12

4-[(Bis(4-fluorophenyl)methylamino)methyl]-1-[2-(phenyl)ethyl]piperidine

Compound 4-[(2-diphenylethyl)aminomethyl]-1-[(4-fluorophenyl)methyl]piperidine (0.30 g, 0.71 mmol) was reacted with 1M BH$_3$/THF (4. ml) in NMR (25 ml) to produce a white solid 4-[(bis(4-fluorophenyl)methylamino)methyl]-1-(phenylethyl)piperidine, 0.28 g (96% yield)(procedure E). $^1$H NMR (CD$_3$Cl) δ 7.35-7.18 (10H, m, Ar—HO, 7.00-6.95 (3H, m, Ar—H), 4.74 (1H, S, P-FPh)$_2$CH), 3.02-2.99 (2H, d, J=10.8 Hz, N(CH)$_2$), 2.83-2.78 (2H, M), 2.60-2.55 (2H, m), 2.45-2.43 (2H, d, J=6.2 Hz, NHCH$_2$CH), 2.04-1.96 (2H, t, J=11.4 Hz, N(CH)$_2$), 1.78-1.26 (5H, m). The free base was converted into its HCl salt, m.p.=214-215° C. Anal. (C$_{27}$H$_{30}$F$_2$N$_2$.2HCl.0.50H$_2$O) Calculated: C, 64.58; H, 6.61; N, 5.57; Found: C, 64.61; H, 6.65; N, 5.43.

Example 13

[[(2-(Diphenyl)ethyl]-N-methylaminomethyl]-1-[(4-fluorophenyl)methyl]piperidine

4-[(2-Diphenylethyl)aminomethyl]-1-[)-4-fluorophenyl) methyl]-piperidine 4-[(2-diphenylethyl)aminomethyl]-1-[(4-fluorophenyl)methyl]piperidine (45 mg, 0.11 mmol) was refluxed in formaldehyde (1.0 g) and formic acid (2.0 g, 37%/H$_2$O) to produce 4-[(2-diphenylethyl)-N=methylaminomethyl]-1-[(4-fluorophenyl)methyl]piperidine, 44 mg (88% yield)(procedure F). $^1$H NMR (CD$_3$Cl) δ 7.28-7.13 (12H, m, Ar—H), 7.02-6.96 (2H, t, J=8.4 Hz, Ar—H), 4.15-410 (1H, t, J=7.5 Hz, Ph$_2$CH), 3.46 (2H, s, F-PhCH$_2$), 2.91-2.88 (2H, d, J=7.5 Hz, Ph$_2$CHCH$_2$N), 2.81-2.77 (2H, d, J=1.1 Hz, N(CH)$_2$), 2.20 (3H, s, CH$_3$), 2.20-2.17 (2H, d, J=7.5 Hz, NCH$_2$CH), 1.90-1.83 (2H, t, J=11.4 Hz, N(CH)$_2$), 1.52-1.47 (2H d, J=12.9 Hz), 1.54-1.28 (1H, m, NCH$_2$CH), 1.14-1.06 (2H, t, J=12.4 Hz). The free base was converted into its oxalate salt, m.p.=144-145° C.

Anal. [C$_{28}$H$_{33}$N$_2$F-2(COOH)$_2$.1.47H$_2$O]] Calculated: C, 61.68; H, 5.99; N, 4.49;
Found: C, 61.65; H, 5.99; N, 4.35.

Example 14

4[2-[(1-(phenyl)ethyl)amino]ethyl]-1-[(4-fluorophenyl)methyl]piperidine

Compound 4-[(1-phenylethyl)aminocarbonyl]methyl-1-[(4-fluorophenyl)methyl]piperidine (0.33 g, 0.93 mmol) was reacted with 1M BH$_3$/THF (5.0 ml) to produce a viscous oil, 0.23 g (95% yield)(procedure E). $^1$H NMR (CD$_3$Cl) δ 7.34-=7.21 (5H, m, Ar—H), 7.01-6.95 (2H, t, J=8.4 Hz, Ar—H), 4.09-4.07 (1H, d, J=6.0 Hz, NH), 3.77-3.71 (1H, q, J=6.3 Hz, PhCHMe), 3.42 (2H, s, p-FPhCH$_2$), 2.82-2.78 (2H, d, J=10.8 Hz, N(CH)$_2$), 2.55-2.37 (2H, m, NCH$_2$), 1.91-1.83 (2H, t, J=11.4 Hz, N(CH)$_2$), 1.59-1.53 (4H, m), 1.44-1.38 (1H, m), 1.36-1.34 (3H, d, J=6.0 Hz, CH$_3$), 1.25-1.14 (2H, m), The free base was converted into its oxalate salt, m.p.=172-173° C. Anal. [C$_{22}$H$_{29}$FN$_2$.2(COOH)$_2$] Calculated: C, 59.99; H, 6.39; N, 5.38; Found C, 59.84; H, 6.46; N, 5.29.

Example 15

Synthesis of racemic cis- and trans-2-Diphenylmethyl-5-(4-fluorobenzylamino)piperidine To a room temperature solution of 420 mg racemic cis- and trans-2-diphenylmethyl-5-aminopiperidine (1.58 mmol), 156 mg 4-fluorobenzaldehyde (0.8 equiv), 94 mg glacial HOAc (1 equiv) in 30 mL 1,2-dichloroethane was added portionwise 119 mg sodium cyanoborohydride (1.2 equiv). The mixture was stirred for 18 hours. Then, H$_2$O was added and the mixture stirred for 30 min, then acidified with conc HCl, and stirred another 30 min. Then the mixture was basified with conc NaOH and extracted thrice with CH$_2$Cl$_2$. The organic phases were collected, dried (MgSO$_4$) and evaporated. The residue was chromatographed (SiO$_2$; CH$_2$Cl$_2$; MeOH) to purify the mixture (240 mg, 40%) of both diastereomeric pairs. Then this mixture was further chromatographed (SiO$_2$; 1 hexane; 1 EtOAc: 0.06 triethylamine) to separate the diastereomers. Eluting first: $^1$H, NMR, (CDCl$_3$; 400 MHz) δ 1.3-1.4 (2H, m, H-3), 1.49 (1H, tt, $^2$J and $^3$J$_{3a}$=13.6 Hz; $^3$J$_{3e}$ and $^3$J$_{5e}$=4.0 Hz, H-4ax), 1.65-1.85 (3H, m, H-4ax 2NH), 2.65-2.72 (2H, m, H-5eq, H-6ax), 2.99 (1H, d, $^2$J=10.4 Hz, H-6eq), 3.28 (1H, dt, $^3$J=4.4 and 10.8 Hz, H-2ax), 3.71 (2H, s, CH$_2$C$_6$H$_4$F), 3.81 (1H, d, $^3$J=9.6 Hz, CH(C$_6$H$_5$)$_2$), 6.99 (2H, t, $^3$J=8.4 Hz, ArH ortho F), 7.12-7.39 (12H, m, ArH). Precipitated as bis-hydrochloride salt. mp 60-105° C. Elemental analysis calculated for C$_{25}$H$_{29}$N$_2$FCl$_2$.0.5H$_2$O: C, 65.93; H, 6.59; N, 6.15. Found: C, 65.26; H, 6.78; N, 6.49.

Eluting second: racemic trans-2-diphenylmethyl-5-(4-fluorobenzylamino)piperidine (96 mg, 38.5%), $^1$H NMR (CDCl$_3$; 400 MHz) δ 1.17 (2H, qm, $^3$J=10 Hz, H-3ax and H-4ax), 1.57-1.65 (1H, m, H-3eq), 1.4-1.7 (bs, NH), 1.9-1.96 (1H, m, H-4eq), 2.33 (1H, t, $^2$J and $^3$J=10.4 Hz, H-6ax), 2.65 (1H, m, Σ$^3$ J=36 Hz, H-5ax), 3.15-3.25 (2H, m, H-2ax, H-6eq), 3.68 (1H, d, $^2$J=0.6 Hz, CH(C$_6$H$_5$)$_2$), 3.75 (2H, s, CH$_2$C$_6$H$_4$F), 6.97 (2H, t, $^3$J=8.8 Hz, ArH Ortho F), 7.1-7.3 (10H, m, ArH), 7.36 (2H, d, $^3$J=7.6 Hz, ArH meta F). Precipitated as bis-hydrochloride salt. Elemental analysis calculated for C$_{25}$H$_{29}$N$_2$FCl$_2$.0.5H$_2$O: C, 65.93; H, 6.59; N, 6.15. Found: C, 65.56; H, 6.89; N, 6.14

Example 16

Synthesis of racemic trans-3-hydroxy-4-[2-diphenyl-methoxy)ethyl]-1-[(4-fluorophenyl)methyl]piperidine To a stirred suspension of

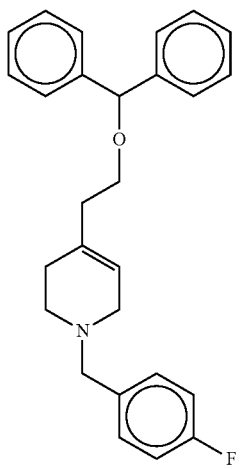

(0.92 g, 1.9 mmol) in THF (10 mL) cooled to 0° C. was added dropwise 1M BH$_3$ tetrahydrofuran complex (7.7 mL, 7.7 mmol, 4 equiv). Afterwards, the cooling bath was removed and the solution allowed to warm to RT. The mixtures was then refluxed for 12 hr. After cooling to 0° C., H$_2$O (5.76 mL), EtOH (5.76 mL) and 3N NaOH (15 mL) were added followed by dropwise addition of 30% H$_2$O$_2$ (18 mL). The reaction was stirred at 55° C. for 12 hours then cooled to RT and extracted thrice with CH$_2$Cl$_2$. The extracts were pooled, dried (MgSO$_4$) and evaporated to a clear oil. The crude product was chromatographed (SiO$_2$; 5% MeOH/CH$_2$Cl$_2$) to furnish the free base (0.553 mg, 71%). $^1$H NMR (CDCl$_3$) ∂ 1.34-1.39 (2H, m), 1.59-1.55 (2H, m), 1.81-1.95 (3H, m), 2.72 (1H, d, J=9.9 Hz), 2.98 (1H, d, J=10.5 Hz), 3.42-3.63 (5H, m), 5.37 (1H, s), 6.98 (2H, t, J=9.3 Hz), 7.22-7.35 (12H, m). This was then reacted in EtOH (5 mL) with oxalic acid dihydrate (0.169 g, 1.1 equiv) to furnish the title compound (468 mg, 77%). mp 143-50° C. Elemental analysis calculated for C$_{28}$H$_{31}$NO$_6$F: C, 68.37; H, 6.29; N, 2.75. Found: C, 67.96; H, 6.43; N, 2.63.

Example 17

Synthesis of racemic trans-3-Propionyl-4-[2-(diphenylmethoxy)ethyl]-1-[(4-fluorophenyl)methyl]piperidine To a solution of 61 mg 3-hydroxy-4-[2-(diphenylmethoxy)ethyl]-1-[(4-fluorophenyl)methyl]piperidine (0.15 mmol) and 21 mg triethylamine (0.23 mmol, 1.5 equiv) in 2 mL CH$_2$Cl$_2$ cooled in an ice bath was added dropwise 18 mg propionyl chloride (0.19 mmol, 1.3 equiv) and the reaction was allowed to warm to RT. After 1 hr, the same quantities of triethylamine and propionyl chloride were added. After 1 hr, H$_2$O was added and the organic layer was separated, dried (MgSO$_4$) and evaporated. The remaining residue was chromatographed (SiO$_2$; CH$_2$Cl$_2$/MeOH) to yield the title compound as the free base (53 mg, 77%). 1H NMR (CDCl$_3$ ∂ 1.1 (3H, t, J=8.1 Hz), 1.26-1.95 (7H, m), 2.26 (2H, q, J=7.2 and 7.5 Hz), 2.71 (1H, d, J=11.7 Hz), 3.02 (1H, d, J=10.5 Hz), 3.41-3.52 (4H, m), 4.67 (1H, t, J=9.6 Hz), 5.31 (1H, s), 6.98 (2H, t, J=9.3 Hz), 7.2-7.4 (12H, m). This was then reacted in a mixture of 2 mL 50% EtOH/Et$_2$O with oxalic acid dihydrate (15.4 mg, 1.1 equiv) to furnish the title compound. mp ° C. Elemental analysis calculated for C$_{32}$H$_{36}$NO$_7$F-0.5H$_2$O: C, 67.43; H, 6.41; N, 2.46. Found: C, 67.34; H, 6.43; N, 2.44.

Example 18

Synthesis of racemic 3-Keto-4-[2-(diphenylmethoxy)ethyl]-1-[(4-fluorophenyl)methyl]piperidine To a solution of oxalyl chloride (0.4 mmol, 0.87 equiv) in CH$_2$Cl$_2$ (3 mL) cooled to −78° C. was added dropwise 108 mg dimethylsulfoxide (1.38 mmol, 3 equiv). The mixture was stirred for 10 min and a solution of 236 mg racemic trans-3-hydroxy-4-[2-(diphenylmethoxy)ethyl]-1-[(4-fluorophenyl)methyl]piperidine (0.46 mmol) in CH$_2$Cl$_2$ (1 mL) was added dropwise. After stirring 15 min, triethylamine (825 mg, 17.6 equiv) was added and the mixture was allowed to warm to room temperature. All volatiles were evaporated at room temperature and the remaining residue was chromatographed (SiO$_2$; hexane: EtOAc: MeOH) to furnish the free base (116 mg, 60%), which decomposes at room temperature and must be stored in the cold. $^1$H NMR (CdCl$_3$) ∂ 1.45-1.65 (2H, m), 2.0-2.1 (1H, m), 2.2-2.3 (1H, m), 2.38-2.6 (2H, m), 2.77 (1H, d, J=13.6 Hz), 2.9 (1H, bd, J=13.6 Hz), 3.45-3.55 (4H, m), 5.30 (1H, s), 6.99 (2H, t, J=11.2 Hz), 7.19-7.39 (12H, m). The title compound (125 mg, 50%) was furnished by reacting the free base (205 mg) with oxalic acid dihydrate (62 mg, 1 equiv). mp 104-9° C. Elemental analysis calculated for C$_{29}$H$_{30}$NO$_6$F: C, 68.64; H, 5.92; N, 2.76. Found: C, 68.34; H, 5.93; N, 2.68.

Example 19

Synthesis of 4-[2-(diphenylmethoxy)ethyl]-1-[(4-iodophenyl)methyl]piperidine

4-[2-(diphenylmethoxy)ethyl]piperidine (0.23 g, 0.77 mmol) was reacted with 4-iodo benzyl bromide (0.76 g, 2.5 mmol) and K$_2$CO$_3$ (1.00 g, 7 mmol) in EtOH (10 mL) to give a thick oil, 0.17 g (%). 1H NMR (300 MHz, CDCl3): 1.21-1.63 (7H, m), 1.87-1.93 (t, J=11 Hz, 2H, N(CH2)-), 2.79-2.83 (bd, J=12 Hz, 2H, N(CH2)-), 3.41-3.49 (4H, m), 5.31 (s, 1H, Ph2CHO—), 7.05-7.63 (14H, m, ArH). Free base was converted into its oxalate sale, m.p.=160-161° C. Anal. C$_{27}$H$_{30}$INO. (COOH)$_2$.

Biological Testing

We have surprisingly discovered that longer aromatic-alkyl chains in piperidine derivatives give rise to more interaction with the serotonin transporter (SERT), and hence less selectivity (c.f. A. K. Dutta et al., "Structure-Activity Relationship Studies of Novel 4-[2-[Bis(4-fluorophenyl)methoxy]ethyl]-1-(3-phenylpropyl)piperidine Analogs: Synthesis and Biological Evaluation at the Dopamine and Serotonin Transporter Sites", J. MED. CHEM., 1996, 39, 749-756; A. K. Dutta et al., "Highly Selective, Novel Analogs of 4-[2-(diphenylmethoxy)ethyl]-1-benzylpiperidine For The Dopamine Transporter: Effect of Different Aromatic Substitutions on Their Affinity and Selectivity", J. MED. CHEM., 1997, 40, 35-43; A. K. Dutta et al., Potent and Selective Ligands for the Dopamine Transporter (DAT): Structure-Activity Relationship Studies of Novel 4-[2-(diphenylmethoxy)ethyl]-1-(3-phenylpropyl)piperidine Analogs", J. MED. CHEM., 1998, 41, 699-705). In an effort to explore the effect of electronegative fluorine atoms and the strong electron withdrawing group CN, the compounds of Examples 1-4 were designed and synthesized. The presence of electronegative and electron withdrawing groups enhanced the activity and selectivity of these analogs. These novel compounds, with but a methylene group between the piperidine N-atom and the aryl ring, and with an electronegative aryl substituent, exhibited profound selectivity and potency for the dopamine transporter (DAT). Thus, the compound of Example 4 with a strong electron withdrawing cyano group present in the phenyl ring exhibited remarkable potency and selectivity (IC50, 3.7 nM, SERT/DAT=615, Table 1) for the dopamine transporter. This is a remarkable improvement over the standard reference compound GBR 12909 (IC50, 14 nM, SERT/DAT=6). The compound of Example 2 also showed good potency and more selectivity than GBR 12909 for the DAT (SERT/DAT=122).

The compounds of Examples 8, 9, 11 and 12 (Table 1) employ a 4-(aminoalkyl) linkage between the piperidine ring and the bisaromatic methane portion of the molecule rather than an oxyalkyl linkage. Both Examples 8 and 9 are more potent and selective than the standard GBR 12909 molecule (IC50, 7.0 and 4.5 nM, respectively); SERT/DAT=227 and 347, respectively). The compound 4-[2-(diphenylmethoxy)ethyl]-1-[(4-iodophenyl)methyl]piperidine sets a new standard of activity.

In the compound of Example 11 where the N-atom was relocated to an adjacent position, an interesting effect consisting of the strong affinity for the DAT and the moderate affinity for the SERT was observed. Compound with such dual activity might find unique applications in the medication development for drug abuse and in other neurological disorders, including treatment of depression.

None of these compounds developed in this current series showed any appreciable activity for the norepinephrine transporter (NET), which demonstrates their selectivity for the DAT.

The current novel compounds were also evaluated in the dopamine reuptake inhibition assay which measures the extent of inhibition of dopamine reuptake in the cytosol by these novel compounds. In this regard, cocaine and GBR 12909 are potent DA uptake inhibitors. Ideally, a desirable drug for the treatment of drug addiction should possess less dopamine uptake inhibitory potency and should be less potent than GBR 12909 in that regard, which will increase the drug's chances to act as cocaine antagonist. In this current series of compounds, Table 2, all of the listed results reflect an increased potential of these novel compounds to act as cocaine antagonists than GBR 12909.

TABLE 1

Affinity and Selectivity of Drugs at the Dopamine (DAT), Serotonin (SERT) and Norepinephrine (NET) Transporters

| Compound | DAT, $IC_{50}$, nM | SERT, $IC_{50}$, nM | NET, $IC_{50}$, nM | DAT/SERT |
|---|---|---|---|---|
| CFT | 32.3 ± 2.6 | | | |
| GBR 12909 | 10.6 ± 1.9 | 132.0 ± 0.0 | 496 ± 22 | 12 |
| Example 1 | 23.4 ± 3.8 | 1145.7 ± 43.4 | | 49 |
| Example 2 | 10.1 ± 0.9 | 1221 ± 139.4 | | 122 |
| Example 3 | 32.1 ± 2.1 | 2262.8 ± 144.1 | | 71 |
| Example 4 | 3.7 ± 0.6 | 2277 ± 470 | | 615 |
| Example 5 | 2156 ± 54 | >1,000 | | |

TABLE 1-continued

Affinity and Selectivity of Drugs at the Dopamine (DAT), Serotonin (SERT) and Norepinephrine (NET) Transporters

| Compound | DAT, $IC_{50}$, nM | SERT, $IC_{50}$, nM | NET, $IC_{50}$, nM | DAT/SERT |
|---|---|---|---|---|
| Example 6 | 26.6 ± 1.4 | 585.6 ± 29.2 | | 22 |
| Example 7 | 34.4 ± 4.2 | 625.8 ± 33 | 691 ± 68 | 19 |
| Example 8 | 7.0 ± 1.7 | 1587 ± 160 | 1,027 ± 94 | 227 |
| Example 9 | 4.5 ± 0.6 | 1562 ± 208 | 2,623 ± 173 | 347 |
| Example 10 | 213 ± 3 | 1659 ± 469 | | 8 |
| Example 11 | 19.7 ± 1.4 | 137.2 ± 45.6 | 1,111 ± 119 | 7 |
| Example 12 | 65.3 ± 3.2 | 1098 ± 245.6 | | 17 |
| Example 13 | 94.0 ± 12.5 | 2524 ± 230 | | 27 |
| Example 14 | 295.4 ± 40.9 | 963 ± 38.5 | | |
| —[1] | 751.0 ± 61.6 | 5855.7 ± 594.6 | | |
| 3-OH[2] | 14.3 ± 3.7 | 984 ± 94 | 678 ± 13 | 69 |
| Example 19 | 0.96 ± 0.16 | 2920 ± 432 | 1151 ± 116 | 3041 |

[1] 4-[((1-phenylethoxy)ethyl]-1-[(4-fluorophenyl)methyl]piperidine
[2] 4-[2-(diphenylmethoxy)ethyl]-1-[(3-hydroxyphenyl)methyl]piperidine
[3] 4-[2-(diphenylmethoxy)ethyl]-1-[(4-iodophenyl)methyl]piperidine

TABLE 2

Inhibition of Dopamine Reuptake in Rat Synaptosome Tissue

| Compound | [3H]DA Inhibition, $IC_{50}$ (nM) | [3H]DA/Binding, IC50 |
|---|---|---|
| GBR 12909 | 6.63 ± 0.43 | 0.62 |
| Example 2 | 12.03 ± 1.62 | 1.33 |
| Example 4 | 4.58 ± 0.80 | 1.23 |
| Example 7 | 16.6 ± 2.8 | 0.48 |
| Example 6 | 9.7 ± 1.2 | 0.36 |
| Example 11 | 49.56 ± 7.2 | 2.5 |
| Example 9 | 20.6 ± 2.5 | 4.5 |
| Example 8 | 10.7 ± 1.8 | 1.5 |

The activities of racemic cis- and trans-isomers of the compounds of Example 15 were measured. The results are presented below in Table 3. The selectivities with respect to SERT/DAT, NET/DAT and [3H] DA/DT binding ratios are presented in Table 4, along with similar data for cocaine and subject invention Example 11. As can be seen, there is a significant change in the selectivity as between the cis- and trans-isomers. It is expected that the individual stereoisomers of each pair of geometric isomers will also exhibit quite different activity.

TABLE 3

Binding Activity of Cis and Trans at the Dopamine, Serotonin and Norepinephrine Transporters

| Compound | DAT, IC$_{50}$, nM [$^3$H]WIN 35,428 | SERT, IC$_{50}$, nM [$^3$H]citalopram | NET, IC$_{50}$, nM [$^3$H]nisoxetine | [$^3$H]DA uptake Inhibition, IC$_{50}$ (nM) |
|---|---|---|---|---|
| (±)-7a | 30.00 ± 0.5 | 2,813 ± 411 | 1,349 ± 190 | 28.9 ± 2.5 |
| (±)-7b | 212 ± 20 | 1,333 ± 102 | 4,468 ± 1,181 | 106 ± 10 |

TABLE 4

Selectivity of Various Ligands for their Binding to the Monoamine Transporters

| Compound | SERT/DAT | NET/DAT | [$^3$H]DA/DAT Binding |
|---|---|---|---|
| Cocaine | 2.7 | 6.36 | |
| Example 11 | 6.9 | 5.6 | 2.5 |
| (±)-7a | 93.7 | 44.9 | 0.03 |
| (±)-7b | 6.28 | 21 | 0.5 |

TABLE 5

Affinity and Selectivity of Drugs at the Dopamine, Serotonin and norepinephrine Transporters in Rat Striatum

| Compound | DAT, IC$_{50}$, nM, [$^3$H]WIN 35, 428$^a$ | SERT, IC$_{50}$, nM [$^3$H]citalopram$^a$ | NET, IC$_{50}$, nM [$^3$H]nisoxetine$^a$ | SERT/DAT |
|---|---|---|---|---|
| Cocaine | 266 ± 37 | 737 ± 160 | 3,526 ± 554 | 2.7 |
| GBR 12909 | 10.6 ± 1.9 | 132 ± 0 | 496 ± 22 | 12 |
| Example 16 | 5.96 ± 1.26 | 1,108 ± 477 | 637 ± 114 | |
| Example 18 | 99 ± 18 | 7,747 ± 1618 | 6,299 ± 694 | |
| Example 17 | 583 ± 81 | 177,800 ± 53,00 | 35,806 ± | |

III. Examples of FIGS. 7 Through 9

Reagents and solvents were obtained from commercial suppliers and used as received unless otherwise indicated. Dry solvent was obtained according to the standard procedure. All reactions were performed under inert atmosphere (N$_2$) unless otherwise noted. Analytical silica gel 60 F$_{254}$-coated TLC plates were purchased from EMD Chemicals, Inc. and were visualized with UV light or by treatment with phosphomolybdic acid (PMA). Flash chromatography was carried out on Baker Silica Gel 40 mm. $^1$H NMR spectra were routinely obtained at Varian 400 MHz FT NMR. The NMR solvent used was CDCl$_3$ as indicated. TMS was used as an internal standard. Elemental analyses were performed by Atlantic Microlab, Inc. and were within ±0.4% of the theoretical value.

Figure 7:
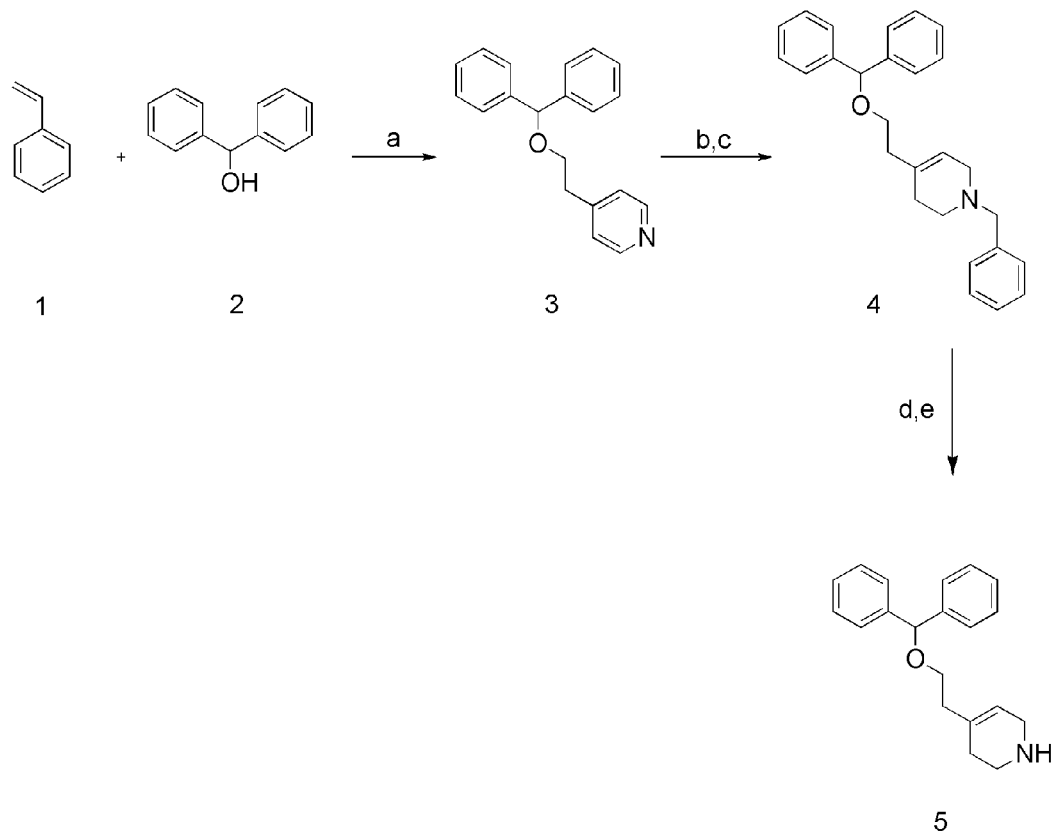
FIG. 7 illustrates another synthesis scheme and the structures of certain of the subject invention compounds.

Synthesis of 4-(2-(Benzhydryloxy)ethyl)pyridine (3). With reference to FIG. 7, to a stirred solution of 4-vinylpyridine 1 (10 g, 95.1 mmol) and benzhydrol 2 (35.04 g, 190 mmol), was added sodium methoxide (1.541 g, 28.5 mmol). The reaction mixture was heated at 130-140° C. for 20 hrs, cooled to RT and acidified with 1 N HCl (150 ml). The solution was extracted with ethyl acetate (3×30 ml) to remove unreacted benzhydrol and side product dibenzhydryl ether. The aqueous solution was further basified with 10% NaOH solution (pH 10) and extracted with dichloromethane (3×30 ml). The combined organic layers were washed with water (2×20 ml), dried over anhydrous sodium sulfate and the solvent evaporated in vacuo. The oily residue was subjected to vacuum distillation to remove unreacted 4-vinylpyridine (3.9 g). The product was dried under vacuum to remove trace amounts of 4-vinylpyridine to yield 8.7 g (52%) of the title compound 3. $^1$H-NMR (CDCl$_3$; 400 MHz): 2.90-2.93 (t, 2H, J=6.4 Hz, OCH$_2$CH$_2$), 3.66-3.67 (t, 2H, J=6.8 Hz, OCH$_2$CH$_2$), 5.32 (s, 1H, PhCH(O)Ph), 7.13-7.14 (d, 2H, J=5.6 Hz, 3,5-Pyr-H), 7.17-7.33 (m, 10H, ArH), 8.47-8.48 (d, 2H, J=6.0 Hz, 2,6-Pyr-H).

Synthesis of 4-(2-(benzhydryloxy)ethyl)-1-benzyl-1,2,3, 6-tetrahydropyridine (4). With reference to FIG. 7, 4-(2-(benzhydryloxy)ethyl)pyridine 3 (4.0 g, 13.82 mmol) and benzyl bromide (2.86 g, 16.73 mmol) were dissolved in 20 ml of dry acetonitrile and refluxed for 6 hrs. The solvent was removed in vacuo. After drying the residue for 2 hrs under high vacuum, it was dissolved in 30 ml of dry methanol and cooled in an ice-bath. Sodium borohydride (0.76 g, 20.05 mmol) was then added very slowly portionwise over a period of 1.5 hrs, and the solution was gradually brought to room temperature. The reaction was quenched with water after stirring for 4 h, and methanol was removed in vacuo. The residual product was dissolved in ethyl acetate, washed with water, dried (Na$_2$SO$_4$), and concentrated. The crude product was purified by column chromatography over silica gel (hexane:ethyl acetate 5:1) to produce 4 (5.0 g, 94%) as a colorless oil. $^1$H-NMR (CDCl$_3$; 400 MHz): 2.086 (brs, 2H, H-3), 2.32-2.35 (t, 2H, J=6.8 Hz, OCH$_2$CH$_2$), 2.52-2.54 (t, 2H, J=5.6 Hz, H-2), 2.94-2.94 (brm, 2H, H-6) 3.52-3.55 (m, 4H, NCH$_2$Ph, OCH$_2$CH$_2$), 5.34 (s, 1H, PhCH(O)Ph), 5.41-5.42 (brs, 1H, CH═C), 7.12-7.37 (m, 15H, ArH).

Synthesis of 4-(2-(benzhydryloxy)ethyl)-1,2,3,6-tetrahydropyridine (5). With reference to FIG. 7, a solution of 4-(2-(benz-hydryloxy)ethyl)-1-benzyl-1,2,3,6-tetrahydropyridine 4 (12.44 g, 0.0324 mol) and methyl chloroformate (5.0 ml, 0.0648 mol) in benzene (40 ml) was refluxed for 6 hrs. After completion of reaction (monitored by TLC), the solvent was removed in vacuo to yield methyl 4-(2-(benzhydryloxy) ethyl)-5,6-dihydropyridine-1(2H)-carboxylate in the form of viscous oil. It was purified by column chromatography (hexane: EtOAc 9:1) to get 6.7 g (59%) of pure product.

To a stirred solution of methyl 4-(2-(benzhydryloxy) ethyl)-5,6-dihydropyridine-1(2H)-carboxylate (6.5 g, 18.49 mmol) in ethanol (25 ml) was added Claisen's alkali (6.457 g KOH dissolved in 5 ml water and 20 ml methanol). The solution was refluxed overnight, concentrated in vacuo, cooled and diluted with water (40 ml) and extracted with ether (3×30 ml). The combined ethereal extract was dried ($Na_2SO_4$) and evaporated to afford viscous liquid. The product was purified by column chromatography over silica gel (ethyl acetate:methanol:triethylamine 20:10:2.5) to obtain compound 5 as yellowish viscous liquid (4.8 g, 88%). $^1$H-NMR ($CDCl_3$; 400 MHz): 2.03 (brm, 2H, H-3), 2.29-2.32 (t, 2H, J=6.4 Hz, $OCH_2CH_2$), 2.92-2.95 (t, 2H, J=5.6 Hz, H-2), 3.31 (brs, 2H, H-6), 3.49-3.53 (t, 2H, $OCH_2CH_2$), 5.32 (s, 1H, PhCH(O)Ph), 5.41 (brs, 1H, CH=C), 5.76 (brs, 1H, —NH), 7.17-7.33 (m, 10H, ArH).

Figure 8:
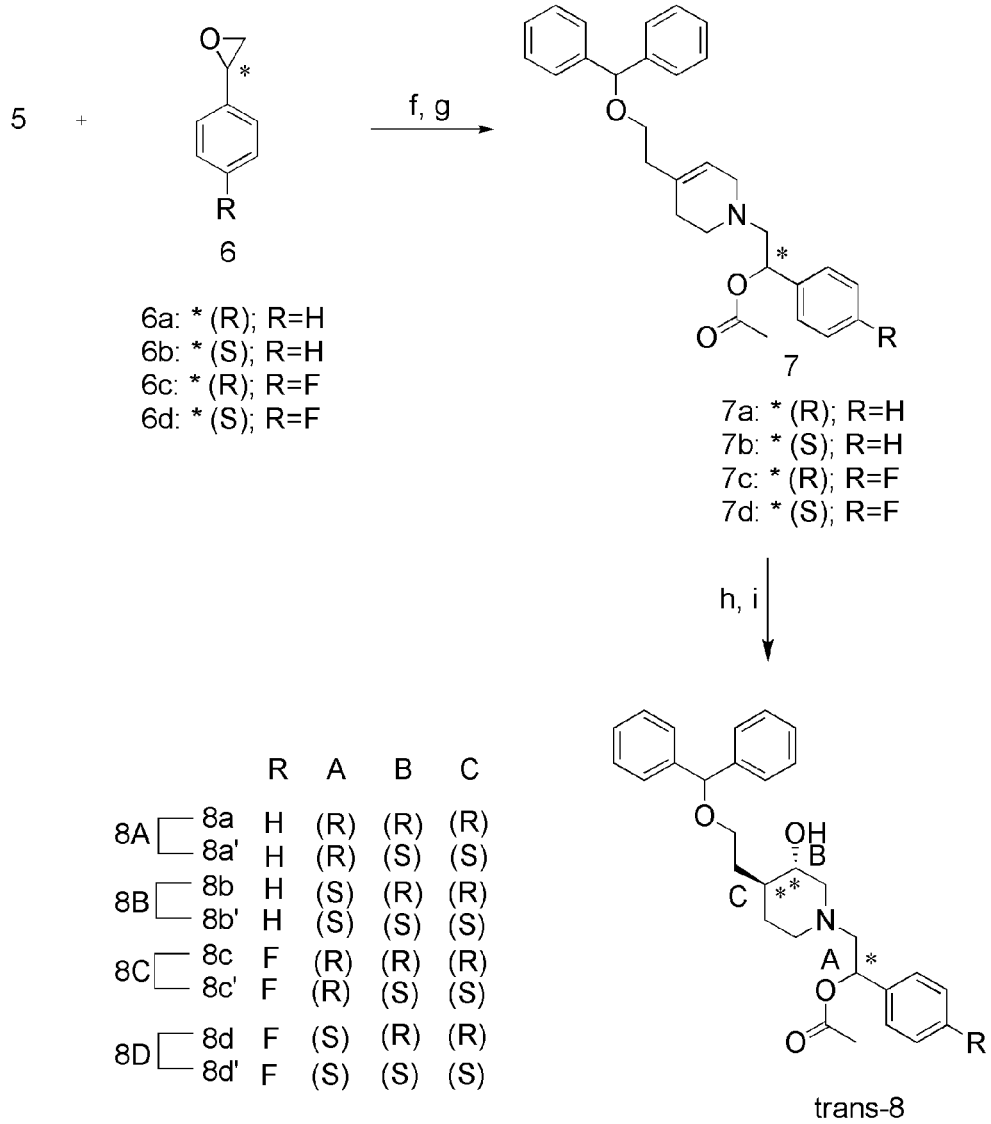
FIG. 8 illustrates another synthesis scheme and the structures of certain of the subject invention compounds.

General Procedure I. With reference to FIG. 8, a solution of 4-(2-(benzhydryloxy)ethyl)-1,2,3,6-tetrahydro-pyridine 5 (1 equiv.) and styrene oxide 6 (1 equiv.) in ethanol was refluxed overnight. The reaction mixture was cooled to RT and the solvent was evaporated in vacuo. The brownish oily residue was purified by column chromatography over silica gel (hexane:ethyl acetate 1:1) in order to remove any unreacted starting materials, if any, to yield a colorless oil which was found to be a mixture of regioisomers [in case of compound 7a, (R)-2-(4-(2-(benzhydryloxy)ethyl)-5,6-dihydropyridin-1 (2H)-yl)-1-phenyl-ethanol, the desired product, and (R)-2-(4-(2-(benzhydryloxy)ethyl)-5,6-dihydro-pyridin-1(2H)-yl)-2-phenylethanol] which was then subjected to acetylation using pyridine and acetic anhydride. The reaction mixture was kept at RT with occasional shaking. After 4 hours, the solvent was removed in vacuo and the residue was taken up in dichloromethane (15 ml), washed with water (10 ml), dried over $Na_2SO_4$ and the solvent removed in vacuo. Column chromatography of the crude product over silica gel (hexane:ethyl acetate 8:2) yielded the acetylated product.

(R)-2-(4-(2-(benzhydryloxy)ethyl)-5,6-dihydropyridin-1 (2H)-yl)-1-phenylethyl acetate (7a). With reference to FIG. 8, 4-(2-(benzhydryloxy)ethyl)-1,2,3,6-tetrahydropyridine 5 (0.5 g, 1.704 mmol), R-styrene oxide 6a (0.205 g, 1.704 mmol), ethanol (20 ml). Yield (after purification)=0.7 g. For acetylation, the mixture of regioisomers (0.7 g, 1.693 mmol), pyridine (10 ml) and acetic anhydride (0.208 ml, 2.2 mmol, 1.3 equiv). Yield (after purification)=0.26 g. $^1$H-NMR ($CDCl_3$; 400 MHz): 2.03-2.07 (brs, 5H, H-3, $COCH_3$), 2.31-2.34 (t, 2H, J=6.4 Hz, $OCH_2CH_2$), 2.54-2.71 (m, 3H, H-2, NCHHCHOAc), 2.91-2.97 (dd, 1H, J=8.8 Hz, NCHHCHOAc), 3.04 (brs, 2H, H-6), 3.51-3.54 (t, 2H, $OCH_2CH_2$), 5.34 (s, 1H, PhCH(O)Ph), 5.39 (brs, 1H, CH=C), 5.95-5.98 (dd, 1H, CHOAc), 7.03-7.34 (m, 15H, ArH). $[\alpha]^{25}_D$=−20.22° (c=1.05, $CHCl_3$).

(S)-2-(4-(2-(benzhydryloxy)ethyl)-5,6-dihydropyridin-1 (2H)-yl)-1-phenylethyl acetate (7b). With reference to FIG. 8, 4-(2-(benzhydryloxy)ethyl)-1,2,3,6-tetrahydropyridine 5 (0.5 g, 1.704 mmol), S-styrene oxide 6b (0.205 g, 1.704 mmol), ethanol (20 ml). Yield (after purification)=0.65 g. For acetylation, the mixture of regioisomers (0.5 g, 1.209 mmol), pyridine (10 ml) and acetic anhydride (0.148 ml, 1.571 mmol, 1.3 equiv).Yield (after purification)=0.2 g. $^1$H-NMR ($CDCl_3$; 400 MHz): 2.03-2.07 (brs, 5H, H-3, $COCH_3$), 2.31-2.34 (t, 2H, J=6.4 Hz, $OCH_2CH_2$), 2.59-2.74 (m, 3H, H-2, NCHHCHOAc), 2.95-2.30 (dd, 1H, J=9.2 Hz, NCHHCHOAc), 3.04 (brs, 2H, H-6), 3.51-3.54 (t, 2H, $OCH_2CH_2$), 5.33 (s, 1H, PhCH(O)Ph), 5.39 (brs, 1H, CH=C), 5.96-6.00 (dd, 1H, CHOAc), 7.21-7.37 (m, 15H, ArH). $[\alpha]^{25}_D$=+21.17° (c=1.02, $CHCl_3$).

(R)-2-(4-(2-(benzhydryloxy)ethyl)-5,6-dihydropyridin-1 (2H)-yl)-1-(4-fluorophenyl)-ethyl acetate (7c). With reference to FIG. 8, 4-(2-(benzhydryloxy)ethyl)-1,2,3,6-tetrahydropyridine 5 (0.493 g, 1.68 mmol), R-4-fluorostyrene oxide 6c (0.232 g, 1.68 mmol), ethanol (20 ml). Yield (after purification)=0.380 g. For acetylation, the mixture of regioisomers (0.38 g, 0.881 mmol), pyridine (10 ml) and acetic anhydride (0.110 ml, 1.145 mmol, 1.3 equiv). Yield (after purification)= 0.18 g. $^1$H-NMR ($CDCl_3$; 400 MHz): 2.02-2.06 (brs, 5H, H-3, $COCH_3$), 2.30-2.38 (t, 2H, J=6.4 Hz, $OCH_2CH_2$), 2.52-2.69 (m, 3H, H-2, NCHHCHOAc), 2.91-2.96 (dd, 1H, J=8.8 Hz, NCHHCHOAc), 3.04 (brs, 2H, H-6), 3.51-3.55 (t, 2H, $OCH_2CH_2$), 5.37 (s, 1H, PhCH(O)Ph), 5.39 (brs, 1H, CH=C), 5.95-5.98 (dd, 1H, CHOAc), 6.99-7.04 (t, 2H, ArH), 7.21-7.33 (m, 12H, ArH). $[\alpha]^{25}_D$=−24.24° (c=0.77, $CHCl_3$).

(S)-2-(4-(2-(benzhydryloxy)ethyl)-5,6-dihydropyridin-1 (2H)-yl)-1-(4-fluorophenyl)-ethyl acetate (7d). With reference to FIG. 8, 4-(2-(benzhydryloxy)ethyl)-1,2,3,6-tetrahydro pyridine 5 (0.477 g, 1.62 mmol), S-4-fluorostyrene oxide 6d (0.225 g, 1.62 mmol), ethanol (20 ml). Yield (after purification)=0.42 g. For acetylation, the mixture of regioisomers (0.42 g, 0.973 mmol), pyridine (10 ml) and acetic anhydride (0.119 ml, 1.265 mmol, 1.3 equiv). Yield (after purification)= 0.25 g. $^1$H-NMR ($CDCl_3$; 400 MHz): 2.03-2.06 (brs, 5H, H-3, COCH3), 2.305-2.338 (t, 2H, J=6.4 Hz, $OCH_2CH_2$), 2.579-2.73 (m, 3H, H-2, NCHHCHOAc), 2.95-3.00 (dd, 1H, J=8.8 Hz, NCHHCHOAc), 3.04 (brs, 2H, H-6), 3.51-3.54 (t, 2H, $OCH_2CH_2$), 5.33 (s, 1H, PhCH(O)Ph), 5.39 (brs, 1H, CH=C), 5.96-5.99 (dd, 1H, CHOAc), 6.99-7.03 (t, 2H, ArH), 7.23-7.33 (m, 12H, ArH). $[\alpha]^{25}_D$=+24.89° (c=0.83, $CHCl_3$).

General Procedure II. Synthesis of 8A-8D. With reference to FIG. 8, into a stirred solution of $NaBH_4$ in dry THF at 0° C. under $N_2$ was added dropwise 48% w/w $BF_3$-ether complex. The cooling bath was removed, and the solution was allowed to stir for 1 hr at room temperature (RT). The mixture was then cooled in an ice-bath. Into the cooled solution was added dropwise a solution of 8 in THF (10 ml). The solution was brought back to RT and stirred for an additional 2 hrs. The solution was again cooled to 0° C. and water, ethanol and 3N NaOH solution were added followed by dropwise addition of 30% $H_2O_2$. The reaction mixture was stirred at 55° C. overnight, cooled to RT and the solvent evaporated in vacuo. The product was partitioned between water and ethyl acetate. The aqueous layer was extracted with ethyl acetate and the combined organic layers were dried over $Na_2SO_4$ and concentrated to give crude diastereomeric mixture which was chromatographed over silica gel to give pale yellow viscous oil.

Separation of diastereomers 8A-8D. Diastereomeric mixtures 8A-8D were separated by semipreparative HPLC using a normal phase column (Nova-Pack Silica 6 mM). The mobile phase used was either 4 or 5% 2-propanol in hexane with a flow rate of 15 ml/min. Final purity of the separated diastereomers was checked by an analytical normal phase column (Nova-Pack Silica 60 Å 4 mM) using the same mobile phase with a flow rate of 1 ml/min.

Synthesis of (1R)-2-(4-(2-(benzhydryloxy)ethyl)-3-hydroxypiperidin-1-yl)-1-phenyl-ethyl acetate (8A). With reference to FIG. 8, general procedure II was used. The quantities of the chemicals in order of addition are as follows: $NaBH_4$ (0.116 g, 3.08 mmol), THF (20 ml), $BF_3$-ether complex (0.4 ml, 3.265 mmol), (R)-2-(4-(2-(benzhydryloxy) ethyl)-5,6-dihydropyridin-1(2H)-yl)-1-phenylethyl acetate 7a (0.7 g, 1.536 mmol), water (2 ml), ethanol (2 ml), 3N NaOH (1.1 ml) and 30% $H_2O_2$ (0.8 ml, 7.68 mmol).

Separation of diastereomers 8A. In semipreparative HPLC run, with 4% 2-propanol as the mobile phase, the retention times of 8a and 8a' were observed to be 14.31 and 17.96 min., respectively. In case of analytical HPLC, the respective retention times for 8a and 8a' were 4.71 and 5.52 min. Yield of 8a=0.183 g. Yield of 8a'=0.12 g.

(R)-2-((3R,4R)-4-(2-(benzhydryloxy)ethyl)-3-hydroxypiperidin-1-yl)-1-phenylethyl acetate (8a). With reference to FIG. 8, 1H-NMR (CDCl$_3$; 400 MHz): 1.34-1.39 (2H, m, H-4, H-5ax), 1.55-1.66 (2H, m, H-5eq, CH$_2$CH$_2$O), 1.85-1.91 (m, 1H, H-6ax), 1.98-2.03 (t, 1H, J=9.6 Hz, H-2ax), 2.08 (s, 3H, OCOCH3), 2.13-2.19 (t, 1H, J=10.8 Hz, CHHCH$_2$O), 2.56-2.61 (dd, 1H, J=13.6, 4.4 Hz, NCHHCHAr), 2.71-2.73 (brd, 1H, J=11.2 Hz, H-6eq), 2.82-2.88 (m, 1H, NCHHCHAr), 3.05-3.08 (dd, 1H, J=10.4, 3.2 Hz, H-2eq), 3.33-3.38 (m, 1H, H-3ax), 3.48-3.54 (m, 1H, CH2CHHO), 3.55-3.60 (m, 1H, CH2CHHO), 5.36 (s, 1H, PhCH(O)Ph), 5.91-5.95 (dd, 1H, J=8.8, 4.4 Hz, CHOCOCH$_3$), 7.22-7.35 (15H, m, ArH). $[\alpha]^{25}_D$=−12.72° (c=0.99, MeOH).

(R)-2-((3S,4S)-4-(2-(benzhydryloxy)ethyl)-3-hydroxypiperidin-1-yl)-1-phenylethyl acetate (8a'). With reference to FIG. 8, 1H-NMR (CDCl$_3$; 400 MHz): 1.34-1.40 (m, 2H, H-4, H-5ax), 1.54-1.66 (m, 2H, H-5eq, CH2CH2O), 1.82-1.91 (m, 1H, H-6ax), 2.02-2.13 (m, 5H, H-2ax, OCOCH3, CHHCH$_2$O), 2.53-2.58 (dd, 1H, J=13.6, 4 Hz NCHHCHAr), 2.80-2.87 (m, 2H, H-6eq, NCHHCHAr), 2.97-3.01 (dd, 1H, J=10.8, 3.6 Hz, H-2eq), 3.37-3.42 (m, 1H, H-3ax), 3.48-3.53 (m, 1H, CH2CHHO), 3.56-3.60 (m, 1H, CH2CHHO), 5.37 (s, 1H, PhCH(O)Ph), 5.93-5.96 (dd, 1H, J=8.8, 4 Hz, CHOCOCH3), 7.22-7.35 (m, 15H, ArH). $[\alpha]^{25}_D$=−48.76° (c=1.05, MeOH).

Synthesis of (1S)-2-(4-(2-(benzhydryloxy)ethyl)-3-hydroxypiperidin-1-yl)-1-phenyl-ethyl acetate (8B). With reference to FIG. 8, General procedure II was used. The quantities of the chemicals in order of addition are as follows: NaBH$_4$ (0.0191 g, 0.505 mmol), THF (10 ml), BF$_3$-ether complex (0.066 ml, 0.536 mmol), (S)-2-(4-(2-(benzhydryloxy)ethyl)-5,6-dihydropyridin-1(2H)-yl)-1-phenylethyl acetate 7b (0.115 g, 0.252 mmol), water (0.3 ml), ethanol (0.5 ml), 3N NaOH (0.2 ml) and 30% H$_2$O$_2$ (0.2 ml, 1.26 mmol).

Separation of diastereomers 8B. In semipreparative HPLC run, with 5% 2-propanol in hexane as mobile phase, the retention times of 8b' and 8b were observed to be 13.57 and 18.15 min., respectively. In case of analytical HPLC, the respective retention times for 8b' and 8b were 3.71 and 4.37 min. Yield of 8b'=0.03 g. Yield of 8b=0.03 g. (S)-2-((3S,4S)-4-(2-(benzhydryloxy)ethyl)-3-hydroxypiperidin-1-yl)-1-phenylethyl acetate (8b'). $^1$H-NMR (CDCl3; 400 MHz): 1.30-1.38 (m, 2H, H-4, H-5ax), 1.54-1.66 (m, 2H, H-5eq, CH2CH2O), 1.84-1.91 (m, 1H, H-6ax), 1.98-2.03 (t, 1H, J=9.6 Hz, H-2ax), 2.08 (s, 3H, OCOCH3), 2.13-2.19 (t, 1H, J=10.8 Hz, CHHCH2O), 2.56-2.61 (dd, 1H, J=13.2, 4 Hz NCHHCHAr), 2.71-2.74 (brd, 1H, J=11.6 Hz, H-6eq), 2.82-2.88 (m, 1H, NCHHCHAr), 3.05-3.08 (dd, 1H, J=10.4, 2.8 Hz, H-2eq), 3.33-3.38 (m, 1H, H-3ax), 3.48-3.53 (m, 1H, CH$_2$CHHO), 3.55-3.60 (m, 1H, CH$_2$CHHO), 5.36 (s, 1H, PhCH(O)Ph), 5.91-5.95 (dd, 1H, J=8.8, 4.4 Hz, CHOCOCH$_3$), 7.22-7.35 (m, 15H, ArH). $[\alpha]^{25}_D$=+12.98° (c=1.47, CHCl$_3$).

(S)-2-((3R,4R)-4-(2-(benzhydryloxy)ethyl)-3-hydroxypiperidin-1-yl)-1-phenylethyl acetate (8b). This preparation was performed in accordance with FIG. 8: $^1$H-NMR (CDCl$_3$; 400 MHz): 1.30-1.39 (m, 2H, H-4, H-5ax), 1.55-1.66 (m, 2H, H-5eq, CH$_2$CH$_2$O), 1.82-1.92 (m, 1H, H-6ax), 2.02-2.13 (m, 5H, H-2ax, OCOCH$_3$, CHHCH$_2$O), 2.54-2.58 (dd, 1H, J=13.6, 4 Hz NCHHCHAr), 2.80-2.87 (m, 2H, H-6eq, NCHHCHAr), 2.97-3.01 (dd, 1H, J=10.8, 3.2 Hz, H-2eq), 3.37-3.42 (m, 1H, H-3ax), 3.48-3.53 (m, 1H, CH$_2$CHHO), 3.56-3.61 (m, 1H, CH$_2$CHHO), 5.37 (s, 1H, PhCH(O)Ph), 5.93-5.96 (dd, 1H, J=8.8, 4 Hz, CHOCOCH$_3$), 7.22-7.35 (m, 15H, ArH). $[\alpha]^{25}_D$=−48.76° (c=1.05, MeOH).

Synthesis of (1R)-2-(4-(2-(benzhydryloxy)ethyl)-3-hydroxypiperidin-1-yl)-1-(4-fluo-rophenyl)ethyl acetate (8C). With reference to FIG. 8, general procedure II was used. The quantities of the chemicals in order of addition are as follows: NaBH$_4$ (0.029 g, 0.762 mmol), THF (10 ml), BF$_3$-ether complex (0.1 ml, 0.81 mmol), (R)-2-(4-(2-(benzhydryloxy)ethyl)-5,6-dihydropyridin-1(2H)-yl)-1-(4-fluorophenyl)ethyl acetate 7c (0.180 g, 0.38 mmol), water (0.3 ml), ethanol (0.4 ml), 3N NaOH (0.3 ml) and 30% H$_2$O$_2$ (0.2 ml, 1.9 mmol).

Separation of diastereomers 8C. With reference to FIG. 8, in semipreparative HPLC run, with 5% 2-propanol in hexane as mobile phase, the retention times of 8c and 8c' were observed to be 13.35 and 18.49 min., respectively. In case of analytical HPLC, the respective retention times for 8c and 8c' were 3.92 and 4.41 min. Yield of 8c=0.026 g. Yield of 8c'=0.023 g.

(R)-2-((3R,4R)-4-(2-(benzhydryloxy)ethyl)-3-hydroxypiperidin-1-yl)-1-(4-fluorophen-yl)ethyl acetate (8c). $^1$H-NMR (CDCl$_3$; 400 MHz): 1.28-1.38 (m, 2H, H-4, H-5ax), 1.54-1.65 (2H, m, H-5eq, CH$_2$CH$_2$O), 1.83-1.92 (m, 1H, H-6ax), 1.97-2.0 (t, 1H, J=10 Hz, H-2ax), 2.07 (s, 3H, OCOCH$_3$), 2.12-2.17 (t, 1H, J=9.2 Hz, CHHCH$_2$O), 2.54-2.58 (dd, 1H, J=13.6, 4.4 Hz, NCHHCHAr), 2.71-2.73 (brd, 1H, J=11.6 Hz, H-6eq), 2.80-2.85 (m, 1H, NCHHCHAr), 3.01-3.05 (dd, 1H, J=10.4, 3.6 Hz, H-2eq), 3.31-3.37 (m, 1H, H-3ax), 3.48-3.54 (m, 1H, CH$_2$CHHO), 3.57-3.61 (m, 1H, CH$_2$CHHO), 5.37 (s, 1H, PhCH(O)Ph), 5.87-5.90 (dd, 1H, J=8.4, 4.8 Hz, CHOCOCH$_3$), 7.00-7.04 (t, 2H, ArH), 7.23-7.33 (m, 12H, ArH). $[\alpha]^{25}_D$=−12.95° (c=1.0, CHCl$_3$).

(R)-2-((3S,4S)-4-(2-(benzhydryloxy)ethyl)-3-hydroxypiperidin-1-yl)-1-(4-fluorophen-yl)ethyl acetate (8c'). $^1$H-NMR (CDCl$_3$; 400 MHz): 1.31-1.40 (m, 2H, H-4, H-5ax), 1.55-1.65 (m, 2H, H-5eq, CH$_2$CH$_2$O), 1.82-1.91 (m, 1H, H-6ax), 2.01-2.14 (m, 5H, H-2ax, OCOCH$_3$, CHHCH$_2$O), 2.51-2.56 (dd, 1H, J=13.6, 3.6 Hz, NCHHCHAr), 2.76-2.84 (m, 2H, H-6eq, NCHHCHAr), 2.98-3.01 (dd, 1H, J=10.8, 3.2 Hz, H-2eq), 3.36-3.41 (m, 1H, H-3ax), 3.48-3.53 (m, 1H, CH$_2$CHHO), 3.56-3.61 (m, 1H, CH$_2$CHHO), 5.37 (s, 1H, PhCH(O)Ph), 5.89-5.92 (dd, 1H, J=8.8, 4.4 Hz, CHOCOCH$_3$), 6.97-7.05 (t, 2H, ArH), 7.23-7.33 (m, 12H, ArH). $[?]^{25}_D$=−36.33° (c=0.9, CHCl$_3$).

Synthesis of (1S)-2-(4-(2-(benzhydryloxy)ethyl)-3-hydroxypiperidin-1-yl)-1-(4-fluo-rophenyl)ethyl acetate (8D). With reference to FIG. 8, general procedure II was used. The quantities of the chemicals in order of addition are as follows: NaBH$_4$ (0.04 g, 1.06 mmol), THF (10 ml), BF$_3$-ether complex (0.14 ml, 1.12 mmol), (S)-2-(4-(2-(benzhydryloxy)ethyl)-5, 6-dihydropyridin-1(2H)-yl)-1-(4-fluorophenyl)ethyl acetate 7d (0.25 g, 0.53 mmol), water (0.4 ml), ethanol (0.6 ml), 3N NaOH (0.4 ml) and 30% H$_2$O$_2$ (0.4 ml, 4.11 mmol).

Separation of diastereomers 8D. In semipreparative HPLC run, with 5% 2-propanol in hexane as mobile phase, the retention times of 8d' and 8d were observed to be 13.4 and 17.69 min., respectively. In case of analytical HPLC, the respective retention times for 8d' and 8b were 3.41 and 4.23 min. Yield of 8d'=0.02 g. Yield of 8d=0.02 g.

(S)-2-((3S,4S)-4-(2-(benzhydryloxy)ethyl)-3-hydroxypiperidin-1-yl)-1-(4-fluorophen-yl)ethyl acetate (8d'). $^1$H-NMR (CDCl$_3$; 400 MHz): 1.28-1.38 (m, 2H, H-4, H-5ax), 1.54-1.65 (2H, m, H-5eq, CH$_2$CH$_2$O), 1.83-1.92 (m, 1H, H-6ax), 1.97-1.99 (t, 1H, J=13.2 Hz, H-2ax), 2.07 (s, 3H, OCOCH$_3$), 2.11-2.14 (t, 1H, J=8.8 Hz, CHHCH$_2$O), 2.54-2.58 (dd, J=13.6, 4.8 Hz, 1H, NCHHCHAr), 2.70-2.73 (brd, 1H, J=11.2 Hz, H-6eq), 2.79-2.85 (m, 1H, NCHHCHAr), 3.01-3.05 (dd, 1H, J=10.4, 2.8 Hz, H-2eq), 3.31-3.36 (m, 1H, H-3ax), 3.48-3.53 (m, 1H, CH$_2$CHHO), 3.55-3.60 (m, 1H, CH$_2$CHHO), 5.36 (s, 1H, PhCH(O)Ph), 5.87-5.90 (dd, 1H, J=8.4, 4.8 Hz, CHOCOCH₃), 6.99-7.04 (t, 2H, ArH), 7.22-7.33 (m, 12H, ArH). [a]²⁵_D=+13.30° (c=1.0, CHCl₃).

(S)-2-((3R,4R)-4-(2-(benzhydryloxy)ethyl)-3-hydroxypiperidin-1-yl)-1-(4-fluorophen-yl)ethyl acetate (8d). ¹H-NMR (CDCl₃; 400 MHz): 1.31-1.40 (m, 2H, H-4, H-5ax), 1.54-1.64 (2H, m, H-5eq, CH₂CH₂O), 1.82-1.91 (m, 1H, H-6ax), 2.01-2.12 (m, 5H, H-2ax, OCOCH₃, CHHCH₂O), 2.51-2.56 (dd, 1H, J=13.2, 4.4 Hz, NCHHCHAr), 2.76-2.84 (m, 2H, H-6eq, NCHHCHAr), 2.97-3.01 (dd, 1H, J=10.8, 3.2 Hz, H-2eq), 3.35-3.40 (m, 1H, H-3ax), 3.48-3.53 (m, 1H, CH₂CHHO), 3.56-3.61 (m, 1H, CH₂CHHO), 5.37 (s, 1H, PhCH(O)Ph), 5.89-5.92 (dd, 1H, J=8.8, 4.4 Hz, CHOCOCH₃), 6.99-7.03 (t, 2H, ArH), 7.22-7.33 (m, 12H, ArH). [a]²⁵_D=+36.5° (c=1.0, CHCl₃).

Figure 9:
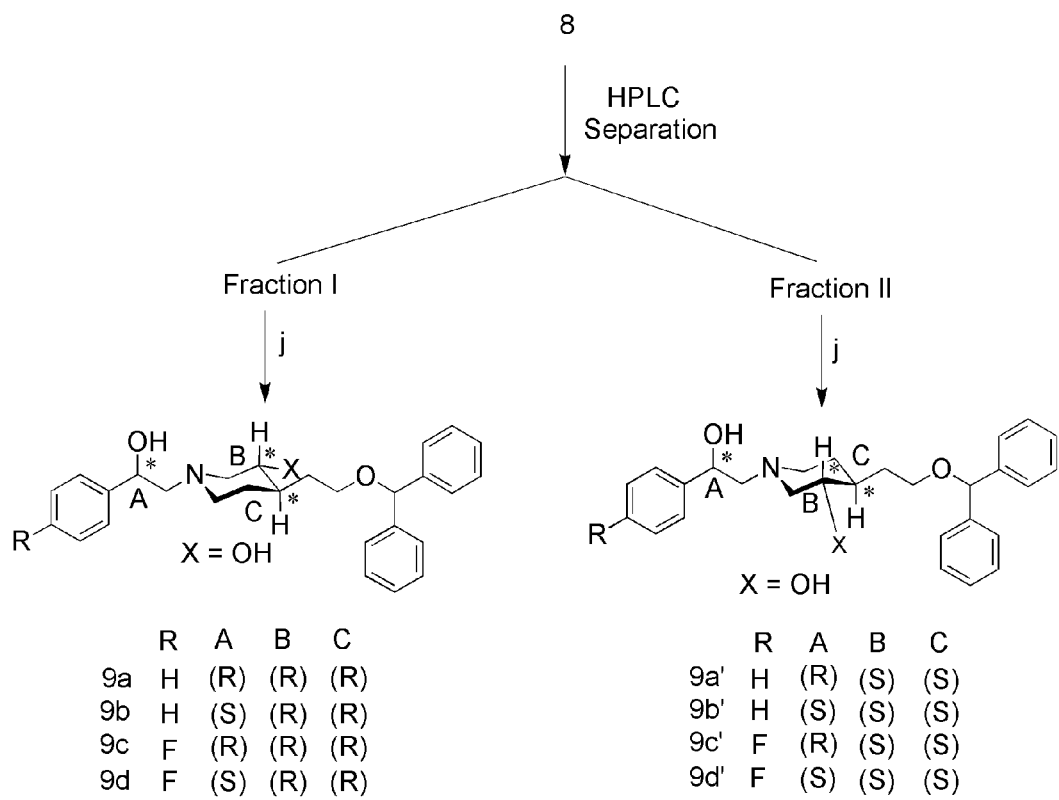
FIG. 9 illustrates another synthesis scheme and the structures of certain of the subject invention compounds.

General Procedure III. Synthesis of 9a-9d, 9a'-9d'. With reference to FIG. 9, fractions I and II obtained from HPLC separation were individually deacetylated with anhydrous K₂CO₃ (0.56 equivalent) in methanol (15 ml) at room temperature for 4 hrs. Methanol was removed in vacuo, and the residue was partitioned between dichloromethane and water. The organic layer was separated and aqueous layer was further extracted with dichloromethane (2×20 ml). Combined organic layers were dried over anhydrous Na₂CO₃ and concentrated. The crude product was chromatographed over silica gel (ethyl acetate, ethyl acetate:methanol 9:1, methanol).

Synthesis of (3R,4R)-4-(2-(benzhydryloxy)ethyl)-1-((R)-2-hydroxy-2-phenylethyl)-piperidin-3-ol (9a) (D-225). With reference to FIG. 9, fraction I, i.e., 8a (0.183 g, 0.386 mmol) from HPLC separation of diastereomeric mixture 8A was treated with anhydrous K₂CO₃ (30 mg, 0.216 mmol) in methanol to produce 9a (0.15 g). ¹H-NMR (CDCl₃; 400 MHz): 1.39-1.46 (m, 2H, H-4, H-5ax), 1.59-1.66 (m, 2H, H-5eq, CHHCH₂O), 1.87-1.94 (m, 2H, H-2ax, CHHCH₂O), 2.22-2.31 (t, 1H, J=10.8 Hz, H6-ax), 2.44-2.53 (m, 2H, NCH₂CHAr), 2.70-2.73 (brd, 1H, J=11.2 Hz, H-6eq), 3.30-3.34 (dd, 1H, J=10.8, 3.2 Hz, H-2eq), 3.40-3.46 (m, 1H, H-3ax), 3.51-3.57 (m, 1H, CH₂CHHO), 3.60-3.65 (m, 1H, CH₂CHHO), 4.72-4.76 (dd, 1H, J=10, 4 Hz, CH₂CH(OH)Ar), 5.39 (s, 1H, PhCH(O)Ph), 7.24-7.35 (m, 15H, ArH). [a]²⁵_D=−12.48° (c=1.0, CHCl₃). The free base was converted to oxalate salt, mp154-156° C. Analysis calculated for C₂₈H₃₃NO₃.(COOH)₂.0.9H₂O) C, H, N.

Synthesis of (3S,4S)-4-(2-(benzhydryloxy)ethyl)-1-((R)-2-hydroxy-2-phenylethyl)-piperidin-3-ol (9a') (D-226). With reference to FIG. 9, fraction II, i.e., 8a' (0.12 g, 0.253 mmol) from HPLC separation of diastereomeric mixture 8A was treated with anhydrous K₂CO₃ (20 mg, 0.142 mmol) in methanol to produce 9a' (0.08 g). ¹H-NMR (CDCl₃; 400 MHz): 1.32-1.43 (m, 2H, H-4, H-5ax), 1.60-1.71 (m, 2H, H-5eq, CHHCH₂O), 1.88-2.01 (m, 2H, H-2ax, CHHCH₂O), 2.12-2.18 (t, 1H, J=10.4 Hz, H-6ax), 2.43-2.55 (m, 2H, NCH₂CHAr), 2.98-3.01 (dd, 1H, J=11.2, 3.2 Hz, H-2eq), 3.04-3.07 (brd, 1H, J=10.8 Hz, H-6eq), 3.43-3.48 (m, 1H, H-3ax), 3.52-3.57 (m, 1H, CH₂CHHO), 3.60-3.65 (m, 1H, CH₂CHHO), 4.70-4.73 (dd, 1H, J=10.4, 3.6 Hz, CH₂CH(OH)Ar), 5.39 (s, 1H, PhCH(O)Ph), 7.24-7.36 (m, 15H, ArH). [a]²⁵_D=−50.73° (c=0.95, CHCl₃). The free base was converted to oxalate salt, mp 84-86° C. Analysis calculated for (C₂₈H₃₃NO₃.(COOH)₂.0.4H₂O) C, H, N.

Synthesis of (3S,4S)-4-(2-(benzhydryloxy)ethyl)-1-((S)-2-hydroxy-2-phenylethyl)-piperidin-3-ol(9b') (D-275). With reference to FIG. 9, fraction I, i.e., 8b' (0.03 g, 0.063 mmol) from HPLC separation of diastereomeric mixture 8B was treated with anhydrous K₂CO₃ (5 mg, 0.035 mmol) in methanol to produce 9b' (0.025 g). ¹H-NMR (CDCl₃; 400 MHz): 1.38-1.44 (m, 2H, H-4, H-5ax), 1.60-1.67 (m, 2H, H-5eq, CHHCH₂O), 1.87-1.94 (m, 2H, H-2ax, CHHCH₂O), 2.22-2.27 (dt, 1H, J=11.2 Hz, H6-ax), 2.43-2.53 (m, 2H, NCH₂CHAr), 2.69-2.72 (brd, 1H, J=10.8 Hz, H-6eq), 3.30-3.34 (dd, 1H, J=10.8, 3.2 Hz, H-2eq), 3.40-3.46 (m, 1H, H-3ax), 3.51-3.57 (m, 1H, CH₂CHHO), 3.60-3.64 (m, 1H, CH₂CHHO), 4.72-4.75 (dd, 1H, J=9.6, 4 Hz, CH₂CH(OH)Ar), 5.39 (s, 1H, PhCH(O)Ph), 7.24-7.34 (m, 15H, ArH). [a]²⁵_D=+13.33° (c=0.96, CHCl₃). The free base was converted to oxalate salt, mp152-154° C. Analysis calculated for (C₂₈H₃₃NO₃.(COOH)₂) C, H, N.

Synthesis of (3R,4R)-4-(2-(benzhydryloxy)ethyl)-1-((S)-2-hydroxy-2-phenylethyl)-piperidin-3-ol (9b) (D-276). With reference to FIG. 9, fraction II, i.e., 8b (0.03 g, 0.063 mmol) from HPLC separation of diastereomeric mixture 8B was treated with anhydrous K₂CO₃ (5 mg, 0.035 mmol) in methanol to produce 9b (0.025 g). ¹H-NMR (CDCl₃; 400 MHz): 1.32-1.43 (m, 2H, H-4, H-5ax), 1.60-1.71 (m, 2H, H-5eq, CHHCH₂O), 1.87-2.01 (m, 2H, H-2ax, CHHCH₂O), 2.12-2.17 (t, 1H, J=10.4 Hz, H6-ax), 2.43-2.54 (m, 2H, NCH₂CHAr), 2.98-3.01 (dd, 1H, J=10.8, 3.2 Hz, H-2eq), 3.04-3.07 (brd, 1H, J=10.4 Hz, H-6eq), 3.43-3.48 (m, 1H, H-3ax), 3.51-3.57 (m, 1H, CH₂CHHO), 3.60-3.64 (m, 1H, CH₂CHHO), 4.70-4.73 (dd, 1H, J=10.4, 3.6 Hz, CH₂CH(OH)Ar), 5.39 (s, 1H, PhCH(O)Ph), 7.23-7.37 (m, 15H, ArH). [a]²⁵_D=+50.64° (c=0.95, CHCl₃). The free base was converted to oxalate salt, mp 82-84° C. Analysis calculated for (C₂₈H₃₃NO₃.(COOH)₂.0.7H₂O) C, H, N.

Synthesis of (3R,4R)-4-(2-(benzhydryloxy)ethyl)-1-((R)-2-(4-fluorophenyl)-2-hydro-xyethyl)piperidin-3-ol (9c) (D-231). With reference to FIG. 9, fraction I, i.e., 8c (0.026 g, 0.053 mmol) from HPLC separation of diastereomeric mixture 8C was treated with anhydrous K₂CO₃ (4.1 mg, 0.03 mmol) in methanol to produce 9a (0.02 g). ¹H-NMR (CDCl₃; 400 MHz): 1.39-1.42 (m, 2H, H-4, H-5ax), 1.61-1.67 (m, 2H, H-5eq, CHHCH₂O), 1.87-1.95 (m, 2H, H-2ax, CHHCH₂O), 2.23-2.28 (t, 1H, J=11.2 Hz, H6-ax), 2.40-2.50 (m, 2H, NCH₂CHAr), 2.70-2.73 (brd, 1H, J=11.2 Hz, H-6eq), 3.29-3.33 (dd, 1H, J=10.4, 3.2 Hz, H-2eq), 3.40-3.46 (m, 1H, H-3ax), 3.52-3.57 (m, 1H, Hz, CH₂CHHO), 3.60-3.65 (m, 1H, CH₂CHHO), 4.70-4.73 (dd, 1H, J=10.4, 3.6 Hz, CH₂CH(OH)Ar), 5.39 (s, 1H, PhCH(O)Ph), 7.00-7.04 (t, 2H, ArH), 7.23-7.34 (m, 12H, ArH). [a]²⁵_D=−13.84° (c=0.65, CHCl₃). The free base was converted to oxalate salt, mp160-162° C. Analysis calculated for C₂₈H₃₂FNO₃.(COOH)₂.0.1H₂O) C, H, N.

Synthesis of (3S,4S)-4-(2-(benzhydryloxy)ethyl)-1-((R)-2-(4-fluorophenyl)-2-hydro-xyethyl)piperidin-3-ol (9c') (D-230). With reference to FIG. 9, Fraction II, i.e., 8c' (0.023 g, 0.047 mmol) from HPLC separation of diastereomeric mixture 8C was treated with anhydrous K₂CO₃ (3.6 mg, 0.026 mmol) in methanol to produce 9c' (0.02 g). ¹H-NMR (CDCl₃; 400 MHz): 1.34-1.41 (m, 2H, H-4, H-5ax), 1.61-1.71 (m, 2H, H-5eq, CHHCH₂O), 1.88-2.00 (m, 2H, H-2ax, CHHCH₂O), 2.13-2.18 (t, 1H, J=10 Hz, H6-ax), 2.38-2.52 (m, 2H, NCH₂CHAr), 2.97-3.01 (dd, 1H, J=12, 3.6 Hz, H-2eq), 3.02-3.05 (brd, 1H, J=10.8 Hz, H-6eq), 3.43-3.49 (m, 1H, H-3ax), 3.52-3.57 (m, 1H, CH₂CHHO), 3.60-3.65 (m, 1H, CH₂CHHO), 4.67-4.71 (dd, 1H, J=10.4, 3.2 Hz, CH₂CH(OH)Ar), 5.39 (s, 1H, PhCH(O)Ph), 7.00-7.04 (t, 2H, ArH), 7.24-7.36 (m, 12H, ArH). [a]²⁵_D=−45.78° (c=0.95, CHCl₃). The free base was converted to oxalate salt, mp 82-84° C. Analysis calculated for C₂₈H₃₂FNO₃.(COOH)₂.0.7H₂O) C, H, N.

Synthesis of (3S,4S)-4-(2-(benzhydryloxy)ethyl)-1-((S)-2-(4-fluorophenyl)-2-hydro-xyethyl)piperidin-3-ol (9d') (D-233). With reference to FIG. 9, fraction I, i.e., 8d' (0.02 g, 0.04 mmol) from HPLC separation of diastereomeric mixture 8D was treated with anhydrous $K_2CO_3$ (3.1 mg, 0.022 mmol) in methanol to produce 9d' (0.017 g). $^1$H-NMR (CDCl$_3$; 400 MHz): 1.40-1.51 (m, 2H, H-4, H-5ax), 1.60-1.70 (m, 2H, H-5eq, CHHCH$_2$O), 1.87-1.98 (m, 2H, H-2ax, CHHCH$_2$O), 2.26-2.31 (t, 1H, J=11.2 Hz, H6-ax), 2.46-2.51 (m, 2H, NCH$_2$CHAr), 2.77-2.80 (brd, 1H, J=12 Hz, H-6eq), 3.33-3.37 (dd, 1H, J=10.4, 3.2 Hz, H-2eq), 3.44-3.50 (m, 1H, H-3ax), 3.52-3.57 (m, 1H, CH$_2$CHHO), 3.61-3.65 (m, 1H, CH$_2$CHHO), 4.74-4.78 (t, 1H, J=6.8 Hz, CH$_2$CH(OH)Ar), 5.39 (s, 1H, PhCH(O)Ph), 7.00-7.04 (t, 2H, ArH), 7.24-7.35 (m, 12H, ArH). $[\alpha]^{25}_D$=+14.3 (c=0.65, CHCl$_3$). The free base was converted to oxalate salt, mp164-166° C. Analysis calculated for $C_{28}H_{32}FNO_3 \cdot (COOH)_2 \cdot 0.1H_2O$ C, H, N.

Synthesis of (3R,4R)-4-(2-(benzhydryloxy)ethyl)-1-((S)-2-(4-fluorophenyl)-2-hydro-xyethyl)piperidin-3-ol (9d) (D-232). With reference to FIG. 9, fraction II, i.e., 8d (0.02 g, 0.04) from HPLC separation of diastereomeric mixture 8D was treated with anhydrous $K_2CO_3$ (3.1 mg, 0.022 mmol) in methanol to produce 9c' (0.017 g). $^1$H-NMR (CDCl$_3$; 400 MHz): 1.33-1.39 (m, 2H, H-4, H-5ax), 1.61-1.71 (m, 2H, H-5eq, CHHCH$_2$O), 1.88-2.00 (m, 2H, H-2ax, CHHCH$_2$O), 2.12-2.17 (t, 1H, J=10.4 Hz, H6-ax), 2.38-2.51 (m, 2H, NCH$_2$CHAr), 2.97-3.00 (dd, 1H, J=11.2, 4 Hz, H-2eq), 3.02-3.05 (brd, 1H, J=11.2 Hz, H-6eq), 3.42-3.48 (m, 1H, H-3ax), 3.52-3.57 (m, 1H, CH$_2$CHHO), 3.60-3.65 (m, 1H, CH$_2$CHHO), 4.67-4.70 (dd, 1H, J=10.4, 3.2 Hz, CH$_2$CH(OH)Ar), 5.39 (s, 1H, PhCH(O)Ph), 7.00-7.04 (t, 2H, ArH), 7.23-7.34 (m, 12H, ArH). $[\alpha]^{25}_D$=+43. 13° (c=0.8, CHCl$_3$). The free base was converted to oxalate salt, mp 84-86° C. Analysis calculated for $C_{28}H_{32}FNO_3 \cdot (COOH)_2 \cdot 0.7H_2O$ C, H, N.

Figure 14:
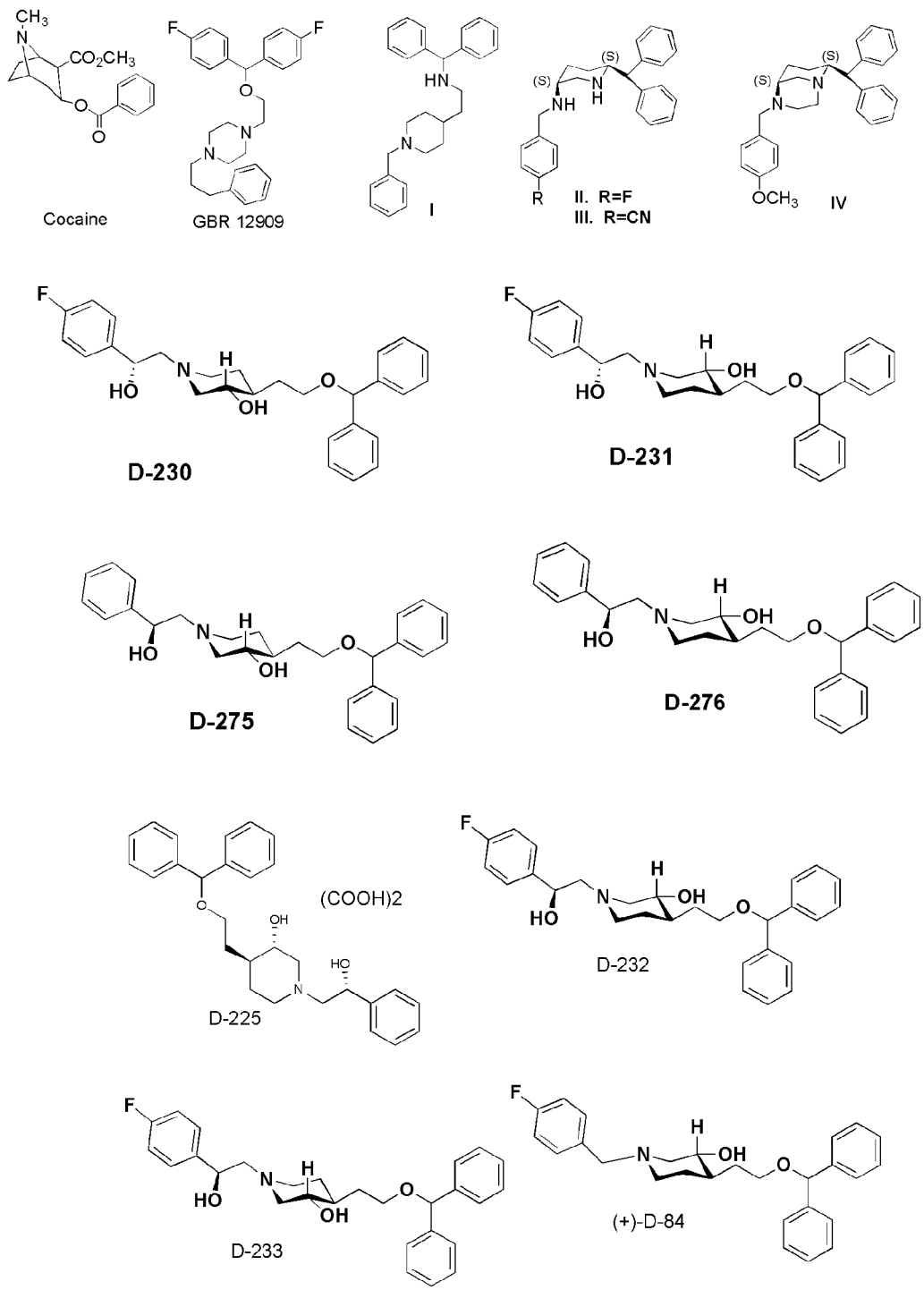
FIG. 14 provides a chemical structure of compounds relevant to embodiments of the invention.

Table 6 (FIG. 13) provides the affinity of hydroxypiperidine derivatives described by FIGS. 7, 8, and 9 at the DAT, SERT, and NET in rat brain. FIG. 14 provides the structure of GBR 12909.

IV. Synthesis of the Compounds of FIG. 10 Through 12.

Analytical silica gel-coated TLC plates (Si 250 F) were purchased from Baker, Inc and were visualized with UV light or by treatment with phosphomolybdic acid (PMA). Flash chromatography was carried out on Baker Silica Gel 40 mM. $^1$H NMR spectra were routinely obtained at Varian 400 MHz FT NMR. The NMR solvent used was CDCl$_3$ as indicated. TMS was used as an internal standard. Elemental analyses were performed by Atlantic Microlab, Inc and were within ±0.4% of the theoretical value. Optical rotations were measured on Perkin-Elmer 241 polarimeter.

[$^3$H]WIN 35,428 (83.6 Ci/mmol), [$^3$H]dopamine (55.1 Ci/mmol), [3H]serotonin (30.0 Ci/mmol), and [$^3$H]norepinephrine (54.6 Ci/mmol) were obtained from Dupont-New England Nuclear (Boston, Mass., U.S.A). WIN 35,428 napthalene sulfonate was purchased from Research Biochemicals, Inc. (Natick, Mass., U.S.A.). (−)-Cocaine HCl was obtained from the National Institute on Drug Abuse. GBR 12909 Dihydrochloride (1-[2-[bis(4-Fluorophenyl)methoxy]ethyl]-4-[3-phenylpropyl]piperazine) was purchased from SIGMA-ALDRICH (#D-052; St. Louis, Mo.).

Synthesis of N-(6-benzhydrylpiperidin-3-yl)-4,7,7-trimethyl-3-oxo-2-oxa-bicyclo[2.2.1]heptane-1-carboxamide (2a and 2b). To a stirring solution of racemic cis-6-benzhydrylpiperidin-3-ylamine 1 (1.10 g, 4.12 mmol) in anhydrous CH$_2$Cl$_2$ (50 ml), triethylamine (2.08 g, 20.64 mmol) was added drop wise (1S)-(−)-camphanic chloride (1.07 g, 4.95 mmol) dissolved in 10 ml anhydrous CH$_2$Cl$_2$ under nitrogen. The reaction mixture was stirred at 0° C. for 30 min and at room temperature for another 3 h under nitrogen atmosphere. The reaction mixture was then diluted with CH$_2$Cl$_2$ (50 ml) and washed with water (20 ml), dried over Na$_2$SO$_4$ and the solvent was evaporated in vacuo to afford a mixture of two diastereomers 2a and 2b. Each diastereoisomer was separated by flash column chromatography over silica gel using hexanes/diethyl ether (12:88) as a mobile phase.

Eluting first was 2a (0.51 g, 55%) $^1$H NMR (400 MHz, CDCl$_3$): δ 0.89 (3H, s, CH$_3$), 1.09 (3H, s, CH$_3$), 1.11 (3H, s, CH$_3$), 1.37-1.41 (1H, m, H-5), 1.48-1.56 (1H, m, H-5), 1.65-1.72 (2H, m, CCH$_2$C), 1.82-1.97 (3H, m, CCH$_2$C and H-4), 2.48-2.56 (1H, m, H-4), 2.78-2.84 (2H, m, H-2), 3.23 (1H, dt, J=2.4 Hz, J=10.4 Hz, H-6), 3.79 (1H, d, J=10.0 Hz, (Ph)$_2$CH), 4.09-4.12 (1H, m, H-3), 7.13-7.37 (8H, m, ArH), 7.39-7.41 (2H, m, ArH).

Eluting second was 2b (0.45 g, 49%) $^1$H NMR (400 MHz, CDCl$_3$): δ 0.82 (3H, s, CH$_3$), 1.02 (3H, s, CH$_3$), 1.05 (3H, s, CH$_3$), 1.32-1.35 (1H, m, H-5), 1.43-1.52 (1H, m, H-5), 1.57-1.64 (2H, m, CCH$_2$C), 1.71-1.90 (3H, m, CCH$_2$C and H-4), 2.41-2.50 (1H, m, H-4), 2.71-2.80 (2H, m, H-2), 3.16 (1H, dt, J=2.0 Hz, J=10.4 Hz, H-6), 3.71 (1H, d, J=10.0 Hz, (Ph)$_2$CH), 4.01-4.07 (1H, m, H-3), 7.07-7.30 (8H, m, ArH), 7.33-7.35 (2H, m, ArH).

Synthesis of (−)-cis-6-Benzhydrylpiperidin-3-ylamine (3). A solution of 2b (0.55 g, 1.23 mmol) in conc. HCl/MeOH (50 ml, 1:4 ratio v/v) was refluxed for 72 h. Methanol was then evaporated under reduced pressure at 50° C. and the remaining aqueous solution was neutralized by saturated NaHCO$_3$ solution. The solution was extracted with CH$_2$Cl$_2$ (3×50 ml). All organic layers were combined, washed with brine (50 ml) and dried over Na$_2$SO$_4$, concentrated and purified by flash column chromatography over silica gel using ethyl acetate/MeOH/Et$_3$N (80:15:5) to afford 3 as a white solid (0.26 g, 79%). $^1$H NMR (400 MHz, CDCl$_3$): δ 1.35-1.43 (2H, m, H-5), 1.59-1.64 (2H, m, H-4), 2.18 (2H, broad singlet, NH), 2.79-2.81 (2H, m, H-2), 2.98-3.04 (1H, m, H-3), 3.25 (1H, dt, J=4 Hz, J=10 Hz, H-6$_{ax}$), 3.80 (1H, d, J=10.2 Hz, (Ph)$_2$CH), 7.12-7.40 (10H, m, ArH). $[\alpha]^{25}_D$=(−) 41.9° (c 1, MeOH).

Procedure A. Synthesis of (R)-2-[(3S,6S)-6-benzhydrylpiperidin-3-ylamino)-1-(4-fluorophenyl)ethanol (4a). To a stirring solution of (−)-cis-6-benzhydrylpiperidin-3-ylamine 3 (0.058 g, 0.217 mmol) in dry ethanol (20 ml), was added R-(−)-4-fluoro styrene oxide (0.045 g, 0.326 mmol). The reaction mixture was refluxed overnight under nitrogen atmosphere. The solvent was evaporated and the product was purified by flash column chromatography over silica gel using diethyl ether/MeOH/Et$_3$N (92:8:0.2) to give 4a (0.023 g, 26%). $^1$H NMR (400 MHz, CDCl$_3$): δ 1.30-1.38 (2H, m, H-5), 1.48-1.55 (1H, m, H-4$_{ax}$), 1.75-1.79 (1H, m, H-4$_{eq}$), 2.44-2.54 (1H, dd, J=2.0 Hz, J=10.0 Hz, NHCH$_2$), 2.71-2.78 (2H, m, H-2), 2.86-2.90 (1H, dd, J=3.2 Hz, J=12.4 Hz, NHCH$_2$), 2.97-3.00 (1H, m, H-3eq), 3.25 (1H, dt, J=3.2 Hz, J=9.6 Hz, H-6$_{ax}$), 3.75 (1H, d, J=10 Hz, (Ph)$_2$CH), 4.60-4.64 (1H, dd, J=3.2 Hz, J=9.6 Hz, CH—OH), 7.01 (2H, t, J=8.4 Hz, ArH), 7.13-7.37 (12H, m, ArH). Free base converted into oxalate salt, m.p. 202-204° C. $[\alpha]^{25}_D$ (oxalate salt)=(−) 21.5° (c 0.26, MeOH).

Analysis calculated for $(C_{26}H_{29}FN_2O \cdot 2(COOH)_2 \cdot 0.5H_2O)$ C, H, N.

Synthesis of (S)-2-[(3S,6S)-6-benzhydrylpiperidin-3-ylamino)-1-(4-fluorophenyl)ethanol (4b). Compound 3

(0.076 g, 0.285 mmol) was refluxed with S-(+)-4-fluoro styrene oxide (0.059 g, 0.427 mmol) (Procedure A) to yield 4b (0.029 g, 25%). $^1$H NMR (400 MHz, CDCl$_3$): δ 1.25-1.38 (2H, m, H-5), 1.47-1.53 (1H, m, H-4$_{ax}$), 1.79-1.83 (1H, m, H4$_{eq}$), 2.43-2.53 (1H, dd, J=2.8 Hz, J=12.0 Hz, NHCH$_2$), 2.71-2.74 (2H, m, H-2), 2.87-2.97 (2H, m, NHCH$_2$ and H-3$_{eq}$), 3.25 (1H, dt, J=3.2 Hz, J=9.6 Hz, H-6$_{ax}$), 3.74 (1H, d, J=10 Hz, (Ph)$_2$CH), 4.60-4.63 (1H, dd, J=2.8 Hz, J=8.8 Hz, CH—OH), 7.01 (2H, t, J=8.8 Hz, ArH), 7.16-7.37 (12H, m, ArH). [α]$^{25}_D$ (oxalate salt)=(+) 19.2° (c 0.38, MeOH). Free base was converted into oxalate salt 203-205° C.

Analysis calculated for (C$_{26}$H$_{29}$FN$_2$O. 2(COOH)$_2$, 0.9H$_2$O) C, H, N.

Synthesis of (R)-1-[(3S,6S)-6-benzhydrylpiperidin-3-ylamino)-3-phenylpropan-2-ol (4c). Compound 3 (0.076 g, 0.285 mmol) was reacted with R-(+)-2,3-epoxypropyl benzene (0.057 g, 0.427 mmol) (Procedure A). The crude product was purified by flash column chromatography using diethyl ether/MeOH/Et$_3$N (90:10:0.2) to give 4c (0.035 g, 30%). $^1$H NMR (400 MHz, CDCl$_3$): δ 1.25-1.34 (2H, m, H-5), 1.44-1.52 (1H, m, H-4$_{ax}$), 1.72-1.75 (1H, m, H$^4$eq), 2.32-2.38 (1H, dd, J=2.8 Hz, J=9.6 Hz, NHCH$_2$), 2.64-2.83 (5H, m, H-2, NHCH$_2$, Ph-CH$_2$), 2.90-2.93 (1H, m, H-3eq), 3.23 (1H, dt, J=3.2 Hz, J=10.0 Hz, H-6$_{ax}$), 3.73-3.83 (2H, m, (Ph)$_2$CH and CH—OH), 7.12-7.31 (13H, m, ArH), 7.35-7.36 (2H, m, ArH). Optical rotation of free base, [α]$^{25}_D$=(−) 38.9° (c 0.57, MeOH). Free base was converted into oxalate salt 205-207° C.

Analysis calculated for (C$_{27}$H$_{32}$N$_2$O. 2(COOH)$_2$, 0.5H$_2$O) C, H, N.

Synthesis of (S)-1-[(3S,6S)-6-benzhydrylpiperidin-3-ylamino)-3-phenylpropan-2-ol (4d). Compound 3 (0.075 g, 0.281 mmol) was reacted with S-(−)-2,3-epoxypropyl benzene (0.056 g, 0.422 mmol) (Procedure A) and was purified by flash column chromatography over silica gel using diethyl ether/MeOH/Et$_3$N (90:10:0.2) to yield 4d (0.037 g, 33%). $^1$H NMR (400 MHz, CDCl$_3$): δ 1.23-1.35 (2H, m, H-5), 1.41-1.49 (1H, m, H-4$_{ax}$), 1.75-1.78 (1H, m, H-4$_{eq}$), 2.36-2.41 (1H, dd, J=3.2 Hz, J=8.8 Hz, NHCH$_2$), 2.66-2.84 (5H, m, H-2, NHCH$_2$, Ph-CH$_2$), 2.89-2.92 (1H, m, H-3$_{eq}$), 3.23 (1H, dt, J=2.4 Hz, J=10.0 Hz, H-6$_{ax}$), 3.75 (1H, d, J=10.0 Hz, (Ph)$_2$CH) 3.78-3.85 (1H, m, and CH—OH), 7.12-7.31 (13H, m, ArH), 7.35-7.36 (2H, m, ArH). Optical rotation, [α]$^{25}_D$=(−) 49.3° (c 0.96, MeOH). Free base was converted into oxalate salt 206-209° C.

Analysis calculated for (C$_{27}$H$_{32}$N$_2$O. 2(COOH)$_2$, 0.3H$_2$O) C, H, N.

Synthesis of 1-((5S,8S)-8-benzhydryl-1,4-diazabicyclo[3.3.1]nonane-2-yl)-3-phenylpropan-2-ol (6a and 6b). To a stirring solution of cis-(−)-8-benzhydryl-1,4-diazabicyclo[3.3.1]nonane 5 (0.100 g, 0.341 mmol) in dry ethanol was added 2,3-epoxypropyl benzene (0.068 g, 0.512 mmol). The reaction mixture was stirred overnight at 65° C. (Procedure A). The diastereomers were separated by preparative TLC using acetone/diethyl ether (20:80) as mobile phase to afford 6a and 6b. Upper Fraction gave 6a (0.026 g, 18%). $^1$H NMR (400 MHz, CDCl$_3$): δ 1.24-1.43 (2H, m, H-7), 1.54-1.66 (1H, m, H-6a), 2.03-2.06 (1H, m, H6$_{eq}$), 2.28 (1H, t, J=12.4 Hz, NCH$_2$CH), 2.39 (1H, bs, H-5), 2.57-2.87 (6H, m, NCH$_2$CH, NCH$_2$CH$_2$N, Ph-CH$_2$), 2.98-3.01 (1H, m, H-9$_{ax}$), 3.10 (1H, bd, J=11.8 Hz, NCH$_2$CH$_2$N), 3.22-3.25 (1H, m, H-9$_{eq}$) 3.77 (1H, dt, J=4.8 Hz, J=11.2 Hz, H-8$_{ax}$), 3.84-3.91 (2H, m, CH—OH, (Ph)$_2$CH), 7.11-7.15 (2H, m, ArH), 7.19-7.31 (1H, m, ArH), 7.35-7.38 (2H, m, ArH). [α]$^{25}_D$ (oxalate salt)=(−) 24.7° (c 0.42, MeOH).

Analysis calculated for (C$_{29}$H$_{34}$N$_2$O. 2(COOH)$_2$) C, H, N.
Lower fraction gave 6b (0.024 g, 16%). $^1$H NMR (400 MHz, CDCl$_3$): δ 1.22-1.29 (1H, m, H-7$_{ax}$), 1.34-1.42 (1H, m, H-7$_{eq}$), 1.47-1.56 (1H, m, H-6$_{ax}$), 2.02-2.07 (1H, m, H6$_{eq}$), 2.20 (1H, dd, J=10.8 Hz, J=2.4 Hz, NCH$_2$CH), 2.48 (1H, bm, H-5), 2.67 (1H, dd, J=8.0 Hz, J=5.6 Hz, NCH$_2$CH), 2.75-3.10 (7H, m, NCH$_2$CH$_2$N, Ph-CH$_2$, H-9$_{ax}$), 3.17-3.20 (1H, m, H-9$_{eq}$) 3.75 (1H, dt, J=4.8 Hz, J=11.3 Hz, H-8$_{ax}$), 3.83-3.90 (2H, m, CH—OH, (Ph)$_2$CH), 7.12-7.15 (2H, m, ArH), 7.19-7.30 (1H, m, ArH), 7.33-7.38 (2H, m, ArH). [α]$^{25}_D$ (oxalate salt)=(−) 31.2° (c 0.40, MeOH).

Analysis calculated for (C$_{29}$H$_{34}$N$_2$O. 2(COOH)$_2$) C, H, N.

Synthesis of (R)-2-((5S,8S)-8-benzhydryl-1,4-diazabicyclo[3.3.1]nonane-2-yl)-1-phenylethanol (7a). To a stirring solution of cis-(−)-8-benzhydryl-1,4-diazabicyclo[3.3.1]nonane 5 (0.065 g, 0.222 mmol) in dry ethanol was added R-(+)-2-phenyloxirane (0.04 g, 0.333 mmol) (Procedure A). The compound was purified by flash column chromatography by using diethyl ether/MeOH (9:1) to afford 7a (0.051 g, 56%). $^1$H NMR (400 MHz, CDCl$_3$): δ 1.26-1.33 (1H, m, H-7$_{ax}$), 1.38-1.47 (1H, m, H-7$_{eq}$), 1.54-1.63 (1H, m, H-6$_{ax}$), 2.00-2.03 (1H, m, H-6$_{eq}$), 2.38-2.47 (2H, m, NCH$_2$CH, H-5), 2.77 (1H, dd, J=3.6 Hz, J=12.4 Hz, NCH$_2$CH), 2.82-2.99 (3H, m, NCH$_2$CH$_2$N) 3.03-3.06 (1H, m, H-9$_{ax}$), 3.17-3.19 (1H, m, NCH$_2$CH$_2$N), 3.29-3.33 (1H, m, H-9$_{eq}$) 3.80 (1H, dt, J=4.4 Hz, J=10.8 Hz, H-8$_{ax}$), 3.91 (1H, d, J=11.6 Hz, (Ph)$_2$CH), 4.69 (1H, dd, J=3.2 Hz, J=11.2 Hz, CHOH), 7.10-7.38 (15H, m, ArH). [α]$^{25}_D$=(−) 52.3° (c 0.52, MeOH). Free base was converted into oxalate salt 194-197° C.

Analysis calculated for (C$_{28}$H$_{32}$N$_2$O. 2(COOH)$_2$) C, H, N.

Synthesis of (S)-2-((SS, 8S)-8-benzhydryl-1,4-diazabicyclo[3.3.1]nonane-2-yl)-1-phenylethanol (7b). Compound 5 (0.060 g, 0.205 mmol) was reacted with S-(−)-2-phenyloxirane (0.036 g, 0.307 mmol) (Procedure A) to yield 7b (0.045 g, 53%). $^1$H NMR (400 MHz, CDCl$_3$): δ 1.25-1.34 (1H, m, H-7$_{ax}$), 1.38-1.49 (1H, m, H-7$_{eq}$), 1.54-1.65 (1H, m, H-6$_{ax}$), 2.22-2.27 (1H, m, H6$_{eq}$), 2.34 (1H, dd, J=2.8 Hz, J=10.4 Hz, NCH$_2$CH), 2.46-2.49 (1H, m, NCH$_2$CH$_2$N), 2.64 (1H, bs, H-5), 2.91-3.11 (6H, m, NCH$_2$CH$_2$N, NCH$_2$CH, H-9$_{ax}$), 3.24-3.27 (1H, m, H-9$_{eq}$) 3.72-3.83 (1H, m, H-8$_{ax}$), 3.88 (1H, d, J=11.6 Hz, (Ph)$_2$CH), 4.67 (1H, dd, J=3.6 Hz, J=10.0 Hz, CHOH), 7.10-7.37 (15H, m, ArH). [α]$^{25}_D$=(−) 45.8° (c 0.52, MeOH). Free base was converted into oxalate salt 193-195° C.

Analysis calculated for (C$_{28}$H$_{32}$N$_2$O. 2(COOH)$_2$, 0.3H$_2$O) C, H, N.

Synthesis of (R)-2-((5S,8S)-8-benzhydryl-1,4-diazabicyclo[3.3.1]nonane-2-yl)-1-4-fluorophenyl)ethanol (7c). Compound 5 (0.060 g, 0.205 mmol) was reacted with R-(−)-2-(4-fluorophenyl)oxirane (0.042 g, 0.307 mmol) (Procedure A) to yield 7c (0.034 g, 39%). $^1$H NMR (400 MHz, CDCl$_3$): δ 1.25-1.32 (1H, m, H-7$_{ax}$), 1.35-1.47 (1H, m, H-7$_{eq}$), 1.54-1.64 (1H, m, H-6$_{ax}$), 2.00-2.03 (2H, m, H-6$_{eq}$), 2.32-2.38 (1H, dd, J=11.2 Hz, J=0.8 Hz, NCH$_2$CH), 2.44 (1H, bs, H-5), 2.73 (1H, dd, J=3.6 Hz, J=12.8 Hz, NCH$_2$CH), 2.79-2.96 (3H, m, NCH$_2$CH$_2$N), 3.02-3.06 (1H, m, H-9$_{ax}$), 3.16-3.19 (1H, bm, NCH$_2$CH$_2$N), 3.27-3.31 (1H, m, H-9$_{eq}$) 3.75-3.86 (1H, m, H-8$_{ax}$), 3.90 (1H, d, J=11.2 Hz, (Ph)$_2$CH), 4.66 (1H, dd, J=3.2 Hz, J=10.8 Hz, CHOH), 7.03 (2H, t, J=8.4 Hz, ArH), 7.10-7.38 (12H, m, ArH). [α]$^{25}_D$ (free base)=(−) 45.5° (c 0.57, MeOH). Free base was converted into oxalate salt 189-191° C.

Analysis calculated for (C$_{28}$H$_{31}$FN$_2$O. 2(COOH)$_2$, 0.2H$_2$O) C, H, N.

Synthesis of (S)-2-((5S,8S)-8-benzhydryl-1,4-diazabicyclo[3.3.1]nonane-2-yl)-1-4-fluorophenyl)ethanol (7d). Compound 5 (0.070 g, 0.239 mmol) was reacted with S-(+)-2-(4-fluorophenyl)oxirane (0.049 g, 0.358 mmol) (Procedure A) to yield 7d (0.040 g, 39%). $^1$H NMR (400 MHz, CDCl$_3$): δ 1.27-1.34 (1H, m, H-7$_{ax}$), 1.37-1.49 (1H, m, H-7$_{eq}$), 1.59-

1.68 (1H, m, H-6$_{ax}$), 2.20-2.32 (2H, m, H-6$_{eq}$, NCH$_2$CH), 2.45-2.49 (1H, m, NCH$_2$CH$_2$N), 2.62 (1H, bs, H-5), 2.91-3.11 (5H, m, NCH$_2$CH$_2$N, NCH$_2$CH, H-9$_{ax}$), 3.23-3.28 (1H, m, H9$_{eq}$), 3.75-3.82 (1H, m, H-8$_{ax}$), 3.88 (1H, d, J=11.2 Hz, (Ph)$_2$CH), 4.64 (1H, dd, J=3.2 Hz, J=10.0 Hz, CHOH), 6.99-7.04 (2H, m, ArH), 7.10-7.37 (12H, m, ArH). [α]$^{25}_D$ (free base)=(−) 44.0° (c 0.56, MeOH). Free base was converted into oxalate salt 191-193° C.

Analysis calculated for (C$_{28}$H$_{31}$FN$_2$O. 2(COOH)$_2$, 0.3H$_2$O) C, H, N.

Synthesis of 3-((1S,6S)-6-benzhydryl-2,5-diazabicyclo[3.3.1]nonane-2-yl)-1-(4-fluorophenyl)propan-1-one (8). Into a stirred solution of cis-(−)-8-benzhydryl-1,4-diazabicyclo[3.3.1] nonane 5 (0.250 g, 0.854 mmol) in dry acetonitrile was added K$_2$CO$_3$ (0.354 g, 2.56 mmol) followed by 3-chloro-4'-fluoro propiophenone (0.207 g, 1.11 mmol). Catalytic amount of potassium iodide was added and the reaction mixture was refluxed for 3 h under nitrogen atmosphere. After evaporation of solvent, the residue was dissolved in water and extracted with CH$_2$Cl$_2$ (2×100 ml), dried over Na$_2$SO$_4$ and evaporated. The compound was purified by flash column chromatography using diethyl ether/MeOH/Et$_3$N (93:7:0.2) to afford 8 (0.260 g, 68%). $^1$H NMR (400 MHz, CDCl$_3$): δ 1.25-1.34 (1H, m, H-7$_{ax}$), 1.34-1.45 (1H, m, H-7$_{eq}$), 1.48-1.58 (1H, m, H-6$_{ax}$), 2.20-2.23 (1H, m, H6$_{eq}$), 2.52 (1H, bs, H-5), 2.62-2.65 (1H, m, NCH$_2$CH$_2$), 2.80-3.16 (8H, m, NCH$_2$CH$_2$N, NCH$_2$CH$_2$, CH$_2$CO, H-9a), 3.20-3.23 (1H, m, H-9$_{eq}$) 3.77 (1H, dt, J=4.4 Hz, J=11.2 Hz, H-8$_{ax}$), 3.89 (1H, d, J=11.8 Hz, (Ph)$_2$CH), 7.08-7.15 (2H, m, ArH), 7.20-7.28 (6H, m, ArH), 7.36 (2H, d, J=7.2 Hz, ArH), 7.95-7.99 (2H, dt, J=2.0 Hz, J=5.2 Hz, ArH).

Synthesis of 3-((1S,6S)-6-benzhydryl-2,5-diazabicyclo[3.3.1]nonane-2-yl)-1-(4-fluorophenyl)propan-1(R & S)-ol (9). To a stirred solution of compound 8 (0.250 g, 0.564 mmol) dissolved in 25 ml of THF was added NaBH$_4$ (0.025 g, 0.677 mmol) followed by addition of 0.5 ml of water. The reaction mixture was stirred for 3 h under nitrogen atmosphere at RT. Water (5 ml) was added next into the reaction mixture. The solvent was evaporated and the residue was dissolved in water and extracted with CH$_2$Cl$_2$ (2×50 ml), dried over Na$_2$SO$_4$ and evaporated in vacuo. The crude product was purified by flash column chromatography using diethyl ether/MeOH/Et$_3$N (93:8:0.2) to afford 9 (0.195 g, 79%). $^1$H NMR (400 MHz, CDCl$_3$): δ 1.25-1.41 (2H, m, H-7$_{ax}$, H-7$_{eq}$), 1.47-1.95 (3H, m, CH$_2$CHOH, H-6$_{ax}$), 2.09-2.18 (1H, m, H6$_{eq}$), 2.59-2.96 (6H, m, H-5, NCH$_2$CH$_2$, NCH$_2$CH$_2$N), 3.04 (1H, d, J=13.2 Hz, H-9$_{ax}$), 3.12-3.25 (2H, m, NCH$_2$CH$_2$N, H9$_{eq}$), 3.73-3.82 (1H, m, H-8$_{ax}$), 3.88 (1H, dd, J=1.6 Hz, J=11.6 Hz, (Ph)$_2$CH), 4.84-4.95 (1H, m, CHOH), 7.00 (2H, dt, J=1.6 Hz, J=8.4 Hz, ArH), 7.10-7.16 (2H, m, ArH), 7.19-7.37 (10H, m, ArH).

Synthesis of 3-((1S,6S)-6-benzhydryl-2,5-diazabicyclo[3.3.1]nonane-2-yl)-1-(4-fluorophenyl) propyl-4,7,7-trimethyl-3-oxo-2-oxabicyclo[2.2.1]heptane-1-carboxylate (10a and 10b). To a stirred solution of 3-((1S,6S)-6-benzhydryl-2,5-diazabicyclo[3.3.1]nonane-2-yl)-1-(4-fluorophenyl)propan-1 (R & S)-ol 9 (0.195 g, 0.438 mmol), Et$_3$N (0.088 g, 0.876 mmol), and DMAP (10 mg) in 100 ml of dry CH$_2$Cl$_2$ under nitrogen atmosphere at 0° C. was added (1S)-(−)-camphanic chloride (0.123 g, 0.569 mmol) dissolved in 10 ml dry CH$_2$Cl$_2$. The reaction mixture was stirred at 0° C. for 30 min and at room temperature for 3 h under nitrogen. The reaction mixture was quenched with water (20 ml) and then diluted with CH$_2$Cl$_2$ (50 ml). Organic layer was separated and the aqueous layer was extracted with CH$_2$Cl$_2$ (2×50 ml), dried over Na$_2$SO$_4$ and evaporated in vacuo. The crude product was purified by flash column chromatography over silica gel using diethyl ether/MeOH (95:5) to afford mixture of two diastereoisomers 10a and 10b (0.250 g, 91%). The diastereoisomers were separated by semipreparative HPLC using a normal phase column (Nova-pack silica 6 μm). Hexanes/2-propanol/Et$_3$N (92:8:0.3) was used as a mobile phase with a flow rate of 12 mL/min. The two fractions were eluted with retention time 2.83 min and 3.30 min for 10a and 10b, respectively.

Eluting first was 10a (0.115 g, 42%). $^1$H NMR (400 MHz, CDCl$_3$): δ 0.79 (3H, s, CH$_3$), 0.97 (3H, s, CH$_3$), 1.07 (3H, s, CH$_3$), 1.24-1.49 (2H, m, H-7$_{ax}$, H-7$_{eq}$) 1.62-1.68 (1H, m, H-6$_{ax}$), 1.84-2.07 (3H, m, CH$_2$CHO, H-6$_{eq}$), 2.16-2.49 (5H, m, H-5, CCH$_2$C, NCH$_2$CH$_2$N), 2.59-2.63 (1H, m, NCH$_2$CH$_2$N), 2.68-2.75 (1H, m, NCH$_2$CH$_2$), 2.86-2.98 (2H, m, NCH$_2$CH$_2$, H-9$_{ax}$), 3.09-3.12 (1H, m, NCH$_2$CH$_2$N), 3.18-3.21 (1H, m, H9$_{eq}$), 3.75 (1H, dt, J=4.4 Hz, J=11.2 Hz, H-8$_{ax}$), 3.87 (1H, d, J=11.2 Hz, (Ph)$_2$CH), 5.94 (1H, t, J=7.2 Hz, CHOCO), 6.97-7.03 (2H, m, ArH), 7.09-7.14 (2H, m, ArH), 7.19-7.27 (6H, m, ArH), 7.30-7.37 (4H, m, ArH).

Eluting second was 10b (0.105 g, 38%). $^1$H NMR (400 MHz, CDCl$_3$): δ 0.88 (3H, s, CH$_3$), 0.98 (3H, s, CH$_3$), 1.09 (3H, s, CH$_3$), 1.23-1.52 (2H, m, H-7$_{ax}$, H-7$_{eq}$), 1.62-1.68 (1H, m, H-6$_{ax}$), 1.84-1.99 (2H, m, CH$_2$CHO), 2.04-2.07 (1H, m, H-6$_{eq}$), 2.12-2.52 (5H, m, H-5, CCH$_2$C, NCH$_2$CH$_2$N), 2.68-2.75 (1H, m, NCH$_2$CH$_2$), 2.84-2.92 (1H, m, NCH$_2$CH$_2$), 2.95-2.99 (1H, m, H-9$_{ax}$), 3.08-3.11 (1H, m, NCH$_2$CH$_2$N), 3.18-3.22 (1H, m, H9$_{eq}$), 3.76 (1H, dt, J=4.8 Hz, J=11.2 Hz, H-8$_{ax}$), 3.87 (1H, d, J=11.6 Hz, (Ph)$_2$CH), 5.92 (1H, t, J=6.8 Hz, CHOCO), 6.98-7.03 (2H, m, ArH), 7.09-7.15 (2H, m, ArH), 7.19-7.37 (10H, m, ArH).

Procedure B. Synthesis of (−)11a. The first eluting camphanic ester fraction 10a (0.075 g, 0.120 mmol) was hydrolyzed with K$_2$CO$_3$ (20 mg) in methanol (20 ml) at room temperature for 12 h. Methanol was evaporated, water (20 ml) was added and the product was extracted with ethyl acetate (2×50 ml). Organic layer was dried over Na$_2$SO$_4$ and evaporated under reduced pressure. The crude product was purified by flash column chromatography over silica using diethyl ether/MeOH/Et$_3$N (93:8:0.2) to afford 11a (0.048 g, 90%). $^1$H NMR (400 MHz, CDCl$_3$): δ 1.25-1.44 (2H, m, H-7$_{ax}$, H-7$_{eq}$), 1.54-1.69 (2H, m, CH$_2$CHOH, H-6a), 1.80-1.90 (1H, m, CH$_2$CHOH), 2.15-2.18 (1H, m, H6$_{eq}$), 2.63 (1H, bs, H-5), 2.67-2.974 (1H, m, NCH$_2$CH$_2$), 2.79-2.95 (4H, m, NCH$_2$CH$_2$, NCH$_2$CH$_2$N), 3.04 (1H, d, J=13.2 Hz, H-9$_{ax}$), 3.13-3.18 (1H, m, NCH$_2$CH$_2$N), 3.22-3.25 (1H, m, H9$_{eq}$), 3.79 (1H, dt, J=4.8 Hz, J=11.6 Hz, H-8$_{ax}$), 3.88 (1H, d, J=11.6 Hz, (Ph)$_2$CH), 4.86 (1H, dd, J=2.4 Hz, J=9.6 Hz, CHOH), 7.00 (2H, t, J=8.8 Hz, ArH), 7.11-7.16 (2H, m, ArH), 7.19-7.37 (10H, m, ArH). [α]$^{25}_D$=(−) 38.7 (c 1.08, MeOH). Free base was converted into oxalate salt 191-193° C.

Analysis calculated for (C$_{29}$H$_{33}$FN$_2$O. 2(COOH)$_2$, 1.5H$_2$O) C, H, N.

Synthesis of (−)11b. The second eluting fraction 10b (0.105 g, 0.168 mmol) was hydrolyzed with K$_2$CO$_3$ (20 mg) in methanol (20 ml) to afford 11b (0.071 g, 94%) (Procedure B). $^1$H NMR (400 MHz, CDCl$_3$): δ 1.24-1.43 (2H, m, H-7$_{ax}$, H-7$_{eq}$), 1.48-1.54 (1H, m, H-6a), 1.71-1.79 (1H, m, CH$_2$CHOH), 1.88-1.95 (1H, m, CH$_2$CHOH), 2.09-2.12 (1H, m, H6$_{eq}$), 2.60-2.66 (2H, m, H-5, NCH$_2$CH$_2$), 2.76-2.97 (4H, m, NCH$_2$CH$_2$, NCH$_2$CH$_2$N), 3.04 (1H, d, J=13.2 Hz, H-9a), 3.12-3.15 (1H, m, NCH$_2$CH$_2$N), 3.21-3.24 (1H, m, H-9$_{eq}$), 3.78 (1H, dt, J=4.8 Hz, J=11.6 Hz, H-8$_{ax}$), 3.88 (1H, d, J=11.6 Hz, (Ph)$_2$CH), 4.94 (1H, dd, J=3.2 Hz, J=7.6 Hz, CHOH), 7.00 (2H, t, J=8.4 Hz, ArH), 7.10-7.16 (2H, m, ArH), 7.20-7.37 (10H, m, ArH). [α]$^{25}_D$=(−) 56.8° (c 1.0, MeOH). Free base was converted into oxalate salt 193-195° C.

Analysis calculated for (C$_{29}$H$_{33}$FN$_2$O. 2(COOH)$_2$, 0.5H$_2$O) C, H, N.

Transporter assays. The affinity of test compounds in binding to rat DAT and in inhibiting monoamine uptake was monitored as described by us previously. Briefly, rat striatum was used for measuring binding of [$^3$H]WIN 35,428 by DAT and uptake of [$^3$H]DA by DAT. Rat cerebral cortex was used for assessing uptake of [$^3$H]serotonin by SERT and hippocampus for uptake of [³H]NE by NET. Nonspecific binding at DAT was defined with 100 uM cocaine; nonspecific uptake at DAT, SERT, and NET with 100 uM cocaine, 10 uM citalopram, and 10 uM desipramine, respectively. Test compounds were dissolved in dimethyl sulfoxide (DMSO), diluted out in 10% (v/v) DMSO, and added to assays resulting in a final DMSO concentration of 0.5% which by itself did not interfere with the assays. At lease five triplicate concentrations of each test compound were studied, spaced evenly around the IC50 value. The latter was estimated by nonlinear computer curve-fitting procedures and converted to $K_i$ with the Cheng-Prusoff equation.

Results and Discussion for the Compounds of FIGS. 10 Through 12

Design of compounds 4a-b and 4c-d involved introduction of an exocyclic hydroxyl group to 3,6-disubstituted template. Between compounds 4a and 4b, compound 4b has the hydroxyl group in a S-configuration as it was synthesized from S-epoxide. Compound 4b was more potent in inhibiting uptake of radiolabeled DA and NE by DAT and NET, respectively, compared to 4a (Ki (DAT)=236 nM Vs. 152 nM for 4a and 4b, respectively and Ki (NET)=1435 Vs. 306 nM for 4a and 4b, respectively). Thus, the difference in NE uptake inhibitory activity between the two compounds was much greater than the DA uptake inhibitory activity.

In designing the additional compounds, an additional methylene unit was introduced between the phenyl moiety and the hydroxyl center. This transformation made 4c-d more potent DAT uptake inhibitors compared to 4a-b (Table 7 in FIG. 15). Both 4c and 4d exhibited low nanomolar activity for inhibition of DA uptake activity (Ki (DAT)=25 nM and 25.3 nM for 4c and 4d, respectively) and also the same relative potency was exhibited in the binding assay with the radiolabeled tropane ligand CFT. It is interesting to note that both compounds exhibited comparable inhibition activity, thus, not exhibiting any preference for chirality of the hydroxyl center. Thus, a minor change in molecular structure resulted in almost ten-fold increase of DAT inhibition potency in 4c-d compared to 4a-b.

In designing additional analogues, the bicyclic (−)-diamine template was chosen for introduction of exocyclic hydroxyl group. Thus in compounds 6a and 6b, which represent bicyclic versions of 4c and 4d, a hydroxyl functionality was introduced with R- and S-stereocenters. These molecules exhibited differential potencies for inhibition of DA uptake with the S-hydroxyl stereo-center exhibiting greater potency than the R stereo-center (Ki (DAT)=16.8 nM Vs. 82.9 nM for 6b and 6a, respectively). Thus, this result was somewhat different compared to their 3,6-disubstituted counterparts 4c-d. Compound 6b was 5 times more potent in inhibiting DA uptake than 6a (Table 7). This might indicate an effect of a more constrained bicyclic structure on greater selectivity and affinity for DAT. The next series of compounds 7a-d, which represents more constrained bicyclic versions of 4a-b, yielded results from weak to strong potency for the DAT. However, these molecules, in contrary to previous derivatives, produced preferential interaction with DAT with an exocyclic hydroxyl group in the R-stereo center. The most potent compound identified in the 7-series was fluoro derivative 7c, exhibiting the highest potency for DAT (Ki=66.5 nM). In general, fluoro derivatives were more potent compared to unsubstituted versions. In general, compounds 7a-d were much less potent than 6a-b, indicating the importance of N-alkyl chain length in transporter interaction.

In additional two bicyclic amine analogues, 11a and 11b, the hydroxyl group was introduced in the benzyl position at the terminus of the propyl chain. Thus, in these two compounds the hydroxyl group was located furthest from the N-atom as compared to previous analogues. It is evident from uptake inhibition data that such location of the hydroxyl group produced maximal inhibition of DA uptake in one of the diastereomers, 11b (Ki=8.63 nM). Thus, compound 11b exhibited maximum potency and selectivity for inhibition of dopamine uptake compared to inhibition of both serotonin and norepinephrine (SERT/DAT and NET/DAT; 172 and 48.4, Table 8 in FIG. 16). In fact, compound 11b turned out to be the most potent and selective compound in this current series of molecules. The diastereomer 11a, on the other hand, was less potent compared to 11b even though its potency was comparable to the third best compound 4d in the series (Ki (DAT)=41.8 nM and 25.3 nM, respectively for 11a and 4d). It is evident from this result that the location of the hydroxyl group with respect to the aromatic ring and the N-atom played an important role in uptake inhibition activity. FIG. 17 provide elemental analysis for the compounds of FIGS. 10-12

The compounds of the present embodiment include an N-propyl linker length that is optimal for interaction with DAT. Position of an exo-cyclic hydroxyl group in the benzylic position of the N-propyl terminus produces the most active and selective DAT compound 11b in the current series. In most cases a stereochemical preference was exhibited for the hydroxyl stereo center. In general, hydroxyl compound derived from more constrained bicyclic amine produced greater selectivity for DAT than 3,6-disubstituted amine derivatives.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention

What is claimed is:

1. A compound having formula:

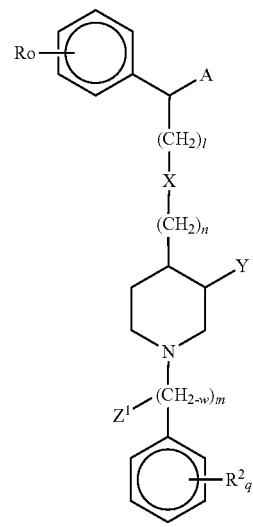

wherein:

$Z^1$ is —NH$_2$, —OH, =O, Oalkyl, —Oaryl, or —O—C(O)—R$^5$;

w is a number representing that one or more hydrogen atoms of one or more methylene groups are replaced by $Z^1$;

A is

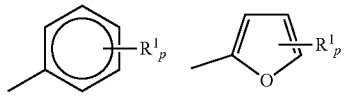

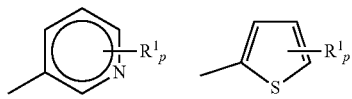

X is selected from the group consisting of —NH—, —NR$^4$, and —O—;

R$^4$ is C$_{1-4}$ alkyl, NH$_2$, C$^{1-4}$ hydroxyalkyl, halogenated C$_{1-4}$ alkyl, C$_{2-4}$ alkenyl, C$_{2-4}$ hydroxyalkenyl, halogenated C$_{2-4}$ alkenyl, C$_{2-4}$ and alkynyl, or C$_{2-4}$ halogenated alkynyl;

Y is —H, —NH$_2$, —OH, =O, or —O—C(O)—R$^5$;

l is 0, 1, or 2;

n is 1 or 2;

m is 1, 2, 3 or 4;

o is 0, 1, 2, 3, or 4;

p is 0, 1, 2, 3, or 4;

q is 0, 1, 2, or 3;

R, R$^1$, and R$^2$ are selected from the group consisting of H, F, Cl, Br, I, CN, COOEt, OH, NO$_2$, NH$_2$, OR$^5$, wherein R$^5$ is C$_{1-18}$ alkyl, C$_{5-6}$ cycloalkyl, or C$_{2-8}$ alkenyl or R$^2$ is a 5 or 6 membered heterocycle;

and where one or more CH$_2$, groups of (CH$_2$)$_m$ are optionally substituted by CR$^7$R$^{t7}$;

R$^7$ is H, —OR$^{11}$, or NR$^{11}$;

R$^{t7}$ is H, —C$_{1-8}$ alkyl or R$^7$, R$^{t7}$ are combined together as =O;

R$^{11}$ is H, C$_{1-8}$ alkyl, C$_{2-8}$ alkylene, C$_{6-8}$ alkyl-aryl, or —COOR$^{12}$; and R$^{12}$ is C$_{1-8}$ alkyl, C$_{2-8}$ alkylene, OR C$_{6-18}$ alkyl-aryl;

or a pharmaceutically acceptable salt or derivative thereof.

2. The compound of claim 1 having the formula:

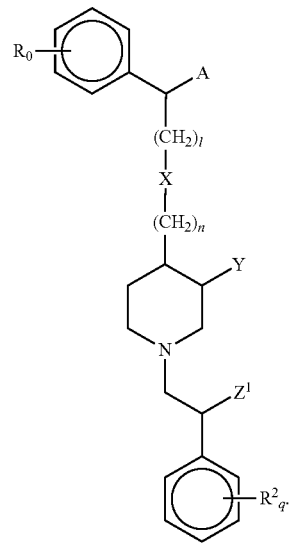

3. The compound of claim 1 wherein $Z^1$ is H.

4. The compound of claim 1 wherein $Z^1$ is OH.

5. The compound of claim 1 wherein m is 2.

6. A compound having the formula:

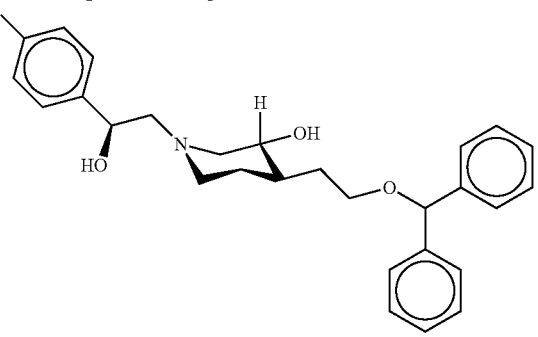

or a pharmaceutically acceptable salt thereof.

7. A compound having the formula:

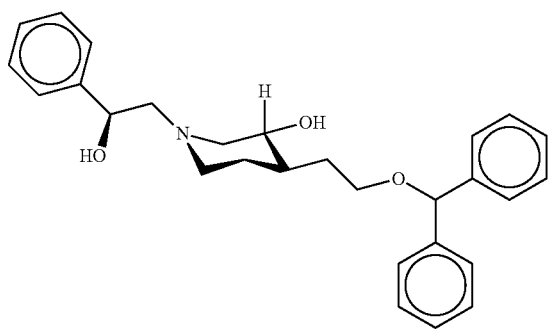

or a pharmaceutically acceptable salt thereof.

8. The compound of claim 1 having the formula:
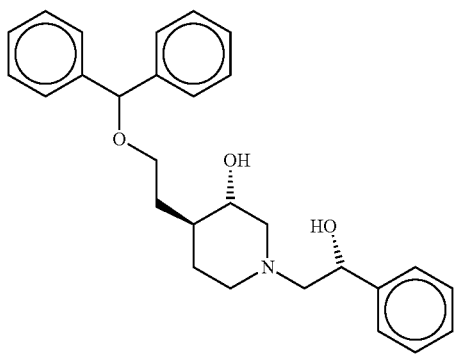
or a pharmaceutically acceptable salt thereof.
9. The compound of claim 1 having the formula:
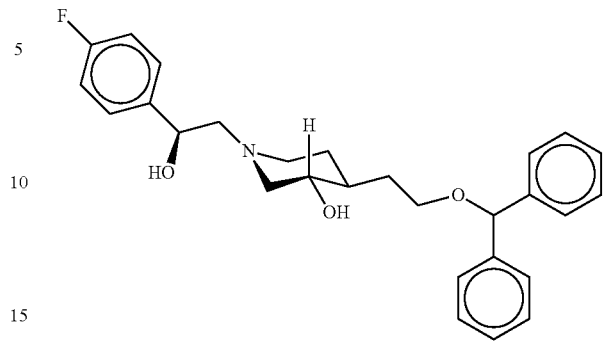
or a pharmaceutically acceptable salt thereof.
* * * * *